(12) United States Patent
Krause et al.

(10) Patent No.: US 11,649,455 B2
(45) Date of Patent: May 16, 2023

(54) MICRO RNA EXPRESSION CONSTRUCTS AND USES THEREOF

(71) Applicants: UNIVERSITY OF GENEVA, Geneva (CH); LES HÔPITAUX UNIVERSITAIRES DE GENÈVE, Geneva (CH); UNIVERSITY OF ZURICH, Zurich (CH)

(72) Inventors: Karl-Heinz Krause, Geneva (CH); Francis Rousset, Geneva (CH); Patrick Salmon, Geneva (CH); Marco Alessandrini, Geneva (CH); Roberto Speck, Zurich (CH); Simon Bredl, Zurich (CH); Tafadzwa Mlambo, Zurich (CH); Renier Myburgh, Zurich (CH)

(73) Assignees: UNIVERSITY OF GENEVA, Geneva (CH); LES HÔPITAUX UNIVERSITAIRES DE GENÈVE, Geneva (CH); UNIVERSITY OF ZURICH, Zurich (CH)

( * ) Notice: Subject to any disclaimer, the term of this patent is extended or adjusted under 35 U.S.C. 154(b) by 0 days.

(21) Appl. No.: 15/733,703

(22) PCT Filed: Apr. 1, 2019

(86) PCT No.: PCT/IB2019/000328
§ 371 (c)(1),
(2) Date: Sep. 30, 2020

(87) PCT Pub. No.: WO2019/186274
PCT Pub. Date: Oct. 3, 2019

(65) Prior Publication Data
US 2021/0095278 A1    Apr. 1, 2021

Related U.S. Application Data

(60) Provisional application No. 62/650,387, filed on Mar. 30, 2018, provisional application No. 62/650,403, filed on Mar. 30, 2018.

(51) Int. Cl.
*C12N 15/113* (2010.01)
*C12N 15/86* (2006.01)
*C12Q 1/68* (2018.01)

(52) U.S. Cl.
CPC ............ *C12N 15/113* (2013.01); *C12N 15/86* (2013.01); *C12N 2310/11* (2013.01); *C12N 2310/141* (2013.01); *C12N 2310/531* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 5,302,523 | A | 4/1994 | Coffee et al. |
| 5,322,783 | A | 6/1994 | Tomes et al. |
| 5,384,253 | A | 1/1995 | Krzyzek et al. |
| 5,464,765 | A | 11/1995 | Coffee et al. |
| 5,486,359 | A | 1/1996 | Caplan et al. |
| 5,538,877 | A | 7/1996 | Lundquist et al. |
| 5,538,880 | A | 7/1996 | Lundquist et al. |
| 5,550,318 | A | 8/1996 | Adams et al. |
| 5,563,055 | A | 10/1996 | Townsend et al. |
| 5,580,859 | A | 12/1996 | Felgner et al. |
| 5,589,466 | A | 12/1996 | Felgner et al. |
| 5,591,616 | A | 1/1997 | Hiei et al. |
| 5,610,042 | A | 3/1997 | Chang et al. |
| 5,656,610 | A | 8/1997 | Shuler et al. |
| 5,702,932 | A | 12/1997 | Hoy et al. |
| 5,736,524 | A | 4/1998 | Content et al. |
| 5,780,448 | A | 7/1998 | Davis |
| 5,789,215 | A | 8/1998 | Berns et al. |
| 5,908,782 | A | 6/1999 | Marshak et al. |
| 5,945,100 | A | 8/1999 | Fick |
| 5,981,274 | A | 11/1999 | Tyrrell et al. |
| 5,994,136 | A | 11/1999 | Naldini et al. |
| 5,994,624 | A | 11/1999 | Trolinder et al. |
| 6,013,516 | A | 1/2000 | Verma et al. |
| 6,506,559 | B1 | 1/2003 | Fire et al. |
| 6,573,099 | B2 | 6/2003 | Graham |
| 6,673,611 | B2 | 1/2004 | Thompson et al. |
| 9,556,433 | B2 | 1/2017 | Krause et al. |
| 2003/0051263 | A1 | 3/2003 | Fire et al. |

(Continued)

FOREIGN PATENT DOCUMENTS

| | | |
|---|---|---|
| CN | 101993892 | 3/2011 |
| CN | 105861551 | 8/2016 |

(Continued)

OTHER PUBLICATIONS

Urusov et al. Cells vol. 7(10) 11 pages.*
Carneiro et al., "Abstract No. 897: Co-expression of chimeric antigen receptor (CAR) and miRNAs to T cell therapy," *European Journal of Cancer*, 50(Suppl. 5):s219, 2014.
Office Communication issued in European Patent Application No. 19732112.8, dated Jan. 27, 2022.
Park et al., "Gamma-retroviral vector design for the co-expression of artificial microRNAs and therapeutic proteins," *Nucleic Acid Therapeutics*, 24(5):356-363, 2014.
Supplemental information for Rousset et al., "Optimizing Synthetic miRNA Minigene Architecture for Efficient miRNA Hairpin Concatenation and Multi-target Gene Knockdown," *Molecular Therapy—Nucleic Acids*, 14:351-363 2018.

(Continued)

*Primary Examiner* — Sean McGarry
(74) *Attorney, Agent, or Firm* — ParkerHighlander, PLLC

(57) ABSTRACT

The present disclosure relates to miRNA expression constructs, such as for expression of multiple miRNAs and use thereof to knockdown target gene expression. In some aspects, the expression constructs include a promoter element, a spacer sequence and a miRNA coding sequence. In some aspects, constructs provide enhanced immune cell function.

17 Claims, 17 Drawing Sheets

Specification includes a Sequence Listing.

(56) References Cited

U.S. PATENT DOCUMENTS

| | | |
|---|---|---|
| 2003/0055020 A1 | 3/2003 | Fire et al. |
| 2003/0159161 A1 | 8/2003 | Graham et al. |
| 2004/0019001 A1 | 1/2004 | McSwiggen |
| 2004/0064842 A1 | 4/2004 | Graham et al. |
| 2004/0265839 A1 | 12/2004 | Mello et al. |
| 2015/0051267 A1 | 2/2015 | Fekete et al. |

FOREIGN PATENT DOCUMENTS

| | | |
|---|---|---|
| CN | 105886473 | 8/2016 |
| CN | 106282212 | 1/2017 |
| CN | 107312800 | 11/2017 |
| EP | 1507865 | 7/2008 |
| JP | 2014-504862 | 2/2014 |
| JP | 2015-524264 | 8/2015 |
| WO | WO 1994/009699 | 5/1994 |
| WO | WO 1995/006128 | 3/1995 |
| WO | WO 1996/039487 | 12/1996 |
| WO | WO 2005/028630 | 3/2005 |
| WO | WO 2009/066758 | 5/2009 |
| WO | WO 2010/079430 | 7/2010 |
| WO | WO 2012/094193 | 7/2012 |
| WO | WO 2014/016817 | 1/2014 |
| WO | WO 2014/134165 | 9/2014 |
| WO | WO 2015/084897 | 6/2015 |
| WO | WO 2016/069283 | 5/2016 |
| WO | WO 2016/196388 | 12/2016 |
| WO | WO 2017/082174 | 5/2017 |
| WO | WO 2017/204874 | 11/2017 |
| WO | WO 2018/009246 | 1/2018 |
| WO | WO 2018/018958 | 2/2018 |
| WO | WO 2018/057855 | 3/2018 |

OTHER PUBLICATIONS

"*Homo sapiens* microsomal glutathione S-transferase 2 (MGST2) mRNA, complete cds," EBI Accession No. U77604, Jan. 2, 1997.

Aiuti et al., "Lentiviral hematopoietic stem cell gene therapy in patients with Wiskott-Aldrich syndrome," *Science*, 341(6148):1233151, 2013.

Anderson et al., "Lag-3, Tim-3, and TIGIT: Co-inhibitory Receptors with Specialized Functions in Immune Regulation," *Immunity*, 44(5):989-1004, 2016.

Beatty and O'Hara, "Chimeric antigen receptor-modified T cells for the treatment of solid tumors: Defining the challenges and next steps," *Pharmacol Ther.*, 166:30-9, 2016.

Biffi et al., "Lentiviral hematopoietic stem cell gene therapy benefits metachromatic leukodystrophy," *Science*, 341(6148):1233158, 2013.

Boudreau et al., "Artificial microRNAs as siRNA shuttles: improved safety as compared to shRNAs in vitro and in vivo," *Mol. Ther.*, 17(1):169-175, 2009.

Boudreau et al., "Minimizing variables among hairpin-based RNAi vectors reveals the potency of shRNAs," *RNA*, 14:1834-1844, 2008.

Bourhill et al., "Successful disabling of the 5' UTR of HCV using adeno-associated viral vectors to deliver modular multimeric primary microRNA mimics," *J. Virol. Methods*, 235:26-33, 2016.

Fesnak et al., "Engineered T cells: the promise and challenges of cancer immunotherapy," *Nat Rev Cancer*, 16(9):566-81, 2016.

Fowler et al., "Improved knockdown from artificial microRNAs in an enhanced miR-155 backbone: a designer's guide to potent multi-target RNAi," *Nucleic Acids Res.*, 44(5):e48, 2016.

Giry-Laterriere et al., "Lentiviral vectors," In: *Methods in Molecular Biology*, Merten and Al-Rubeai, Eds., Chapter 8, 737:183-209, 2011.

Giry-Laterriere et al., "Polyswitch lentivectors: "all-in-one" lentiviral vectors for drug-inducible gene expression, live selection, and recombination cloning," *Hum. Gene Ther.*, 22(10):1255-1267, 2011.

Grimm, "The dose can make the poison: lessons learned from adverse in vivo toxicities caused by RNAi overexpression," *Silence* 2:8, 6 pages, 2011.

Han et al. "Recent clinical trials utilizing chimeric antigen receptor T cells therapies against solid tumors," *Cancer Lett.*, 390:188-200, 2017.

Hu et al., "Comparative studies of various artificial microRNA expression vectors for RNAi in mammalian cells," *Mol. Biotechnol.*, 46(1):34-40, 2010.

Huang et al., "Construction and detection of expression vectors of mircoRNA-9a in BmN cells," *J. Zhejiang Univ. Sci. B: (Biomed. & Biotechol.)*, 12(7):527-533, 2011.

Hudson et al., "MicroRNA-106b-25 cluster expression is associated with early disease recurrence and targets caspase-7 and focal adhesion in human prostate cancer," *Oncogene*, 32(35):4139-4147, 2012.

Irving et al. "Engineering Chimeric Antigen Receptor T-Cells for Racing in Solid Tumors: Don't Forget the Fuel," *Front Immunol.*, 8:267, 2017.

Jackson et al., "Driving CAR T-cells forward," *Nat Rev Clin Oncol.*, 13(6):370-83, 2016.

Jaquet et al., "NADPH oxidase (NOX) isoforms are inhibited by celastrol with a dual mode of action," *Br J Pharmacol*, 164(2b):507-520, 2011.

Lee et al., "MicroRNA genes are transcribed by RNA polymerase II," *Embo. J.*, 23(20):4051-4060, 2004.

Liu and Berkhout, "Design of lentivirally expressed siRNAs," *Methods Mol. Biol.*, 942:233-257, 2013.

Liu et al., "Inhibition of HIV-1 by multiple siRNAs expressed from a single microRNA polycistron," *Nucleic Acids Res.*, 36:2811-2824, 2008.

Maczuga et al., "Embedding siRNA sequences targeting apolipoprotein B100 in shRNA and miRNA scaffolds results in differential processing and in vivo efficacy," *Mol. Ther.*, 21(1):217-227, 2013.

Mottet-Osman et al., "Suppression of the Sendai virus M protein through a novel short interfering RNA approach inhibits viral particle production but does not affect viral RNA synthesis," *J. Virol.*, 81(6):2861-2868, 2007.

Myburgh et al., "Optimization of Critical Hairpin Features Allows miRNA-based Gene Knockdown Upon Single-copy Transduction," *Molecular Therapy—Nucleic Acids*, 3:e207, 2014.

Osorio et al., "Viral vectors expressing a single microRNA-based short-hairpin RNA result in potent gene silencing in vitro and in vivo," *J. Biotechnol.*, 169:71-81, 2014.

Pardoll, "The blockade of immune checkpoints in cancer immunotherapy," *Nat. Rev. Cancer*, 12(4):252-64, 2012.

PCT International Search Report and Written Opinion issued in International Application No. PCT/IB2019/000328, dated Nov. 5, 2019.

Rousset et al., "Optimizing Synthetic miRNA Minigene Architecture for Efficient miRNA Hairpin Concatenation and Multi-target Gene Knockdown," *Molecular Therapy—Nucleic Acids*, 14:351-363 2018.

Ruby et al., "Intronic microRNA precursors that bypass Drosha processing," *Nature*, 448(7149):83-86, 2007.

Schaefer et al., "Unexpected mutations after CRISPR-Cas9 editing in vivo," *Nat Methods*, 14(6):547-548, 2017.

Seyhan, "A multiplexed miRNA and transgene expression platform for simultaneous repression and expression of protein coding sequences," *Mol. Biosyst.*, 12(1):295-312, 2016.

Sibley et al., "Silencing of Parkinson's disease-associated genes with artificial mirtron mimics of miR-1224," *Nucleic Acids Res.*, 40:9863-9875, 2012.

Stegmeier et al., "A lentiviral microRNA-based system for single-copy polymerase II-regulated RNA interference in mammalian cells," *Proceedings of the National Academy of Sciences of the United States of America*, 102:13212-13217, 2005.

Sullenger and Nair, "From the RNA world to the clinic," *Science*, 352(6295):1417-1420, 2016.

Sun et al., "Multi-miRNA hairpin method that improves gene knockdown efficiency and provides linked multi-gene knockdown," *Biotechniques*, 41:59-63, 2006.

Winter et al., "Many roads to maturity: microRNA biogenesis pathways and their regulation," *Nat. Cell. Biol.*, 11(3):228-234, 2009.

(56) References Cited

OTHER PUBLICATIONS

Yang et al., "Preclinical evaluation of an anti-HCV miRNA cluster for treatment of HCV infection," *Mol. Ther.*, 21(3):588-601, 2013.
English translation of Search Report in Japanese Patent Application No. 20205527, issued Feb. 15, 2023.

\* cited by examiner

Concatenation potency = CP (%)
Knockdown potency = KP (%)

E= Concatenation efficiency with 3 hairpins $CP = (KP)^E$
$E = \ln(CP)/\ln(KP)$

If E=3 concatenation efficiency is 100%
If E=1 concatenation efficiency is 0%

MICRO RNA EXPRESSION CONSTRUCTS AND USES THEREOF

This application is a national phase application under 35 U.S.C. § 371 of International Application No. PCT/IB2019/000328, filed Apr. 1, 2019, which claims the benefit of U.S. Provisional Patent Application No. 62/650,403, filed Mar. 30, 2018 and U.S. Provisional Patent Application No. 62/650,387 filed Mar. 30, 2018, the entirety of each of which is incorporated herein by reference.

INCORPORATION OF SEQUENCE LISTING

The sequence listing that is contained in the file named "UGENP0020US_ST25.txt", which is 20 KB (as measured in Microsoft Windows) and was created on Sep. 28, 2020, is filed herewith by electronic submission and is incorporated by reference herein.

BACKGROUND OF THE INVENTION

1. Field of the Invention

The present invention relates generally to the field of molecular biology. More particularly, it concerns vectors for the expression of miRNAs and the use thereof.

2. Description of Related Art

The discovery and characterization of miRNA (miRNA) genes and their regulatory mechanisms not only provided a novel understanding of physiological regulation of gene expression, but also opened new possibilities for miRNA-based therapeutics. The centerpiece of miRNA genes is a hairpin that ultimately will give rise to a ribonucleoprotein complex which knocks down expression of target genes through identification and destruction of its transcript. Structural elements of the hairpin provide a signal for processing by DROSHA and DICER, leading to formation of a ~20-23 bp mature miRNA duplex (Winter et al., 2009). The functional strand of mature miRNA duplex is incorporated into the RISC complex, which facilitates target mRNA recognition and eventually gene knockdown. Synthetic miRNAs as well as byproducts of the miRNA pathway, such as short hairpin RNAs (shRNAs) and small interfering RNAs (siRNAs) are now commonly used tools in molecular biology. However, the pathway has not lived up to its therapeutic potential (Sullenger and Nair, 2016). siRNAs are most advanced in clinics, however they are short-lived and not suitable for long term gene correction. shRNAs, which bypass DROSHA processing, may overload the cytoplasm with double stranded RNA and hence lead to toxicity by obstructing the natural miRNA pathway (Boudreau et al., 2009; Grimm, 2011). Synthetic miRNAs mimic the natural pathway and should therefore overcome the above limitations (Maczuga et al., 2013), but their use might be limited due to a relatively weak knockdown activity of miRNA, as compared to shRNAs (Boudreau et al., 2008).

Lentiviral vectors can be used to express synthetic miRNA genes since genomic integrations of the transgene and long term expression in recipient cells have to date been shown to be safe in patients (Aiuti, et al., 2013; Biffi et al., 2013). However, further research is needed to optimize knockdown by synthetic miRNA genes to the extent that allows efficient therapeutic correction of pathological gene expression.

The architecture of synthetic miRNA genes, including the tridimensional structure of the hairpin, is of crucial importance for the knockdown efficiency (Myburgh et al., 2014; Fowler et al., 2016). The length of the lower stem is crucial for efficient processing by DROSHA and the relative abundance of mature miRNA strands available, resulting in increased target gene knockdown. However, the architecture of the miRNA gene is not limited to the hairpin structure. Other important elements include promoters and nucleotide sequences not directly linked to the hairpin, referred to as a "spacer". miRNA genes are most of the time driven by polII-dependent promoters which allow tissue specific or/and inducible expression (Lee et al., 2004; Giry-Laterriere et al., 2011; Giry-Laterriere et al., 2011; Liu et al., 2013). The presence of a spacer appears to enhance knockdown efficiency (Stegmeier et al., 2005), however it is not known whether sequence length or other biophysical parameters of the spacer are of importance.

Natural miRNA genes occur in a concatenated form, their architecture consists of an arrangement of several hairpins under the control of a single promoter (Bourhill et al., 2016). Such concatenation may be potentially a powerful tool for biotechnology (Sun et al., 2006). There may be an intervening sequence between the miRNA hairpins which separates them spatially, and may be of any sequence desired.

Adoptive cell therapy (ACT), and in particular the use of T cell receptor (TCR) engineered and chimeric antigen receptor (CAR) T cells, holds great promise for the treatment of various cancers and viral infections. Extremely high cure rates have been reported for certain cancers, specifically hematological malignancies (Jackson et al., 2016), while limited success has been seen with other malignancies, specifically solid tumors (O'Hara, 2016; Han et al., 2017; Irving et al., 2017). Many of these failures are attributed to a hostile tumor microenvironment which provides physical, molecular and immunosuppressive barriers for the engineered immune cells to overcome. Likewise, to date, constructs that can be used for stimulating an immune cell activity, or inhibiting immune checkpoints have not been developed.

SUMMARY OF THE INVENTION

In some embodiments the present disclosure provides a miRNA expression construct comprising a promoter element, a spacer at least 50 nucleotides in length, and a miRNA hairpin. In some aspects, the spacer is between 50 and 1,000 nucleotides in length. In some aspects, the spacer is between 50 and 900; 50 and 800; 100 and 800; 150 and 800; 150 and 750; 200 and 750; 200 and 700; 250 and 700; 250 and 650; 300 and 600; 300 and 550; or 300 and 500 nucleotides in length. In some aspects, the spacer is at least 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 365, 370, or 375 nucleotides in length. In some aspects, the spacer is heterologous with respect to the promoter element. In some aspects, the spacer comprises an encoded open reading frame.

A promoter element in accordance with the embodiments may be a eukaryotic promoter. In some aspects, the eukaryotic promoter is a Pol II or Pol III promoter. In certain aspects, the eukaryotic promoter is a Pol II promoter. In some aspects, the promoter is an inducible, tissue-specific- or cell lineage-specific promoter. In certain aspects, the promoter element is selected from the promoter elements of Table 1. In some aspects, the promoter element is at least 80%, 81%, 82%, 83%, 84%, 85%, 86%, 87%, 88%, 89%, 90%, 91%, 92%, 93%, 94%, 95%, 96%, 97%, 98%, 99%, or 100% identical the EF1α promoter. In some aspects, the EF1α promoter is a splice variant of the EF1α promoter. In some aspects, the splice variant of the EF1α promoter is EF1s. In some aspects, the EF1s promoter has a sequence at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 45. In some aspects, the EF1s promoter has a sequence 100% identical to SEQ ID NO: 45.

A spacer in accordance with the embodiments may be selected from the spacers in Table 9. In some aspects, the spacer is at least 80%, 81%, 82%, 83%, 84%, 85%, 86%, 87%, 88%, 88%, 89%, 90%, 91%, 92%, 93%, 94%, 95%, 96%, 97%, 98%, or 99% identical to SEQ ID NO: 46. In certain aspects, the spacer is 100% identical to SEQ ID NO: 46. In some aspects, the spacer is at least 80%, 81%, 82%, 83%, 84%, 85%, 86%, 87%, 88%, 88%, 89%, 90%, 91%, 92%, 93%, 94%, 95%, 96%, 97%, 98%, or 99% identical to SEQ ID NO: 47. In particular aspects, the spacer is identical to SEQ ID NO: 47. In some aspects, the spacer is at least 80%, 81%, 82%, 83%, 84%, 85%, 86%, 87%, 88%, 88%, 89%, 90%, 91%, 92%, 93%, 94%, 95%, 96%, 97%, 98%, or 99% identical to SEQ ID NO: 48. In particular aspects, the spacer is identical to SEQ ID NO: 48. In some aspects, the spacer is at least 80%, 81%, 82%, 83%, 84%, 85%, 86%, 87%, 88%, 88%, 89%, 90%, 91%, 92%, 93%, 94%, 95%, 96%, 97%, 98%, or 99% identical to SEQ ID NO: 49. In particular aspects, the spacer is identical to SEQ ID NO: 49.

An miRNA hairpin in accordance with the embodiments may comprise, from 5' to 3', and in the order from (a)-(g): (a) a mir-16 flanking sequence comprising the sequence of SEQ ID NO: 25; (b) a first lower stem sequence comprising the mir-16 sequence of SEQ ID NO: 26, SEQ ID NO: 27, SEQ ID NO: 28, SEQ ID NO: 29 or SEQ ID NO: 30; (c) an anti-sense target sequence 22 nucleotides in length; (d) a mir-30 loop sequence comprising the sequence of SEQ ID NO: 31; (e) a sense sequence wherein the sequence is complementary to the sequence of (c) except that the sequence comprises one or two mismatches relative to the sequence of (c), wherein the one or two mismatches comprise: i) a mismatch located at the position 8 to 14 of the sense sequence; or ii) a mismatch at the final 3' position (position 22) of the sense sequence; (f) a second lower stem sequence wherein the sequence is complementary to the sequence of (b); and (g) a second flanking sequence. In some aspects, the sense sequence (e) of the miRNA hairpin comprises one mismatch relative to sequence (c) located at nucleotide position 11 of the sense sequence (e). In some aspects, the sense sequence (e) of the miRNA hairpin comprises two mismatches relative to sequence (c) located (i) at position 11 of the sense sequence (e) and (ii) at the last 3' nucleotide (position 22) of the sense sequence (e). In some aspects, the flanking sequence (g) is not complementary to the mir-16 flanking sequence (a). In certain aspects, the miRNA hairpin sequence is selected from the sequences listed in Table 6. In some aspects, the antisense target sequence is complementary to a CCR5 mRNA sequence. In some aspects, the miRNA expression construct comprises at least 2 repeats of the miRNA hairpin. In some aspects, the at least 2 repeats are separated by an intervening sequence. In some aspects, the miRNA expression construct is DNA. In some aspects, the miRNA expression construct is RNA.

In some embodiments, the present disclosure provides an expression vector comprising a miRNA expression construct comprising a promoter element, a spacer at least 50 nucleotides in length, and a miRNA hairpin. In some aspects, the expression vector comprises 2 or more copies of the miRNA expression construct. In some aspects, the 2 or more copies of the miRNA expression construct form a polycistronic transcript coding sequence. In some aspects, the expression vector is a viral vector. In some aspects, the viral vector is an adenovirus, adeno-associated virus, retrovirus, or lentivirus vector. In further aspects, the expression vector comprises at least one drug resistance marker.

In some embodiments, the present disclosure provides a host cell comprising a miRNA expression construct comprising a promoter element, a spacer at least 50 nucleotides in length, and a miRNA hairpin, or an expression vector comprising the miRNA expression construct.

In some embodiments, the present disclosure provides a method for reducing expression of a gene in a cell comprising expressing a miRNA expression construct comprising a promoter element, a spacer at least 50 nucleotides in length, and a miRNA hairpin, wherein the miRNA hairpin comprises: (a) a mir-16 flanking sequence comprising the sequence of SEQ ID NO: 25; (b) a first lower stem sequence comprising the mir-16 sequence of SEQ ID NO: 26, SEQ ID NO: 27, SEQ ID NO: 28, SEQ ID NO: 29 or SEQ ID NO: 30; (c) an anti-sense target sequence 22 nucleotides in length; (d) a mir-30 loop sequence comprising the sequence of SEQ ID NO: 31; (e) a sense sequence wherein the sequence is complementary to the sequence of (c) except that the sequence comprises one or two mismatches relative to the sequence of (c), wherein the one or two mismatches comprise: i) a mismatch located at the position 8 to 14 of the sense sequence; or ii) a mismatch at the final 3' position (position 22) of the sense sequence; (f) a second lower stem sequence wherein the sequence is complementary to the sequence of (b); and (g) a second flanking sequence; and wherein the anti-sense target sequence (c) is complementary to the sense strand of the gene. In some aspects, expressing the miRNA expression construct in the cell comprises transfecting the cell with a nucleic acid comprising the miRNA expression construct. In some aspects, expressing the miRNA expression construct comprises expressing the miRNA expression construct from an expression vector. In some aspects, the expression vector is an adenovirus, adeno-associated virus, retrovirus or lentivirus vector. In some aspects, the gene to be silenced is CCR5. In some aspects, the cell is a human cell. In some aspects, the method is an in vivo method. In other aspects, the method is an in vitro or ex vivo method. In some aspects, the method further comprises transplanting the cell expressing the miRNA expression construct into an organism. In some aspects, the cell is comprised within an organism.

In some embodiments, the present disclosure provides a recombinant nucleic acid molecule comprising a promoter element, a spacer at least 50 nucleotides in length, and at least one miRNA hairpin, the miRNA hairpin from 5' to 3' comprising in the order from (a)-(g): (a) a mir-16 flanking sequence; (b) a first lower stem sequence comprising a mir-16 sequence; (c) an anti-sense target sequence 22 nucleotides in length; (d) a mir-30 loop sequence; (e) a sense sequence wherein the sequence is complementary to the sequence of (c) except that the sequence comprises one or two mismatches relative to the sequence of (c), wherein the one or two mismatches comprise: i) a mismatch located at the position 8 to 14 of the sense sequence; or ii) a mismatch at the final 3' position (position 22) of the sense sequence; (f) a second lower stem sequence wherein the sequence is complementary to the sequence of (b), wherein the lower stem is at least 11 nucleotides in length; and (g) a second flanking sequence. In some aspects, the lower stem is 11, 12, 13, 14, 15, 16, or 17 nucleotides in length. In some aspects, the first lower stem (b) comprises the mir-16 sequence of SEQ ID NO: 26, SEQ ID NO: 27, SEQ ID NO: 28, SEQ ID NO: 29 or SEQ ID NO: 30. In some aspects, the mir-16 flanking sequence (a) comprises the sequence of SEQ ID NO: 25. In some aspects, the mir-30 loop sequence comprises the sequence of SEQ ID NO: 31. In some aspects, the sense sequence (e) comprises one mismatch relative to sequence (c) located at nucleotide position 11 of the sense sequence (e). In some aspects, the sense sequence (e) comprises two mismatches relative to sequence (c) located (i) at position 11 of the sense sequence (e) and (ii) at the last 3' nucleotide (position 22) of the sense sequence (e). In some aspects, the second flanking sequence (g) is not complementary to the mir-16 flanking sequence (a). In some aspects, the miRNA hairpin sequence is selected from the sequences listed in Table 6. In some aspects, the recombinant nucleic acid molecule comprises at least 2 repeats of the sequences (a)-(g). In some aspects, the at least 2 repeats are separated by an intervening sequence. In some aspects, the anti-sense target sequence is complementary to a CCR5 mRNA sequence. In some aspects, the recombinant nucleic acid molecule is RNA. In some aspects, the recombinant nucleic acid molecule is DNA.

In some embodiments, the present disclosure provides an expression vector comprising a recombinant nucleic acid molecule comprising a promoter element, a spacer at least 50 nucleotides in length, and at least one miRNA hairpin, the miRNA hairpin from 5' to 3' comprising in the order from (a)-(g): (a) a mir-16 flanking sequence; (b) a first lower stem sequence comprising a mir-16 sequence; (c) an anti-sense target sequence 22 nucleotides in length; (d) a mir-30 loop sequence; (e) a sense sequence wherein the sequence is complementary to the sequence of (c) except that the sequence comprises one or two mismatches relative to the sequence of (c), wherein the one or two mismatches comprise: i) a mismatch located at the position 8 to 14 of the sense sequence; or ii) a mismatch at the final 3' position (position 22) of the sense sequence; (f) a second lower stem sequence wherein the sequence is complementary to the sequence of (b), wherein the lower stem is at least 11 nucleotides in length; and (g) a second flanking sequence. In some aspects, the promoter is a eukaryotic promoter. In certain aspects, the eukaryotic promoter is a Pol II or Pol III promoter. In a specific aspect, the eukaryotic promoter is a Pol II promoter. In some aspects, the promoter is an inducible, tissue-specific- or cell lineage-specific promoter. In some aspects, the expression vector comprises 2 or more copies of the recombinant nucleic acid molecule. In some aspects, the 2 or more copies of the recombinant nucleic acid molecule form a polycistronic transcript coding sequence. In some aspects, the expression vector is a viral vector. In certain aspects, the expression vector is an adenovirus, adeno-associated virus, retrovirus, or lentivirus vector. In some aspects, the expression vector further comprises at least one drug resistance marker.

In some embodiments, the present disclosure provides a host cell comprising a recombinant nucleic acid molecule comprising a promoter element, a spacer at least 50 nucleotides in length, and at least one miRNA hairpin, the miRNA hairpin from 5' to 3' comprising in the order from (a)-(g): (a) a mir-16 flanking sequence; (b) a first lower stem sequence comprising a mir-16 sequence; (c) an anti-sense target sequence 22 nucleotides in length; (d) a mir-30 loop sequence; (e) a sense sequence wherein the sequence is complementary to the sequence of (c) except that the sequence comprises one or two mismatches relative to the sequence of (c), wherein the one or two mismatches comprise: i) a mismatch located at the position 8 to 14 of the sense sequence; or ii) a mismatch at the final 3' position (position 22) of the sense sequence; (f) a second lower stem sequence wherein the sequence is complementary to the sequence of (b), wherein the lower stem is at least 11 nucleotides in length; and (g) a second flanking sequence; or an expression vector comprising the recombinant nucleic acid molecule.

In some embodiments, the present disclosure provides a method for reducing expression of a gene in a cell comprising expressing a recombinant nucleic acid molecule comprising a promoter element, a spacer at least 50 nucleotides in length, and at least one miRNA hairpin, the miRNA hairpin from 5' to 3' comprising in the order from (a)-(g): (a) a mir-16 flanking sequence; (b) a first lower stem sequence comprising a mir-16 sequence; (c) an anti-sense target sequence 22 nucleotides in length; (d) a mir-30 loop sequence; (e) a sense sequence wherein the sequence is complementary to the sequence of (c) except that the sequence comprises one or two mismatches relative to the sequence of (c), wherein the one or two mismatches comprise: i) a mismatch located at the position 8 to 14 of the sense sequence; or ii) a mismatch at the final 3' position (position 22) of the sense sequence; (f) a second lower stem sequence wherein the sequence is complementary to the sequence of (b), wherein the lower stem is at least 11 nucleotides in length; and (g) a second flanking sequence in the cell, wherein the anti-sense target sequence (c) is complementary to the sense strand of the gene. In some aspects, expressing the nucleic acid molecule in the cell comprises transfecting the cell with the recombinant nucleic acid. In some aspects, expressing the recombinant nucleic acid molecule in the cell comprises expressing the nucleic acid molecule from an expression vector. In some aspects, the expression vector is a viral vector. In specific aspects, the expression vector is an adenovirus, adeno-associated virus, retrovirus, or lentivirus vector. In some aspects, the gene is CCR5. In some aspects, the cell is a human cell. In some aspects, the method is further defined as an in vivo method. In other aspects, the method is defined as an in vitro or ex vivo method. In some aspects, the method further comprises transplanting the cell expressing the recombinant nucleic acid molecule into an organism. In some aspects, the cell is comprised within an organism.

In some embodiments, the present disclosure provides a miRNA expression construct comprising a promoter sequence and at least two miRNA hairpins wherein said at least two miRNA hairpins are targeted to transcripts of immune checkpoint genes. In some aspects, the at least two miRNA hairpins target different sequences. In some aspects, the at least two miRNA hairpins target different sequences of transcripts of the same gene. In another aspect, the miRNA hairpins are targeted to different transcripts. In some aspects, the miRNA hairpins are targeted to transcripts of different genes. In some aspects, the at least two miRNA hairpins are targeted to transcripts of at least one immune checkpoint gene selected from the group consisting of: PD1, CTLA4, LAG3, TIM3, TIGIT, CD96, BTLA, KIRs, adenosine A2a receptor, Vista, IDO, FAS, SIRP alpha, CISH, SHP-1, FOXP3, LAIR1, PVRIG, PPP2CA, PPP2CB, PTPN6, PTPN22, CD160, CRTAM, SIGLEC7, SIGLEC9, CD244, TNFRSF10B, TNFRSF10A, CASP8, CASP10, CASP3, CASP6, CASP7, FADD, TGFBRII, TGFBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, PRDM1, BATF, GUCY1A2, GUCY1A3, GUCY1B2, and GUCY1B3.

A miRNA expression construct in accordance with the embodiments may comprise at least three miRNA hairpins. In some aspects, the at least three miRNA hairpins are each different. In some aspects, the at least three different miRNA hairpins are targeted to transcripts of at least one immune checkpoint gene. In some aspects, the at least three different miRNA hairpins are targeted to three different immune checkpoint genes. In some aspects, the miRNA expression construct comprises at least 4, 5, 6, 7, 8, 9 or 10 miRNA hairpins. In some aspects, the at least 4, 5, 6, 7, 8, 9 or 10 miRNA hairpins are each different. In some aspects, the at least 4, 5, 6, 7, 8, 9 or 10 miRNA hairpins are targeted to transcripts of 2, 3, 4 or 5 different immune checkpoint genes.

In some embodiments, the miRNA expression construct may comprise a spacer sequence positioned between the promoter and the at least two miRNA hairpins. In some aspects, the spacer is between 50 and 1,000 nucleotides in length.

In some aspects, the promoter sequence of the miRNA expression construct is at least 80% identical to the EF1s promoter sequence. In some aspects, the promoter sequence is at least 81%, 82%, 83%, 84%, 85%, 86%, 87%, 88%, 89%, 90%, 91%, 92%, 93%, 94%, 95%, 96%, 97%, 98%, or 99% identical to the EF1s promoter sequence. In some aspects, the promoter sequence is identical to the EF1s promoter sequence.

In some aspects, the promoter sequence of the miRNA expression construct is at least 80% identical to the UBI promoter sequence. In some aspects, the promoter sequence is at least 81%, 82%, 83%, 84%, 85%, 86%, 87%, 88%, 89%, 90%, 91%, 92%, 93%, 94%, 95%, 96%, 97%, 98%, or 99% identical to the UBI promoter sequence. In some aspects, the promoter sequence is identical to the UBI promoter sequence.

A miRNA expression construct in accordance with the embodiments may further comprise a receptor sequence. In some aspects, the receptor sequence is a chimeric antigen receptor. In some aspects, the receptor sequence is a T cell receptor sequence.

A miRNA expression construct in accordance with the embodiments may further comprise a selective marker. In some aspects, the selective marker is a selection gene. In some aspects, the selection gene is LNGFR or a derivative thereof. In some aspects, the miRNA expression construct further comprises a suicide gene. For example, the suicide gene can be herpes simplex virus thymidine kinase (HSV-tk), inducible caspase 9 (iCasp9), truncated endothelial growth factor receptor (tEGFR), RQR8, dihydrofolate reductase (DHFR), or thymidylate synthase (TYMS).

A miRNA expression construct in accordance with the embodiments may comprise a peptide cleavage site. In some aspects, the peptide cleavage site is a 2A peptide. In some aspects, the 2A peptide is selected from the group comprising: 2A, P2A, T2A, E2A, F2A, BmCPV 2A, and BmIFV 2A. In specific aspects, the 2A peptide is T2A.

In some embodiments, the present disclosure provides a vector comprising a miRNA expression construct comprising a promoter sequence and at least two miRNA hairpins wherein said at least two miRNA hairpins are targeted to transcripts of immune checkpoint genes. In some aspects, the vector is a viral vector. In some aspects, the viral vector is an adenovirus, adeno-associated virus, retrovirus, or lentiviral vector.

In some embodiments, the present disclosure provides a mammalian cell comprising a miRNA expression construct comprising a promoter sequence and at least two miRNA hairpins wherein said at least two miRNA hairpins are targeted to transcripts of immune checkpoint genes, or a vector comprising said miRNA expression construct. In some aspects, the mammalian cell is an immune effector cell. In some aspects, the immune effector cell is selected from the group comprising: T cells, TILS, TCR-engineered T cells, CAR T cells, NK cells, NK/T cells, and T regulatory cells.

In some embodiments, there is provided a method for preparing engineered immune effector cells comprising transfecting or transducing the immune effector cells with the miRNA expression construct in accordance with the embodiments or transducing the immune effector cells with a vector comprising an miRNA expression construct in accordance with the embodiments. In some aspects, the method for preparing engineered immune effector cells comprises transfecting or transducing a chimeric antigen receptor sequence or T cell receptor sequence into immune effector cells and then transfecting or transducing the miRNA expression construct of the embodiments or the vector comprising a miRNA expression construct of the embodiments into the cells.

In some embodiments, there is provided a method for preparing engineered immune effector cells from a patient. In some aspects, the method for preparing engineered immune effector cells from a patient comprises: (a) collecting immune effector cells from the patient; and (b) transfecting the immune effector cells with a miRNA expression construct of the embodiments or transducing the immune effector cells with a vector comprising a miRNA expression construct to generate engineered immune effector cells. In some aspects, the method for preparing engineered immune cells from a patient comprises: (a) collecting immune effector cells from the patient; (b) transducing or transfecting the immune effector cells with a chimeric antigen receptor or T cell receptor to generate a modified immune effector cells; and (c) transducing or transfecting the modified immune effector cells with a miRNA expression construct in accordance with the embodiments, or a vector comprising a miRNA expression construct in accordance with the embodiments, to generate engineered immune effector cells. In still further aspects, an immune effector cell of the embodiments is a T cell, a NK cell or a NK/T cell. In some aspects, the immune effector cell further expresses an recombinant T cell receptor or a chimeric antigen receptor (CAR).

In some embodiments, there is provided a method for treating a patient in need thereof, comprising introducing engineered immune effector cells in accordance with the embodiments into the patient. For example, in some aspects, the patient is a patient with cancer.

In a further embodiment there is provided an immune effector cell comprising one or more miRNA expression constructs that target a CCR5 and an immune checkpoint inhibitor gene. For example, the checkpoint inhibitor gene can be PD1, CTLA4, LAG3, TIM3, TIGIT, CD96, BTLA, KIRs, adenosine A2a receptor, ARG2 (arginase 2), Vista, IDO, FAS, SIRP alpha, CISH, SHP-1, FOXP3, LAIR1, PVRIG, PPP2CA, PPP2CB, PTPN6, PTPN22, CD160, CRTAM, SIGLEC7, SIGLEC9, CD244, TNFRSF10B, TNFRSF10A, CASP8, CASP10, CASP3, CASP6, CASP7, FADD, TGFBRII, TGFBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, PRDM1, BATF, GUCY1A2, GUCY1A3, GUCY1B2, or GUCY1B3. In some aspects, the checkpoint inhibitor gene is PD1. In some aspects, the PD1 target sequence is SEQ ID NO: 59, 60 or 61, preferably SEQ ID NO: 59. In some aspects, the immune effector cell is selected from the group consisting of: T cells, TILS, TCR-engineered T cells, CAR T cells, NK cells, NK/T cells, T regulatory cells, monocytes and macrophages. For instance, the cell can be a T cell, such as a CAR T-cell. In some aspects, the cell comprises a CAR that targeted HIV infected cells. In further aspects, a cell comprises one or more miRNA expression constructs that target a CCR5 and at least two immune checkpoint inhibitor genes. Thus, a cell can comprise any of the miRNA expression constructs of the embodiments.

In still a further embodiment there is provided an expression construct comprising a miRNA sequence that target a CCR5 and an immune checkpoint inhibitor gene. For example, the miRNA sequence can be a sequence in accordance with any of the embodiments described herein. In some aspects, the construct further comprises a CAR expression sequence, such as a CAR sequence that targets HIV infected cells.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is preferably below 0.01%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. The Present Embodiments

Figure 1:
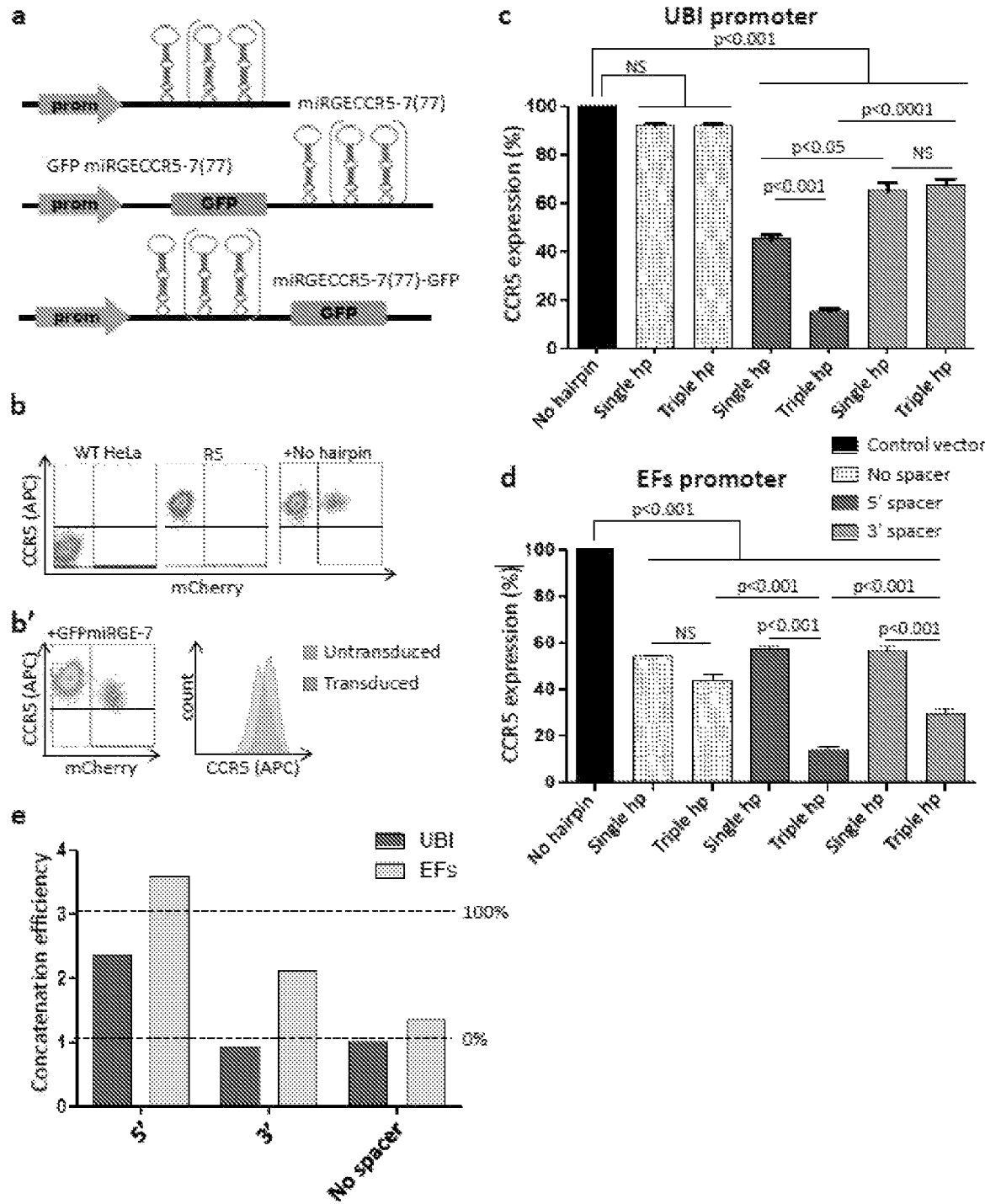
FIG. 1: A spacer sequence is required for polymerase II promoter driven miRNA knock down. (a) Schematic representation of the miRGE-based used in this experiment. All hairpins were designed to target CCR5. Two different pol II dependent promoters (Ubiquitin C and Elongation Factor 1 short) drive miRGE expression (single or triple hairpin) with or without the GFP sequence as spacer. The position of the spacer, either in 5' or in 3' of the promoter was also investigated. (b) Constructs expressed with a Ubiquitin C promoter or Elongation Factor 1 short promoter were transduced at 0.2 multiplicity of infection (MOI) in HeLa cells expressing CCR5. Flow cytometry determination of CCR5 expression in the transduced population (mCherry+) versus the untransduced population (mCherry−): WT HeLa cells (double negative), HeLa R5 cells (CCR5 positive). R5+Ctrl mCherry vector; R5+single mirGE hairpin) with GFP spacer. (b') Mean APC fluorescence values in the transduced (red) and untransduced (blue) populations were used to calculate the miRNA-mediated CCR5 knock-down. (c) Bar graph showing the relative expression of CCR5 with the UBI promoter constructs. (d) Histogram showing the relative expression of CCR5 with the EF1 short promoter constructs. (e) Concatenation efficiency (E) of the different constructs as calculated on the bar graph. If E=1 absence of additive effect is observed with the concatemerized hairpins (efficiency is 0%). If E=3 perfect additive effect of the hairpin is observed in the concatenate (efficiency is 100%). Data represent the mean+/− SEM of three independent experiments.

The present invention relates generally to miRNA expression constructs. The present invention relates to constructs for the expression of multiple miRNAs. The present invention further relates to the use of a spacer sequence between the promoter and the miRNA sequences. In some aspects, the spacer sequence may be from GFP.

II. RNA Inhibition

An inhibitory nucleic acid may inhibit the transcription of a gene or prevent the translation of a gene transcript in a cell. An inhibitory nucleic acid may be from 16 to 1000 nucleotides long, and in certain embodiments from 18 to 100 nucleotides long. In certain embodiments, the inhibitory nucleic acid is an isolated nucleic acid that binds or hybridizes to a gene of interest.

Inhibitory nucleic acids are well known in the art. For example, siRNA, shRNA and double-stranded RNA have been described in U.S. Pat. Nos. 6,506,559 and 6,573,099, as well as in U.S. Patent Publications 2003/0051263, 2003/0055020, 2004/0265839, 2002/0168707, 2003/0159161, and 2004/0064842, all of which are herein incorporated by reference in their entirety.

Since the discovery of RNAi by Fire and colleagues in 1998, the biochemical mechanisms have been rapidly characterized. Double stranded RNA (dsRNA) is cleaved by Dicer, which is an RNAase III family ribonuclease. This process yields miRNAs of ~21 nucleotides in length. These miRNAs are incorporated into a multiprotein RNA-induced silencing complex (RISC) that is guided to target mRNA. RISC cleaves the target mRNA in the middle of the complementary region. In mammalian cells, the related miRNAs are found that are short RNA fragments (~22 nucleotides). miRNAs are generated after Dicer-mediated cleavage of longer (~70 nucleotide) precursors with imperfect hairpin RNA structures. The miRNA is incorporated into a miRNA-protein complex (miRNP), which leads to translational repression of target mRNA.

In designing RNAi there are several factors that need to be considered such as the nature of the siRNA, the durability of the silencing effect, and the choice of delivery system. To produce an RNAi effect, the miRNA that is introduced into the organism will typically contain exonic sequences. Furthermore, the RNAi process is homology dependent, so the sequences must be carefully selected so as to maximize gene specificity, while minimizing the possibility of cross-interference between homologous, but not gene-specific sequences. Particularly the miRNA exhibits greater than 80, 85, 90, 95, 98% or even 100% identity between the sequence of the miRNA and a portion of the nucleotide sequence of a target gene. Sequences less than about 80% identical to the target gene are substantially less effective. Thus, the greater identity between the miRNA and the target gene to be inhibited, the less likely expression of unrelated genes will be affected.

In addition, the size of the miRNA is an important consideration. In some embodiments, the present invention relates to miRNA molecules that include at least about 19-25 nucleotides, and are able to modulate target gene expression. In the context of the present invention, the miRNA is particularly less than 500, 200, 100, 50, 25, 24, 23 or 22 nucleotides in length. In some embodiments, the miRNA is from about 25 nucleotides to about 35 nucleotides or from about 19 nucleotides to about 25 nucleotides in length.

To improve the effectiveness of miRNA-mediated gene silencing, guidelines for selection of target sites on mRNA have been developed for optimal design of miRNA (Soutschek et al., 2004; Wadhwa et al., 2004). These strategies may allow for rational approaches for selecting siRNA sequences to achieve maximal gene knockdown. To facilitate the entry of miRNA into cells and tissues, a variety of vectors including plasmids and viral vectors such as adenovirus, lentivirus, and retrovirus have been used (Wadhwa et al., 2004).

Within an inhibitory nucleic acid, the components of a nucleic acid need not be of the same type or homogenous throughout (e.g., an inhibitory nucleic acid may comprise a nucleotide and a nucleic acid or nucleotide analog). Typically, an inhibitory nucleic acid form a double-stranded structure; the double-stranded structure may result from two separate nucleic acids that are partially or completely complementary. In certain embodiments of the present invention, the inhibitory nucleic acid may comprise only a single nucleic acid (polynucleotide) or nucleic acid analog and form a double-stranded structure by complementing with itself (e.g., forming a hairpin loop). The double-stranded structure of the inhibitory nucleic acid may comprise 16-500 or more contiguous nucleobases, including all ranges therebetween. The inhibitory nucleic acid may comprise 17 to 35 contiguous nucleobases, more particularly 18 to 30 contiguous nucleobases, more particularly 19 to 25 nucleobases, more particularly 20 to 23 contiguous nucleobases, or 20 to 22 contiguous nucleobases, or 21 contiguous nucleobases that hybridize with a complementary nucleic acid (which may be another part of the same nucleic acid or a separate complementary nucleic acid) to form a double-stranded structure.

miRNA can be obtained from commercial sources, natural sources, or can be synthesized using any of a number of techniques well-known to those of ordinary skill in the art. For example, commercial sources of predesigned miRNA include Invitrogen's Stealth™ Select technology (Carlsbad, Calif.), Ambion® (Austin, Tex.), and Qiagen® (Valencia, Calif.). An inhibitory nucleic acid that can be applied in the compositions and methods of the present invention may be any nucleic acid sequence that has been found by any source to be a validated downregulator of a target gene.

In some embodiments, the miRNA molecule is at least 75, 80, 85, or 90% homologous, particularly at least 95%, 99%, or 100% similar or identical, or any percentages in between the foregoing (e.g., the invention contemplates 75% and greater, 80% and greater, 85% and greater, and so on, and said ranges are intended to include all whole numbers in between), to at least 10 contiguous nucleotides of any of the nucleic acid sequences encoding a full-length protein.

The miRNA may also comprise an alteration of one or more nucleotides. Such alterations can include the addition of non-nucleotide material, such as to the end(s) of the 19 to 25 nucleotide RNA or internally (at one or more nucleotides of the RNA). In certain aspects, the RNA molecule contains a 3'-hydroxyl group. Nucleotides in the RNA molecules of the present invention can also comprise non-standard nucleotides, including non-naturally occurring nucleotides or deoxyribonucleotides. The double-stranded oligonucleotide may contain a modified backbone, for example, phosphorothioate, phosphorodithioate, or other modified backbones known in the art, or may contain non-natural internucleoside linkages. Additional modifications of siRNAs (e.g., 2'-O-methyl ribonucleotides, 2'-deoxy-2'-fluoro ribonucleotides, "universal base" nucleotides, 5-C-methyl nucleotides, one or more phosphorothioate internucleotide linkages, and inverted deoxyabasic residue incorporation) can be found in U.S. Publication 2004/0019001 and U.S. Pat. No. 6,673,611 (each of which is incorporated by reference in its entirety). Collectively, all such altered nucleic acids or RNAs described above are referred to as modified miRNAs.

II. Vectors for Cloning, Gene Transfer and Expression

Within certain aspects expression vectors are employed to express a nucleic acid of interest, such as a nucleic acid that inhibits the expression of a particular gene. Expression requires that appropriate signals be provided in the vectors, and which include various regulatory elements, such as enhancers/promoters from both viral and mammalian sources that drive expression of the genes of interest in host cells. Elements designed to optimize RNA stability in host cells also are defined. The conditions for the use of a number of dominant drug selection markers for establishing permanent, stable cell clones expressing the products are also provided, as is an element that links expression of the drug selection markers to expression of the polypeptide.

A. Regulatory Elements

Throughout this application, the term "expression construct" or "expression vector" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest i.e., as is the case with RNA molecules of the embodiments.

In certain embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for eukaryotic RNA polymerase (Pol) I, II or III. Much of the thinking about how promoters are organized derives from analyses of several viral Pol II promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In some embodiments, the promoter comprises an Elongation Factor 1 short (EF1s) promoter. In other embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 1 and 2 list several regulatory elements that may be employed, in the context of the present invention, to regulate the expression of the gene of interest. This list is not intended to be exhaustive of all the possible elements involved in the promotion of gene expression but, merely, to be exemplary thereof. In some aspects, a promoter for use according to the instant embodiments is a non-tissue specific promoter, such as a constitutive promoter.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene or miRNA of interest in an expression construct (Table 1 and Table 2). Additionally, any promoter/enhancer combination (as per the Eukaryotic Promoter Data Base EPDB) could also be used to drive expression of the gene or miRNA of interest. Truncated promoters may also be used to drive expression. Eukaryotic cells can support cytoplasmic transcription from certain bacterial promoters if the appropriate bacterial polymerase is provided, either as part of the delivery complex or as an additional genetic expression construct.

TABLE 1

Promoter and/or Enhancer

| Promoter/Enhancer | References |
| --- | --- |
| Elongation Factor 1 alpha (EF1α) | Kim et al., 1990 |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| α$_1$-Antitrypain | Latimer et al., 1990 |
| H2B (TH2B) Histone | Hwang et al., 1990 |
| Mouse and/or Type I Collagen | Ripe et al., 1989 |

TABLE 1-continued

Promoter and/or Enhancer

| Promoter/Enhancer | References |
|---|---|
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985; Sakai et aL , 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

Where any cDNA insert is employed, one will typically include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. In some aspects, however, a polyadenylation signal sequence is not included in a vector of the embodiments. For example, incorporation of such a signal sequence in lentiviral vectors (before a 3' LTR) can reduce resulting lentiviral titers.

A spacer sequence may be included in the nucleic acid construct. The presence of a spacer appears to enhance knockdown efficiency of miRNA (Stegmeier et al., 2005). Spacers may be any nucleotide sequence. In some aspects, the spacer is GFP.

Also contemplated as an element of the expression cassette is a terminator. These elements can serve to enhance message levels and to minimize read through from the cassette into other sequences.

B. Selectable Markers

In certain embodiments of the invention, the cells contain nucleic acid constructs of the present invention, a cell may be identified in vitro, ex vivo or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

III. Delivery of Nucleic Acid Molecules and Expression Vectors

In certain aspects, vectors for delivery of nucleic acids of the embodiments could be constructed to express these factors in cells. In a particular aspect, the following systems and methods may be used in delivery of nucleic acids to desired cell types.

A. Homologous Recombination

In certain aspects of the embodiments, the vectors encoding nucleic acid molecules of the embodiments may be introduced into cells in a specific manner, for example, via homologous recombination. Current approaches to express genes in stem cells have involved the use of viral vectors (e.g., lentiviral vectors) or transgenes that integrate randomly in the genome. These approaches have not been successful due in part because the randomly integrated vectors can activate or suppress endogenous gene expression, and/or the silencing of transgene expression. The problems associated with random integration could be partially overcome by homologous recombination to a specific locus in the target genome.

Homologous recombination (HR), also known as general recombination, is a type of genetic recombination used in all forms of life in which nucleotide sequences are exchanged between two similar or identical strands of DNA. The technique has been the standard method for genome engineering in mammalian cells since the mid 1980s. The process involves several steps of physical breaking and the eventual rejoining of DNA. This process is most widely used in nature to repair potentially lethal double-strand breaks in DNA. In addition, homologous recombination produces new combinations of DNA sequences during meiosis, the process by which eukaryotes make germ cells like sperm and ova. These new combinations of DNA represent genetic variation in offspring which allow populations to evolutionarily adapt to changing environmental conditions over time. Homologous recombination is also used in horizontal gene transfer to exchange genetic material between different strains and species of bacteria and viruses. Homologous recombination is also used as a technique in molecular biology for introducing genetic changes into target organisms.

Homologous recombination can be used as targeted genome modification. The efficiency of standard HR in mammalian cells is only $10^{-6}$ to $10^{-9}$ of cells treated (Capecchi, 1990). The use of meganucleases, or homing endonucleases, such as I-SceI have been used to increase the efficiency of HR. Both natural meganucleases as well as engineered meganucleases with modified targeting specificities have been utilized to increase HR efficiency (Pingoud and Silva, 2007; Chevalier et al., 2002). Another path toward increasing the efficiency of HR has been to engineer chimeric endonucleases with programmable DNA specificity domains (Silva et al., 2011). Zinc-finger nucleases (ZFN) are one example of such a chimeric molecule in which Zinc-finger DNA binding domains are fused with the catalytic domain of a Type IIS restriction endonuclease such as FokI (as reviewed in Durai et al., 2005; PCT/US2004/030606). Another class of such specificity molecules includes Transcription Activator Like Effector (TALE) DNA binding domains fused to the catalytic domain of a Type IIS restriction endonuclease such as FokI (Miller et al., 2011: PCT/IB2010/000154).

B. Nucleic Acid Delivery Systems

One of skill in the art would be well equipped to construct a vector through standard recombinant techniques (see, for example, Sambrook et al., 2001 and Ausubel et al., 1996, both incorporated herein by reference). Vectors include but are not limited to, plasmids, cosmids, viruses (bacteriophage, animal viruses, and plant viruses), and artificial chromosomes (e.g., YACs), such as retroviral vectors (e.g., derived from Moloney murine leukemia virus vectors (MoMLV), MSCV, SFFV, MPSV, SNV etc), lentiviral vectors (e.g., derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, Rous sarcoma virus vectors.

1. Episomal Vectors

The use of plasmid- or liposome-based extra-chromosomal (i.e., episomal) vectors may be also provided in certain aspects of the invention, for example, for reprogramming of somatic cells. Such episomal vectors may include, e.g., oriP-based vectors, and/or vectors encoding a derivative of EBV-protein EBNA-1. These vectors may permit large fragments of DNA to be introduced to a cell and maintained extra-chromosomally, replicated once per cell cycle, partitioned to daughter cells efficiently, and elicit substantially no immune response.

In particular, EBNA-1, the only viral protein required for the replication of the oriP-based expression vector, does not elicit a cellular immune response because it has developed an efficient mechanism to bypass the processing required for presentation of its antigens on MHC class I molecules (Levitskaya et al., 1997). Further, EBNA-1 can act in trans to enhance expression of the cloned gene, inducing expression of a cloned gene up to 100-fold in some cell lines (Langle-Rouault et al., 1998; Evans et al., 1997). Finally, the manufacture of such oriP-based expression vectors is inexpensive.

Other extra-chromosomal vectors include other lymphotrophic herpes virus-based vectors. Lymphotrophic herpes virus is a herpes virus that replicates in a lymphoblast (e.g., a human B lymphoblast) and becomes a plasmid for a part of its natural life-cycle. Herpes simplex virus (HSV) is not a "lymphotrophic" herpes virus. Exemplary lymphotrophic herpes viruses include, but are not limited to EBV, Kaposi's sarcoma herpes virus (KSHV); Herpes virus saimiri (HS)

and Marek's disease virus (MDV). Also other sources of episome-based vectors are contemplated, such as yeast ARS, adenovirus, SV40, or BPV.

One of skill in the art would be well equipped to construct a vector through standard recombinant techniques (see, for example, Maniatis et al., 1988 and Ausubel et al., 1994, both incorporated herein by reference).

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide.

Such components also might include markers, such as detectable and/or selection markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

2. Transposon-Based System

According to a particular embodiment the introduction of nucleic acids may use a transposon-transposase system. The used transposon-transposase system could be the well known Sleeping Beauty, the Frog Prince transposon-transposase system (for the description of the latter see e.g., EP1507865), or the TTAA-specific transposon piggyback system.

Transposons are sequences of DNA that can move around to different positions within the genome of a single cell, a process called transposition. In the process, they can cause mutations and change the amount of DNA in the genome. Transposons were also once called jumping genes, and are examples of mobile genetic elements.

There are a variety of mobile genetic elements, and they can be grouped based on their mechanism of transposition. Class I mobile genetic elements, or retrotransposons, copy themselves by first being transcribed to RNA, then reverse transcribed back to DNA by reverse transcriptase, and then being inserted at another position in the genome. Class II mobile genetic elements move directly from one position to another using a transposase to "cut and paste" them within the genome.

3. Viral Vectors

In generating recombinant viral vectors, non-essential genes are typically replaced with a gene or coding sequence for a heterologous (or non-native) protein or nucleic acid. Viral vectors are a kind of expression construct that utilizes viral sequences to introduce nucleic acid and possibly proteins into a cell. The ability of certain viruses to infect cells or enter cells via pH-dependent or pH-independent mechanisms, to integrate their genetic cargo into a host cell genome and to express viral genes stably and efficiently have made them attractive candidates for the transfer of foreign nucleic acids into cells (e.g., mammalian cells). Non-limiting examples of virus vectors that may be used to deliver a nucleic acid of certain aspects of the present invention are described below.

Retroviruses have promise as gene delivery vectors due to their ability to integrate their genes into the host genome, transferring a large amount of foreign genetic material, infecting a broad spectrum of species and cell types and of being packaged in special cell-lines (Miller, 1992).

In order to construct a retroviral vector, a nucleic acid is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid (i.e., the vector genome) to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Depending on the tropism of the envelope protein used to cover the vector particles surface, retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; Giry-Laterriere et al., 2011; U.S. Pat. Nos. 6,013,516 and 5,994,136).

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference.

C. Nucleic Acid Delivery

Introduction of a nucleic acid, such as DNA or RNA, into cells to be programmed with the current invention may use any suitable methods for nucleic acid delivery for transformation of a cell, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

1. Liposome-Mediated Transfection

In a certain embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen). The amount of liposomes used may vary upon the nature of the liposome as well as the cell used, for example, about 5 to about 20 μg vector DNA per 1 to 10 million of cells may be contemplated.

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

2. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. Recipient cells can be made more susceptible to transformation by mechanical wounding. Also the amount of vectors used may vary upon the nature of the cells used, for example, about 5 to about 20 g vector DNA per 1 to 10 million of cells may be contemplated.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

3. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

4. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

D. Cell Culturing

Generally, cells of the present invention are cultured in a culture medium, which is a nutrient-rich buffered solution capable of sustaining cell growth.

Culture media suitable for isolating, expanding and differentiating stem cells according to the method described herein include but not limited to high glucose Dulbecco's Modified Eagle's Medium (DMEM), DMEM/F-12, Liebovitz L-15, RPMI 1640, Iscove's modified Dubelcco's media (IMDM), and Opti-MEM SFM (Invitrogen Inc.). Chemically Defined Medium comprises a minimum essential medium such as Iscove's Modified Dulbecco's Medium (IMDM) (Gibco), supplemented with human serum albumin, human Ex Cyte lipoprotein, transferrin, insulin, vitamins, essential and non essential amino acids, sodium pyruvate, glutamine and a mitogen is also suitable. As used herein, a mitogen refers to an agent that stimulates cell division of a cell. An agent can be a chemical, usually some form of a protein that encourages a cell to commence cell division, triggering mitosis. In one embodiment, serum free media such as those described in U.S. Ser. No. 08/464,599 and WO96/39487, and the "complete media" as described in U.S. Pat. No. 5,486,359 are contemplated for use with the method described herein. In some embodiments, the culture medium is supplemented with 10% Fetal Bovine Serum (FBS), human autologous serum, human AB serum or platelet rich plasma supplemented with heparin (2U/ml). Cell cultures may be maintained in a $CO_2$ atmosphere, e.g., 5% to 12%, to maintain pH of the culture fluid, incubated at 37° C. in a humid atmosphere and passaged to maintain a confluence below 85%.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Construction of miRNA-containing plasmids and lentiviral vectors. The plasmids were constructed using the gateway system as described previously (Myburgh et al., 2014). With the exception of MGST2, spacer sequences were amplified by PCR using Herculase II polymerase (Agilent, Santa Clara, Calif.) with forward and reverse primers carrying respectively EcoRI and XhoI restriction sites and cloned into a pENTR vector (Invitrogen) by digestion/ ligation steps (Table 3). Most of the primers used for the cloning of spacers were designed with AttB1 (forward primer) and AttB2 (reverse primer) recombination sites at the 5' extremity (Table 4).

The MGST2 spacer was obtained from pOTB7-MGST2 plasmid (transomic) by EcoRI/XhoI restriction digestion and subsequent ligation into the pENTR vector. mirGE hairpins were amplified using the same strategy and forward and reverse primers carrying respectively SpeI and BamHI restriction sites. Elements of the miRGE hairpins can be seen in Table 5. miRGE hairpin concatenates were made using different couples of restriction enzymes on the miRGE primers or by blunt ligation as in Sun et al, 2006. Each new miRGE addition was verified by sequencing the pENTR vector. The amplicon parts of each clone, including spacer and miRGE hairpins were systematically verified by sequencing. The oligos for the miRGE PCR template and primers were obtained from Microsynth (Balgach, Switzerland). miRGE hairpin template sequences targeting CCR5, GFP and p22$^{phox}$ are available in Table 6.

The final lentivector plasmid was generated by an LR Clonase II (Invitrogen, Carlsbad, Calif.)-mediated recombination of a pENTR plasmid containing the human UBI promoter (pENTR-L4-UBI-L1R) or the Elongation Factor 1 short promoter (pENTR-L4-EFs-L1R) and a lentivector destination cassette (pCWX-R4dEST-R2-PC) containing an additional transcription unit encoding for mCherry marker gene upon human phosphoglycerate kinase 1 (PGK) promoter. The GFP target sequence-AAGAACGGCAT-CAAGGTGAACT (SEQ ID NO:57)—was taken from a previous publication (Mottet-Osman et al., 2007). The human CCR5 (Genbank NM_000579.3) target sequences (T7) 5'aAGTGTCAAGTCCAATCTATGA (SEQ ID NO:58) was previously used (Myburgh et al., 2014).

TABLE 3

Lentivectors and titers.

| Lentivector | Titer (TU/mL) |
|---|---|
| pCWX-UBI-mcherry (control vector) | 3.55E+06 |
| pCWX-UBI-No spacer-mirGE CCR5-7-PGK-mCherry | 1.02E+07 |
| pCWX-UBI-GFP-mirGE CCR5-7-PGK-mCherry | 4.66E+06 |
| pCWX-UBI-mirGE CCR5-7-GFP-PGK-mCherry | 1.17E+07 |
| pCWX-UBI-MGST2-miRGE CCR5-7-PGK-mCherry | 7.80E+05 |
| pCWX-UBI-NGFR-miRGE CCR5-7-PGK-mCherry | 1.94E+05 |
| pCWX-UBI-CD4 R1-miRGE CCR5-7-PGK-mCherry | 1.80E+06 |
| pCWX-UBI-CD4 R2-miRGE CCR5-7-PGK-mCherry | 2.76E+06 |
| pCWX-UBI-CD4 R3-miRGE CCR5-7-PGK-mCherry | 2.52E+06 |
| pCWX-UBI-HO-1-miRGE CCR5-7-PGK-mCherry | 1.60E+06 |
| pCWX-UBI-H2B-miRGE CCR5-7-PGK-mCherry | 1.22E+07 |
| pCWX-UBI-stopGFP-miRGE CCR5-7-PGK-mCherry | 3.54E+06 |
| pCWX-UBI-GFPpart1-miRGE CCR5-7-PGK-mCherry | 1.56E+06 |
| pCWX-UBI-GFPpart2-miRGE CCR5-7-PGK-mCherry | 1.59E+06 |
| pCWX-UBI-MGST2-miRGE CYBA 222-PGK-mCherry | 1.57E+06 |
| pCWX-UBI-stopGFP-miRGE CYBA 222-PGK-mCherry | 2.31E+06 |
| pCWX-UBI- MGST2-mirGE-CCR5-777-PGK-mCherry | 1.34E+07 |
| pCWX-UBI- MGST2-mirGE-CCR5-777GFP-PGK-mCherry | 1.20E+07 |
| pCWX-UBI- MGST2-mirGE-CCR5-7777-PGK-mCherry | 1.10E+05 |
| pCWX-UBI- MGST2-mirGE-CCR5-7777GFP-PGK-mCherry | 1.28E+07 |
| pCWX-UBI-No spacer-mirGE CCR5-777-PGK-mCherry | 6.81E+06 |
| pCWX-UBI-mirGE CCR5-777-GFP-PGK-mCherry | 1.10E+07 |
| pCWX-UBI-H2B-miRGE CCR5-777-PGK-mCherry | 5.06E+06 |
| pCWX-UBI- stopGFP-mirGE-CCR5-777-PGK-mCherry | 1.00E+06 |
| pCWX-UBI- stopGFP-mirGE-CCR5-777GFP-PGK-mCherry | 1.84E+05 |
| pCWX-UBI- stopGFP-mirGE-CCR5-7777-PGK-mCherry | 1.98E+06 |
| pCWX-UBI- stopGFP-mirGE-CCR5-7777GFP-PGK-mCherry | 1.12E+06 |
| pCWX-UBI-stopGFP-miRGEGFP-PGK-mCherry | 9.02E+05 |
| pCWX-EFs-No spacer-mirGE CCR5-7-PGK-mCherry | 9.25E+06 |
| pCWX-EFs-GFP-mirGE CCR5-7-PGK-mCherry | 1.21E+07 |
| pCWX-EFs-GFP-mirGE CCR5-777-PGK-mCherry | 1.27E+07 |
| pCWX-EFs-mirGE CCR5-7-GFP-PGK-mCherry | 6.82E+06 |
| pCWX-EFs-mirGE CCR5-777-GFP-PGK-mCherry | 4.75E+06 |
| pCWX-EFs-No spacer-mirGE CCR5-777-PGK-mCherry | 6.02E+06 |

TABLE 4

Cloning primers

| Amplicon | Primer forward 5'-3' (AttB1-EcoRI) | Primer reverse 5'-3' (AttB2-XhoI) |
|---|---|---|
| GFP | GGGGACAAGTTTGTACAAAAAAGCAGGCTGAATT CTGAGCAAGGGCGAGGAGCTGT (SEQ ID NO: 1) | GGGGACCACTTTGTACAAGAAAGCTGGGTCTCG AGCTTGTACAGCTCGTCCATGCCG (SEQ ID NO: 2) |
| stopGFP | GGGGACAAGTTTGTACAAAAAAGCAGGCTTCTAG AATGGATGTAAGTAGGTGAGTGAGCA (SEQ ID NO: 3) | GGGGACCACTTTGTACAAGAAAGCTGGGTCTCG AGCTTGTACAGCTCGTCCATGCCGAGA (SEQ ID NO: 4) |
| GFPpart1 | GGGGACAAGTTTGTACAAAAAAGCAGGCTGAATT CTGAGCAAGGGCGAGGAGCTGT (SEQ ID NO: 5) | GGGGGCTCGAGTCGCCCTCGAACTTCACCTCG (SEQ ID NO: 6) |
| GFPpart2 | GGGGGGAATTCCACCCTGGTGAACCGCATCGA (SEQ ID NO: 7) | GGGGACCACTTTGTACAAGAAAGCTGGGTCTCG AGCTTGTACAGCTCGTCCATGCCG (SEQ ID NO: 8) |
| lNGFR | GGGGACCACTTTGTACAAGAAAGCTGGGTCTCGA GCTAGAGGATCCCCCTGTTCCACCT (SEQ ID NO: 9) | GGGGACAAGTTTGTACAAAAAAGCAGGCTGAAT TCTCACCATGGGGGCAGGTGCCACCGG (SEQ ID NO: 10) |
| HO-1 | GGGGACAAGTTTGTACAAAAAAGCAGGCTGAATT CTCACCATGGAGCGTCCGCAACCCGA (SEQ ID NO: 11) | GGGGACCACTTTGTACAAGAAAGCTGGGTCTAC AGCAACTGTCGCCACC (SEQ ID NO: 12) |
| CD4R1 | GGGGACAAGTTTGTACAAAAAAGCAGGCTGAATT CTAATAGTGACCACTCCTGGCTAATTTTTGTATT TTCAGTAGAGATAGGG (SEQ ID NO: 13) | GGGGACCACTTTGTACAAGAAAGCTGGGTCTCG AGGGTGAAACCCTTCTCTACTAAAAATACAAAA TTAGCCGGGCACA (SEQ ID NO: 14) |
| CD4R2 | — | GGGGACCACTTTGTACAAGAAAGCTGGTCTCGA GCCGCACTCCAGCCTCGGCGACAGAGCAAGACT CTATCTCA (SEQ ID NO: 15) |
| CD4R3 | — | GGGGACCACTTTGTACAAGAAAGCTGGGTCTCG AGTCGGGAGTACGAGACCAGCCTGGCCAACATA GTGAAATCC (SEQ ID NO: 16) |
| H2B | GGGGACAAGTTTGTACAAAAAAGCAGGCTGAATT CATGCCAGAGCCAGCGAAGTC (SEQ ID NO: 17) | GGGGACCACTTTGTACAAGAAAGCTGGGTCTCG AGGTGTACTTGGTGACGGCCTTA (SEQ ID NO: 18) |
| miRGE 1st hairpin | CAGAAGGGGATCCATCGATACTAGTGGTGATAGC AATGTCAGCAGTGCCT (SEQ ID NO: 19) | AGTAGCTTCTAGAGTAGAGTATGGTCAACCTTA CTT (SEQ ID NO: 20) |
| miRGE 2nd hairpin | CAGAAGGGGATCCGGTGATAGCAATGTCAGCAGT GCCT (SEQ ID NO: 21) | AGTAGCTACTAGTGTAGAGTATGGTCAACCTTA CTT (SEQ ID NO: 22) |
| miRGE 3rd hairpin | CAGAAGGCTCGAGGGTGATAGCAATGTCAGCAGT GCCT (SEQ ID NO: 23) | AGTAGCTGGATCCGTAGAGTATGGTCAACCTTA CTT (SEQ ID NO: 24) |

TABLE 5 miRGE hairpin components

| mir16-flanking sequence | GGTGATAGCAAT | SEQ ID NO: 25 |
| Lower stem sequence | CAGCAGTGCCT | SEQ ID NO: 26 |
| Lower stem sequence | TCAGCAGTGCCT | SEQ ID NO: 27 |
| Lower stem sequence | GTCAGCAGTGCCT | SEQ ID NO: 28 |
| Lower stem sequence | CGTCAGCAGTGCCT | SEQ ID NO: 29 |
| Lower stem sequence | ACGTCAGCAGTGCCT | SEQ ID NO: 30 |
| mir-30 loop sequence | GTGAAGCCACAGATG | SEQ ID NO: 31 |

TABLE 6 miRGE backbone sequences

| | Template 5'-3' |
|---|---|
| miRGE CCR5-7 | GGT GAT AGC AAT GTC AGC AGT GCC TTC ATA GAT TGG ACT TGA |

TABLE 6-continued miRGE backbone sequences

| | Template 5'-3' |
|---|---|
| | CAC TTG TGA AGC CAC AGA TGA<br>AGT GTC AAG CCC AAT CTA TGC<br>AAG TAA GGT TGA CCA TAC TCT<br>AC (SEQ ID NO: 32) |
| miRGE GFP | GGT GAT AGC AAT GTC AGC AGT<br>GCC TAG TTC ACC TTG ATG CCG<br>TTC TTG TGA AGC CAC AGA TGA<br>AGA ACG GCA CCA AGG TGA ACC<br>AAG TAA GGT TGA CCA TAC TCT<br>AC (SEQ ID NO: 33) |
| miRGE p22phox | GGT GAT AGC AAT GTC AGC AGT<br>GCC TAC ATG GCC CAC TCG ATC<br>TGC CCG TGA AGC CAC AGA TGG<br>GGC AGA TCG CGT GGG CCA TGC<br>AAG TAA GGT TGA CCA TAC TCT<br>AC (SEQ ID NO: 34) |

Lentiviral vector production and titration. Lentiviral vector stocks were generated using transient transfection of HEK 293T cells with the specific lentivector transfer plasmid, the psPAX2 plasmid encoding gag/pol and the pCAG-VSVG envelope plasmid, as previously described (Giry-Laterriere et al., 2011a, Giry-Laterriere et al., 2011a).

Lentivector titration was performed using transduction of HT-1080 cells followed by flow cytometry quantification of mcherry-positive cells five days after transduction, as previously described (Giry-Laterriere et al., 2011a, Giry-Laterriere et al., 2011a).

Cell culture and knockdown analysis. All cell lines were cultured in high glucose Dulbecco's modified eagle medium (Sigma) supplemented with 10% fetal calf serum, 1% Penicillin, 1% Streptomycin, and 1% L-glutamine. For each knockdown assay, cells were analyzed at least 5 days after transduction. For CCR5 knockdown studies, a subclone of HeLa-derived TZMb1 cells (AIDS Repository, Germantown, Md.), expressing high levels of human CCR5, named here HeLa R5, was used. For GFP knockdown, the same cells were used after GFP transduction at 1 copy of the vector and sorting of the GFP positive cells. CCR5 expression was detected using an anti-human CCR5-APC-antibody, (BD Pharmingen Cat. 550856) and flow cytometry analysis using FACS Cyan (Beckman Coulter). GFP expression was assessed on the same flow cytometer using GFP fluorescence median. Briefly, HeLa cells were transduced at 0.2 MOI with the miRGE-based knockdown vector to avoid the presence of a high copy number of the vector per cell and obtain comparable conditions. GFP or CCR5 expression was compared between the transduced and the remaining untransduced population of cells and expressed as a percentage of CCR5 expression relatively to the untransduced population.

Real-time Quantitative Reverse Transcriptase Polymerase Chain Reaction. Cells or organotypic explant of organ of Corti were harvested and mRNA was extracted using Qiagen RNeasy mini kit following the manufacturer's instructions. RNA concentration was determined using a Nanodrop. 500 ng was used for cDNA synthesis using Takara PrimeScript RT reagent Kit following manufacturer's instruction. Real-time PCR was performed using SYBR green assay on a 7900HT SDS system from ABI. The efficiency of each primer was verified with serial dilutions of cDNA. Relative expression levels were calculated by normalization to the geometric mean of the two house-keeping genes GAPDH and EF1a and the GAG lentivector gene. The highest normalized relative quantity was arbitrarily designated as a value of 1.0. Fold changes were calculated from the quotient of means of these normalized quantities and reported as ±SEM. Sequences of the qPCR primers used are provided in Table 7.

TABLE 7 qPCR primers

| Amplicon | Primer forward 5'-3' | Primer reverse 5'-3' |
|---|---|---|
| Cyba (p22phox) | TGGACGTTTCACACAGTGGT<br>(SEQ ID NO: 35) | TGGACCCCTTTTTCCTCTTT<br>(SEQ ID NO: 36) |
| miRGE pri-miRNA | GGTGATAGCAATGTTCAGCAGTGCCT<br>(SEQ ID NO: 37) | GTAGAGTATGGTCAACCTTACTT<br>(SEQ ID NO: 38) |
| mature miRGE | LNA modified proprietary sequence (exiqon) | |
| GAG | GGAGCTAGAACGATTCGCAGTTA<br>(SEQ ID NO: 39) | GGTTGTAGCTGTCCCAGTATTTGTC<br>(SEQ ID NO: 40) |
| EEF1a | TCCACTTGGTCGCTTTGCT<br>(SEQ ID NO: 41) | CTTCTTGTCCACAGCTTTGATGA<br>(SEQ ID NO: 42) |
| GAPDH | TCCATGACAACTTTGGCATTG<br>(SEQ ID NO: 43) | CAGTCTTCTGGGTGGCAGTGA<br>(SEQ ID NO: 44) |

Quantitative Reverse Transcriptase Polymerase Chain Reaction for mature miRNA detection. HeLa R5 cells were transduced at 0.2 MOI with lentivectors carrying the different SMIG. Transduced population (expressing mCherry) was sorted by FACS resulting in a homogeneous cell population carrying a single copy of the vector/cell. Total RNA was extracted using Trizol Reagent (Ambion) according to manufacturer instructions. RNA concentration was determined using a Nanodrop. 100 ng of RNA was used for the reverse transcription (miRCURY LNA™ miRNA PCR, Polyadenylation and cDNA synthesis kit (exiqon)). Reverse transcription was followed by real-time PCR amplification (ExiLENT SYBR® Green master mix kit (exiqon)) with LNA™ enhanced primers. Relative expression levels of the mature miRGE were calculated by normalization to the geometric mean of the two house-keeping miRNA (U6 and RNU5G). Fold changes were calculated from the quotient of means of these normalized quantities and reported as ±SEM. Sequences of the LNA™ enhanced primers were not provided by the manufacturer.

Reactive Oxygen Species measurement by Amplex Red assay. PLB-985 cells were cultured in RPMI medium (Gibco), transduced as described above and differentiated into neutrophil-like cells during 5 days in presence of 1.25% DMSO. Levels of H2O2 produced by intact PLB-985 cells after stimulation of NOX2 with 100 nM phorbol myristate acetate (PMA) were then measured using Amplex Red fluorescence as previously described (Jaquet et al., 2011). Fluorescence was measured with a FluoSTAR OPTIMA, BMG labtech instrument at 37° C.

Organotypic culture and transduction of rat organ of Corti. Three days old Wistar Rats were decapitated and the heads were cut sagittaly to remove the brain. The two otic capsules were isolated and transferred into ice-cold Hank's balanced salt solution (HBSS) (Invitrogen, USA) for sterile dissection under a binocular microscope (Nikon SMZ800, Japan) with forceps (World Precision Instruments, USA). After bone removal, the cochlea was transferred to a Transwell-Clear insert (6-well format, Corning, USA) with a permeable polyester membrane (0.4 μm pore size). The membranes were pre-coated with Celltak (Corning, USA) according to manufacturer's protocol. The organ of Corti (OC) was then separated from stria vascularis and the modiolus and plated on the insert, with the hair cells facing up. Dissection medium was carefully removed and 1.5 ml otic culture medium: (DMEM/F12 (Invitrogen, USA), 0.01% Ampicillin (Sigma, USA) and 10% fetal bovine serum (Invitrogen, USA) was added to the lower compartment under the insert membrane. On the following day, the medium on the insert was removed and they were transferred into an empty well. For the transduction, 200 μl otic culture medium was added on the explant together with 70 μl DMEM/F12 (Invitrogen/USA) containing 106, 5×106 or 107 particles of the stopGFP triple miRGE hairpin lentivector targeting p22phox. After 30 minutes of incubation at 37° C. and 5% C02, 1.5 ml otic culture medium was added to the lower compartment. The medium was replaced with fresh otic culture medium on the two following days. 5 days after the initial transduction, cochlear explants were either detached with trypsin for mRNA isolation or fixed for 10 minutes with 4% paraformaldehyde for immunostainings.

Immunostaining and confocal microscopy of rat organotypic culture of organ of Corti. Cochlear explants were fixed with 4% paraformaldehyde for 10 minutes at room temperature. Explants were transferred (by cutting the insert membrane) to a 24 well plate, washed three times with PBS and permeabilized with 3% Triton-X 100 for 30 minutes. Cochlear explants were immersed in a blocking buffer containing 2% bovine serum albumin (BSA) and 0.01% Triton-X 100 for 1 hour at room temperature. Explants were incubated with the anti-MyoVIIa (1:500, rabbit; Proteus, USA) antibody in blocking buffer overnight at 4° C. On the following day, tissues were rinsed three times with PBS and incubated with the secondary antibody anti-rabbit Alexa Fluor 488 (1:500; Invitrogen, USA) in blocking buffer for 2 hours at room temperature. Explants were again washed 3 times with PBS and mounted on a glass slide with Fluoroshield containing DAPI (Sigma Aldrich, USA). The labelled cells were visualized with a confocal laser-scanning microscope (Zeiss LSM710) equipped with a CCD camera (Leica Microsystems) with a Planapochromat 10×/0.3 NA objective.

Knockdown of CCR5 in humanized mice leukocytes. Human CD34 isolated from cord blood using magnetic beads (Miltenyi) were cultivated in activation medium (Cell Gro medium containing 20 ng/mL recombinant human [rh] stem cell factor (SCF), 20 ng/mL rh Flt3-L, 20 ng/mL rh interleukin-3 [IL-3], 20 ng/mL rh TPO1, 1% v/v penicillin-streptomycin [Penstrep]). The cells were seeded in a 24-well plate at 1.0_106 cells/mL for_24 h at 37_C in activation medium for pre-stimulation. On the next day for transduction, Lentiblast B was added to the medium in a dilution of 1:1,000. Used MOI for transduction was 50. One well with 0.1_106 cells was not transduced and served as negative control. CD34 cells were cultivated for 48 h and then harvested except the transduction controls. The cells designated for transplantation were frozen and stored until transplantation of newborn NGS mice in liquid N2. Newborn NGS mice were then irradiated with 1 Gy and then transplanted with 260,000 CD34+ cells. Week 23 after birth, engraftment check was done by analyzing peripheral blood from the mice. CCR5 expression was then investigated at 28 weeks old using the following antibodies: huCD45 FITC (304006), CD3 AF700 (300424), CD4 PE-CY7 (300512), CD8 BV421 (301036), and CCR5 APC (359122) (or isocontrol #400611) from BioLegend.

Prediction of the minimum free energy of spacer sequences. The minimum free energy (MFE) of spacers was calculated using RNA fold web server (Institute for Theoretical Chemistry, University of Vienna, available on the world wide web at rna.tbi.univie.ac.at/cgi-bin/RNAWebSuite/RNAfold.cgi). To allow comparison of MFE between spacers, obtained values were divided by the length of the spacer.

Calculation of the efficiency of concatenation of triple hairpin concatenates. The concatenation efficiency of triple hairpin constructs (E) was calculated according to the formula $E=\ln(CP)/\ln(KP)$ where KP and CP are respectively the knockdown of CCR5 obtained with single and triple hairpin constructs. If E=3, a fully additive effect of the hairpins is observed in the concatenate. If E=1 the triple hairpin construct is as efficient as the single hairpin construct and no additive effect of the hairpins concatenation is observed.

Statistical analysis. Statistical analyses were performed using GraphPad Prism 5.04 (GraphPad Software, La Jolla, Calif.). One-way analysis of variance followed by Bonferroni's multiple comparison tests, as well as t-tests (non-parametric, Mann-Whitney U-test).

Example 2—Results

A spacer sequence is required for polymerase II promoter-driven miRNA mediated target gene knockdown. To optimize the miRGE-based knockdown and better understand the role of the spacer, the Green Fluorescent Protein (GFP) sequence was placed either on the 5' or on the 3'-end of the miRGE hairpin sequences in a lentiviral vector (FIG. 1a). HeLa cells expressing CCR5 (R5 cells) were transduced at an MOI of 0.2 to reduce statistical probabilities of having more than one copy of transgene/cell (FIG. 1b). Both single and a triple hairpins targeting CCR5 were used. Two different polII-dependent promoters were used: the ubiquitin promoter (UBI) and a spliced version of the elongation factor 1 promoter, EFs[25] (cgatggctccggtgcccgtcagtgggcagagcgcacatcgcc-cacagtccccgagaagttgggggagggtcggcaattgaac cggtgcctagagaaggtggcgcggggtaaactgggaaagt-gatgtcgtgtactggctccgccttttcccgagggtgggggagaacc gtatataagtgcagtagtcgccgt-gaacgttcttttcgcaacgggtttgccgccagaacacaggtgtcgtgacgcg; SEQ ID NO: 45). When the UBI promoter was used, absence of the spacer entirely precluded CCR5 knockdown, even when three hairpins were used (FIG. 1c).

The efficacy of the spacer depends on its position. With the spacer between the promoter and the miRNA, an efficient CCR5 knockdown was observed with a single hairpin, which was markedly enhanced with a concatenated triple hairpin construct. When the spacer was put in the 3' position of the miRNA gene, the single hairpin showed a decreased CCR5 knockdown efficiency, while the increased knockdown effect of the concatenate was entirely lost (FIGS. 1c and 1e). The situation was slightly different for the EFs promoter (FIG. 1d). The efficacy of a single hairpin did not depend on the presence of a spacer, but no additive effect of the triple concatenate was observed in the absence of a spacer (FIG. 1e). In contrast, with the spacer between the promoter and the hairpins, a maximal effect of the triple concatenate was achieved while less pronounced effect was observed with the spacer in 3'.

Together, the data demonstrate that a spacer sequence—preferentially located in 5' of the miRNA—is required to drive efficient knockdown via two types of polII-dependent promoters. The spacer is also required for additive effects of the hairpin concatenation (FIG. 1e).

Efficiency of miRNA-based knockdown depends on the spacer sequence. The potency of several coding and non-coding spacer sequences was assessed (FIG. 2a; Table 8). Five miRGE minigenes with coding sequences were generated as spacers: Green Fluorescent Protein (GFP), Microsomal Glutathione S-transferase-2 (MGST2), truncated Nerve Growth Factor Receptor (dNGFR), Heme oxygenase-1 (HO-1), and Histone 2B (H2B) cDNAs (Table 9). The first intron of the CD4 gene, iCD4, was used as a noncoding spacer sequence. Lentivectors carrying the respective minigenes were used to transduce HeLa R5 cells. A significant knockdown of the CCR5 protein was observed in the transduced population of cells with all coding sequences (MGST, LNGFR, HO-1 and H2B spacers). The GFP sequence spacer resulted in the highest knockdown of CCR5. The worst performing spacers were iCD4 and H2B (<10% knockdown), while the other coding sequences resulted in an intermediate efficiency (FIG. 2a).

Table 8. Spacer Sequences and Biophysical Features

In an attempt to identify specific regions within spacer sequences which have an effect on the knockdown efficiency, truncated forms of GFP (GPF1, GFP2) and of the iCD4 (iCD42, iCD43) were designed (FIGS. 2b and 2c). Remarkably, the activity of the truncated GFP1 and GFP2 was comparable to full length GFP (FIG. 2b). The situation was different for the CD4 intron, where the shorter amplicons (iCD42 and iCD43) resulted in a moderate but significant knockdown of CCR5 (FIG. 2c). However, these truncated CD4 first intron sequences were still inefficient spacers when compared to sequences of similar length (GFP1 or GFP2) (FIG. 2b and FIG. 2c). These results demonstrate that the spacer activity does not simply depend on the length, but that the nucleotide sequence also seems to determine its efficiency. There was no correlation observed between the predicted minimum free energy (MFE) of spacers and

| Spacer | Length (bp) | Predicted MFE Kcal/mol | % GC | coding | Comments |
| --- | --- | --- | --- | --- | --- |
| Green Fluorescent protein (GFP) | 717 | −264.6 | 61.11 | YES | Reference spacer |
| Truncated GFP1 | 369 | −142.2 | 62.87 | | |
| GFP2 | 388 | −116.4 | 59.53 | | |
| Stop codons in the 3 reading frame after the start codon of GFP (stopGFP) | 732 | — | — | NO | non coding form |
| Microsomal Glutathion Transferase-2 (MGST2) | 726 | −197.7 | 43.92 | YES | Resistance to Busulfan |
| Truncated form of the Nerve Growth Factor Receptor (deltaNGFR) | 843 | −397.7 | 66.86 | YES | Pre-implantation selection |
| Heme Oxygenase (HO-1) | 863 | −336.2 | 61.24 | YES | Cytoprotection |
| Histone2B (H2B) | 378 | −123.7 | 58.99 | YES | Neutral |
| Amplicons from the 1st intron of the CD4 gene iCD41 | 793 | −235.9 | 46.71 | NO | Neutral? |
| iCD42 | 620 | −189.2 | 45.48 | | |
| iCD43 | 380 | −136 | 49.36 | | | the knockdown efficiency (FIG. 7a). GC content of the spacer sequences was assessed and found that spacers with higher GC content tended to correlate with the higher knockdown efficiency (FIG. 7b).

TABLE 9

Spacer sequences

| Spacer | Sequence |
|---|---|
| GFP | ATGGATGTAAGTAGGTGAGTGAGCAAGGGCGAGGAGCTGTTCACCGGGGTGGTGCCCATCCTGGTCGAGCTGGACGG<br>CGACGTAAACGGCCACAAGTTCAGCGTGTCCGGCGAGGGCGAGGGCGATGCCACCTACGGCAAGCTGACCCTGAAGT<br>TCATCTGCACCACCGGCAAGCTGCCCGTGCCCTGGCCCACCCTCGTGACCACCCTGACCTACGGCGTGCAGTGCTTC<br>AGCCGCTACCCCGACCACATGAAGCAGCACGACTTCTTCAAGTCCGCCATGCCCGAAGGCTACGTCCAGGAGCGCAC<br>CATCTTCTTCAAGGACGACGGCAACTACAAGACCCGCGCCGAGGTGAAGTTCGAGGGCGACCACCCTGGTGAACCGC<br>ATCGAGCTGAAGGGCATCGACTTCAAGGAGGACGGCAACATCCTGGGGCACAAGCTGGAGTACAACTACAACAGCCA<br>CAACGTCTATATCATGGCCGACAAGCAGAAGAACGGCATCAAGGTGAACTTCAAGATCCGCCACAACATCGAGGACG<br>GCAGCGTGCAGCTCGCCGACCACTACCAGCAGAACACCCCCATCGGCGACGGCCCCGTGCTGCTGCCCGACAACCAC<br>TACCTGAGCACCCAGTCCGCCCTGAGCAAAGACCCCAACGAGAAGCGCGATCACATGGTCCTGCTGGAGTTCGTGAC<br>CGCCGCCGGGATCACTCTCGGCATGGACGAGCTGTACAAGTAAAGCGGCCTGAATCGCCAGTGTC<br>(SEQ ID NO: 46) |
| stopGFP | AATTCATGGATGTAAGTAGGTGAGTGAGCAAGGGCGAGGAGCTGTTCACCGGGGTGGTGCCCATCCTGGTCGAGCTG<br>GACGGCGACGTAAACGGCCACAAGTTCAGCGTGTCCGGCGAGGGCGAGGGCGATGCCACCTACGGCAAGCTGACCCT<br>GAAGTTCATCTGCACCACCGGCAAGCTGCCCGTGCCCTGGCCCACCCTCGTGACCACCCTGACCTACGGCGTGCAGT<br>GCTTCAGCCGCTACCCCGACCACATGAAGCAGCACGACTTCTTCAAGTCCGCCATGCCCGAAGGCTACGTCCAGGAG<br>CGCACCATCTTCTTCAAGGACGACGGCAACTACAAGACCCGCGCCGAGGTGAAGTTCGAGGGCGACACCCTGGTGAA<br>CCGCATCGAGCTGAAGGGCATCGACTTCAAGGAGGACGGCAACATCCTGGGGCACAAGCTGGAGTACAACTACAACA<br>GCCACAACGTCTATATCATGGCCGACAAGCAGAAGAACGGCATCAAGGTGAACTTCAAGATCCGCCACAACATCGAG<br>GACGGCAGCGTGCAGCTCGCCGACCACTACCAGCAGAACACCCCCATCGGCGACGGCCCCGTGCTGCTGCCCGACAA<br>CCACTACCTGAGCACCCAGTCCGCCCTGAGCAAAGACCCCAACGAGAAGCGCGATCACATGGTCCTGCTGGAGTTCG<br>TGACCGCCGCCGGGATCACTCTCGGCATGGACGAGCTGTACAAGTAAAGCGGCCTGAATCGCCAGTGTC<br>(SEQ ID NO: 47) |
| GFP1 | AATTCATGGATGTAAGTAGGTGAGTGAGCAAGGGCGAGGAGCTGTTCACCGGGGTGGTGCCCATCCTGGTCGAGCTG<br>GACGGCGACGTAAACGGCCACAAGTTCAGCGTGTCCGGCGAGGGCGAGGGCGATGCCACCTACGGCAAGCTGACCCT<br>GAAGTTCATCTGCACCACCGGCAAGCTGCCCGTGCCCTGGCCCACCCTCGTGACCACCCTGACCTACGGCGTGCAGT<br>GCTTCAGCCGCTACCCCGACCACATGAAGCAGCACGACTTCTTCAAGTCCGCCATGCCCGAAGGCTACGTCCAGGAG<br>CGCACCATCTTCTTCAAGGACGACGGCAACTACAAGACCCGCGCCGAGGTGAAGTTCGAGGGCGACC<br>(SEQ ID NO: 48) |
| GFP2 | AATTCCACCCTGGTGAACCGCATCGAGCTGAAGGGCATCGACTTCAAGGAGGACGGCAACATCCTGGGGCACAAGCT<br>GGAGTACAACTACAACAGCCACAACGTCTATATCATGGCCGACAAGCAGAAGAACGGCATCAAGGTGAACTTCAAGA<br>TCCGCCACAACATCGAGGACGGCAGCGTGCAGCTCGCCGACCACTACCAGCAGAACACCCCCATCGGCGACGGCCCC<br>GTGCTGCTGCCCGACAACCACTACCTGAGCACCCAGTCCGCCCTGAGCAAAGACCCCAACGAGAAGCGCGATCACAT<br>GGTCCTGCTGGAGTTCGTGACCGCCGCCGGGATCACTCTCGGCATGGACGAGCTGTACAAGTAAAGCGGCCTGAATC<br>GCCAGTGTC<br>(SEQ ID NO: 49) |
| H2B | ATGCCAGAGCCAGCGAAGTCTGCTCCCGCCCCGAAAAAGGGCTCCAAGAAGGCGGTGACTAAGGCGCAGAAGAAAGG<br>CGGCAAGAAGCGCAAGCGCAGCCGCAAGGAGAGCTATTCCATCTATGTGTACAAGGTTCTGAAGCAGGTCCACCCTG<br>ACACCGGCATTTCGTCCAAGGCCATGGGCATCATGAATTCGTTTGTGAACGACATTTTCGAGCGCATCGCAGGTGAG<br>GCTTCCCGCCTGGCGCATTACAACAAGCGCTCGACCATCACCTCCAGGGAGATCCAGACGGCCGTGCGCCTGCTGCT<br>GCCTGGGGAGTTGGCCAAGCACGCCGTGTCCGAGGGTACTAAGGCCGTCACCAAGTACACCAGCGCTAAG<br>(SEQ ID NO: 50) |
| NGFR | AATTCTCACCATGGGGGCAGGTGCCACCGGCCGCGCCATGGACGGGCCGCGCCTGCTGCTGTTGCTGCTTCTGGGGG<br>TGTCCCTTGGAGGTGCCAAGGAGGCATGCCCCACAGGCCTGTACACACACAGCGGTGAGTGCTGCAAAGCCTGCAAC<br>CTGGGCGAGGGTGTGGCCCAGCCTTGTGGAGCCAACCAGACCGTGTGTGAGCCCTGCCTGGACAGCGTGACGTTCTC<br>CGACGTGGTGAGCGCGACCGAGCCGTGCAAGCCGTGCACCGAGTGCGTGGGGCTTCCAGAGCATGTCGGCGCCGTGCG<br>TGGAGGCCGACGACGCCGTGTGCCGCTGCGCCTACGGCTACTACCAGGATGAGACGACTGGGCGCTGCGAGGCGTGC<br>CGCGTGTGCGAGGCGGGCTCGGGCCTCGTGTTCTCCTGCCAGGACAAGCAGAACACCGTGTGCGAGGAGTGCCCCGA<br>CGGCACGTATTCCGACGAGGCCAACCACGTGGACCCGTGCCTGCCCTGCACCGTGTGCGAGGACACCGAGCGCCAGC<br>TCCGCGAGTGCACACGCTGGGCCGACGCCGAGTGCGAGGAGATCCTTGGCCGTTGGATTACACGGTCCACACCCCCA<br>GAGGGCTCGGACAGCACAGCCCCAGCACCCAGGAGCCTGAGGCACCTCCAGAACAAGACCTCATAGCCAGCACGGT<br>GGCAGGTGTGGTGACCACAGTGATGGGCAGCTCCCAGCCCGTGGTGACCCGAGGCACCACCGACAACCTCATCCCTG<br>TCTATTGCTCCATCCTGGCTGCTGTGGTTGTGGGCCTTGTGGCCTACATAGCCTTCAAGAGGTGGAACAGGGGGATC<br>CTCTAGC<br>(SEQ ID NO: 51) |
| MGST2 | AATTCGGCACGAGGGACTTCTGTTCCAGAGCAAAGGTCATTCAGCCGCTTGAATCAGCCTTTTCCCCCCACCCGGTC<br>CCCAACTTTGTTTACCCGATAAGGAAGGTCAGCATTCAAAGTCAAGAAGCGCCATTTATCTTCCCGTGCGCTCTACA<br>AATAGTTCCGTGAGAAAGATGGCCGGGAACTCGATCCTGCTGCTGTCTCTATTCTCTCGGCCTGTCAGCAAAG<br>TTATTTTGCTTTGCAAGTTGGAAAGGCAAGATTAAAATACAAAGTTACGCCCCAGCAGTCACTGGGTCACCAGAGT<br>TTGAGAGAGTATTTCGGGCACAACAAAACTGTGTGGAGTTTTATCCTATATTCATAATTACATTGTGGATGGCTGGG<br>TGGTATTTCAACCAAGTTTTTGCTACTTGTCTGGGTCTGGTGTACATATATGGCCGTCACCTATACTTCTGGGGATA<br>TTCAGAAGCTGCTAAAAAACGGATCACCGGTTTCCGACTGAGTCTGGGGATTTTGGCCTTGTTGACCCTCCTAGGTG<br>CCCTGGGAATTGCAAACAGCTTTCTGGATGAATATCTGGACCTCAATATTGCCAAGAAACTGAGGCGGCAATTCTAA<br>CTTTTTCTCTTCCCTTTAATGCTTGCAGAAGCTGTTCCCACCATGAAGGTAATATGGTATCATTTGTTAAATAAAA<br>TAAAGTCTTTATTCTGTTAAAAAAAAAAAAAAAAAAC<br>(SEQ ID NO: 52) |
| HO-1 | AATTCATGGAGCGTCCGCAACCCGACAGCATGCCCCAGGATTTGTCAGAGGCCCTGAAGGAGGCCACCAAGGAGGTG<br>CACACCCAGGCAGAGAATGCTGAGTTCATGAGGAACTTTCAGAAGGGCCAGGTGACCCGAGACGGCTTCAAGCTGGT<br>GATGGCCTCCCTGTACCACATCTATGTGGCCCTGGAGGAGGAGATTGAGCGCAACAAGGAGAGCCCAGTCTTCGCCC<br>CTGTCTACTTCCCAGAAGAGCTGCACCGCAAGGCTGCCCTGGAGCAGGACCTGGCCTTCTGGTACGGGCCCCGCTGG |

TABLE 9-continued

Spacer sequences

| Spacer | Sequence |
|---|---|
| | CAGGAGGTCATCCCCTACACACCAGCCATGCAGCGCTATGTGAAGCGGCTCCACGAGGTGGGGCGCACAGAGCCCGA<br>GCTGCTGGTGGCCCACGCCTACACCCGCTACCTGGGTGACCTGTCTGGGGGCCAGGTGCTCAAAAAGATTGCCCAGA<br>AAGCCCTGGACCTGCCCAGCTCTGGCGAGGGCCTGGCCTTCTTCACCTTCCCCAACATTGCCAGTGCCACCAAGTTC<br>AAGCAGCTCTACCGCTCCCGCATGAACTCCCTGGAGATGACTCCCGCAGTCAGGCAGAGGGTGATAGAAGAGGCCAA<br>GACTGCGTTCCTGCTCAACATCCAGCTCTTTGAGGAGTTGCAGGAGCTGCTGACCCATGACACCAAGGACCAGAGCC<br>CCTCACGGGCACCAGGGCTTCGCCAGCGGGCCAGCAACAAAGTGCAAGATTCTGCCCCCGTGGAGACTCCCAGAGGG<br>AAGCCCCCACTCAACACCCGCTCCCAGGCTCCGCTTCTCCGATGGGTCCTTACACTCAGCTTTCTGGTGGCGACAGT<br>TGCTGTAGGGCTTTATGCCATGTGAC<br>(SEQ ID NO: 53) |
| iCD41 | AATTCTAATAGTGACCACTCCTGGCTAATTTTTGTATTTTCAGTAGAGATAGGGTTTCACTATGTTGGCCAGGCTGG<br>TCTCCAACTCCTGACCTAAAGTGATCCACCCACCTTGGTTTCCCAAAGTGCTGGGATTACAGGCGTGAGCCACCGTG<br>CCTGGACATATATCTATCTTTTTTTTTTTGAGATGGAGTCTCGCTCTGTTGCCCAGGCTGGAGTGCAGTGGCGTGA<br>TTTCGGCTCACTGCAACCTCCGCCTCCCGGGTTCAAGTGATTCTCCTGCCTCAGCCTCCCAAGTAGCTGAGATTACA<br>GACGTGCGTCACCATGCCCAGCTAATTTTTGTATTTTTAGTAGAGATGGGATTTCACTATGTTGGCCAGGCTGGTCT<br>CGTACTCCCGACCTCAGGTGATCCACTTGCCTTGGCCTCCCAAAGTGCTGGAATTACAGGTGTGAGCCACTGCATCC<br>GGCCTTATATATCTATCTTGTCTGTCTGACTGTCTAATCTAATTCATCTATTTTATCTGTTTATCTTATCTATCATC<br>TATTTATCTAATCTATCTGTCTGTATGTCTGTTTTTTTTTTGTTTTTTTTTTTTTTTTGAGATAGAGTCTTGCTCTG<br>TCGCCGAGGCTGGAGTGCGGTGGCGCGATCTCAGCTCACTGCTGAACCTCCGCCTCCTGGGTTCTAAGCGATTCTCC<br>TGCCTCAATCTTTGGAGTAGCTGGGATTACAGGCCCGTACCACTGTGCCCGGCTAATTTTGTATTTTTAGTAGAGAA<br>GGGTTTCACCC<br>(SEQ ID NO: 54) |
| iCD42 | AATTCTAATAGTGACCACTCCTGGCTAATTTTTGTATTTTCAGTAGAGATAGGGTTTCACTATGTTGGCCAGGCTGG<br>TCTCCAACTCCTGACCTAAAGTGATCCACCCACCTTGGTTTCCCAAAGTGCTGGGATTACAGGCGTGAGCCACCGTG<br>CCTGGACATATATCTATCTTTTTTTTTTTGAGATGGAGTCTCGCTCTGTTGCCCAGGCTGGAGTGCAGTGGCGTGA<br>TTTCGGCTCACTGCAACCTCCGCCTCCCGGGTTCAAGTGATTCTCCTGCCTCAGCCTCCCAAGTAGCTGAGATTACA<br>GACGTGCGTCACCATGCCCAGCTAATTTTTGTATTTTTAGTAGAGATGGGATTTCACTATGTTGGCCAGGCTGGTCT<br>CGTACTCCCGACCTCAGGTGATCCACTTGCCTTGGCCTCCCAAAGTGCTGGAATTACAGGTGTGAGCCACTGCATCC<br>GGCCTTATATATCTATCTTGTCTGTCTGACTGTCTAATCTAATTCATCTATTTTATCTGTTTATCTTATCTATCATC<br>TATTTATCTAATCTATCTGTCTGTATGTCTGTTTTTTTTTTGTTTTTTTTTTTTTTGAGATAGAGTCTTGCTCTG<br>TCGCCGAGGCTGGAGTGCGGC<br>(SEQ ID NO: 55) |
| iCD43 | AATTCTAATAGTGACCACTCCTGGCTAATTTTTGTATTTTCAGTAGAGATAGGGTTTCACTATGTTGGCCAGGCTGG<br>TCTCCAACTCCTGACCTAAAGTGATCCACCCACCTTGGTTTCCCAAAGTGCTGGGATTACAGGCGTGAGCCACCGTG<br>CCTGGACATATATCTATCTTTTTTTTTTTGAGATGGAGTCTCGCTCTGTTGCCCAGGCTGGAGTGCAGTGGCGTGA<br>TTTCGGCTCACTGCAACCTCCGC<br>(SEQ ID NO: 56) |

Figure 2:
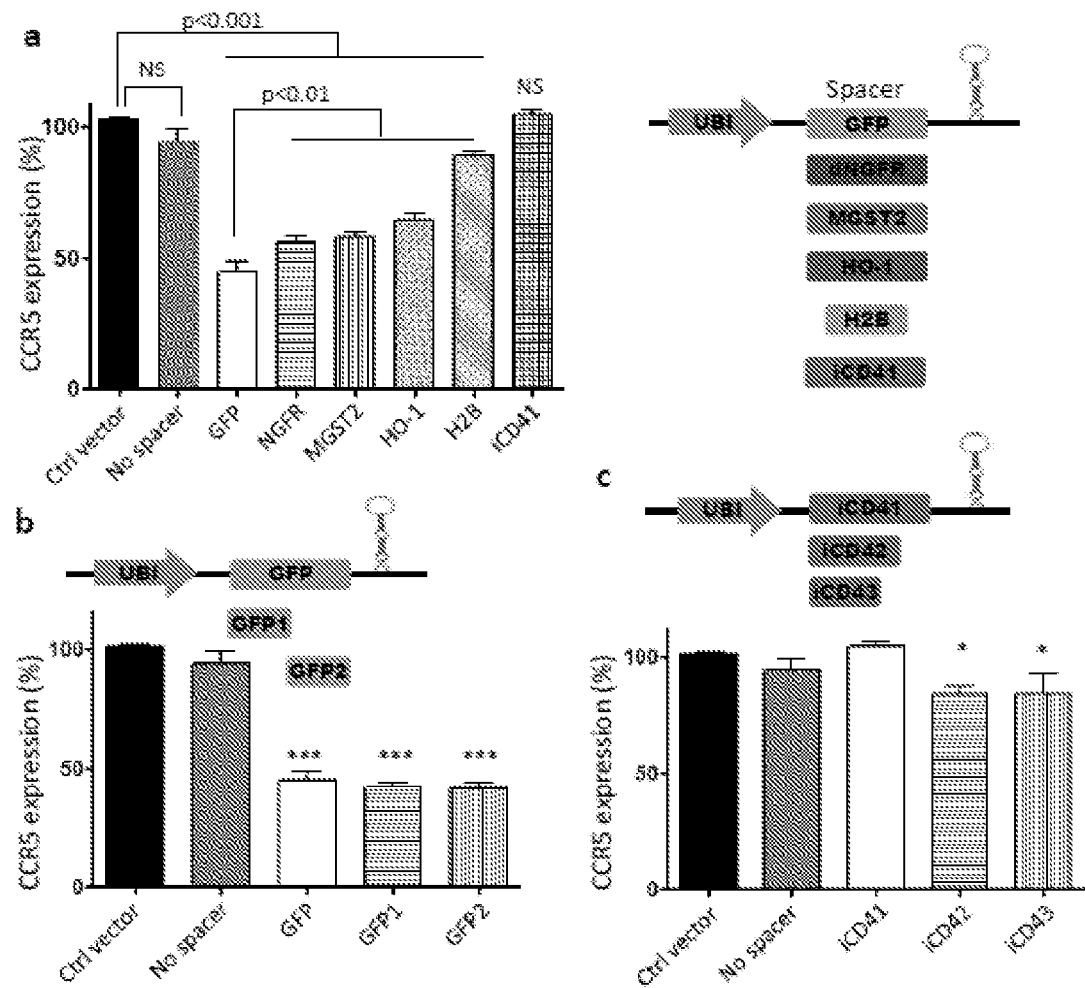
FIG. 2: Efficiency of the miRNA-based knockdown depends on the spacer. (a) Single miRGE hairpin-based constructs targeting CCR5 were designed with different spacers derived either from coding sequences of GFP (Green Fluorescent Protein), MGST-2 (Microsomal Glutathione S-transferase-2), dNGFR (truncated Nerve Growth Factor Receptor), HO-1 (Heme oxygenase-1), HO-1, and H2B (Histone 2B) or from noncoding sequences (first intron of the CD4 gene=iCD41) and transduced at 0.2 MOI in HeLa R5 cells. Histogram showing the expression of CCR5 in the transduced population relative to the untransduced population, as assessed by FACS immunostaining. (b) miRGE constructs were designed with truncated forms of GFP (GFP1 and GFP2) or (c) the first intron of CD4 (iCD42 and iCD43) and transduced at 0.2 MOI in HeLa R5 cells. Histograms show the level of CCR5 expression of the transduced population relatively to the untransduced population. Data represent the mean+/− SEM of three independent experiments.
Figure 3:
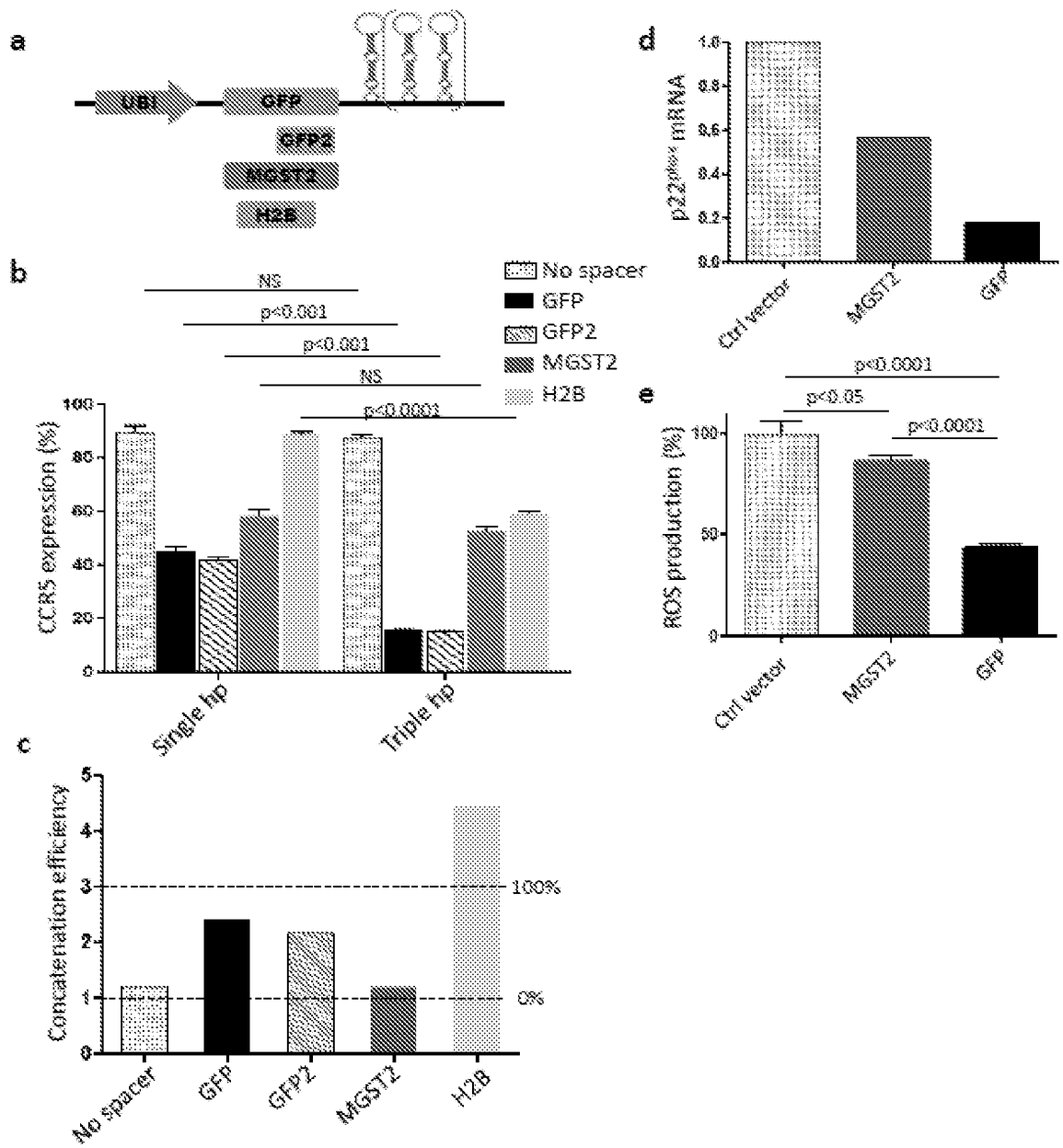
FIG. 3: The spacer sequence determines the additive effects of miRNA hairpin concatenation. (a) The efficiency of MGST2, H2B and GFP as spacer was assessed on miRGE hairpin concatenation (three hairpins concatenate) in HeLa expressing CCR5 cells. (b) Histogram shows the level of CCR5 expression of the transduced population relatively to the remained untransduced population for the GFP spacer (black bars), the second part of GFP (GFP2) (hatched), MGST2 spacer (dark grey bars) and the H2B spacer (clear grey bars). (c) The bar graph shows the concatenation efficiency for the triple hairpin constructs, as calculated with the formula in FIG. 9. For the calculation of the concatenation efficiency, CCR5 knockdown with a single miRGE hairpin (knock-down potency (KP)) and with a triple miRGE concatenate (concatenation potency (CP)) were considered. (d-e) The potency of MGST2 and GFP as spacers was also compared in a triple hairpin concatenate targeting the NADPH oxidase subunit $p22^{phox}$. mRNA level of $p22^{phox}$ as assessed in the promyelocytic leukemia cell line PLB985 by QPCR (d) and on NADPH oxidase activity by Amplex red assay (e). Data represent the mean+/− SEM of three independent experiments.
Figure 7:
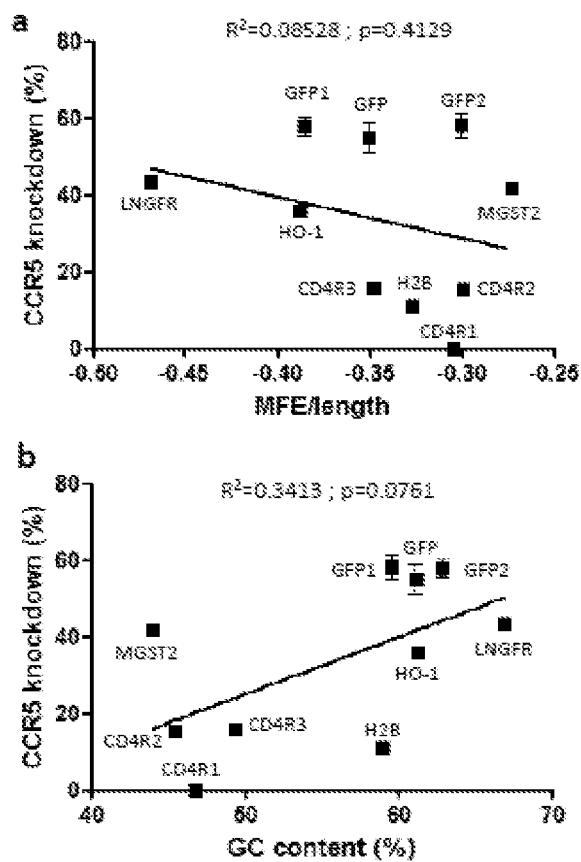
FIG. 7: Impact of the length and biophysical features of the spacer on the knockdown efficiency. Plots showing the correlation between CCR5 knockdown and (a) the minimum free energy/length or (b) the GC content of the spacers described in this figure.
Figures 8, 9:
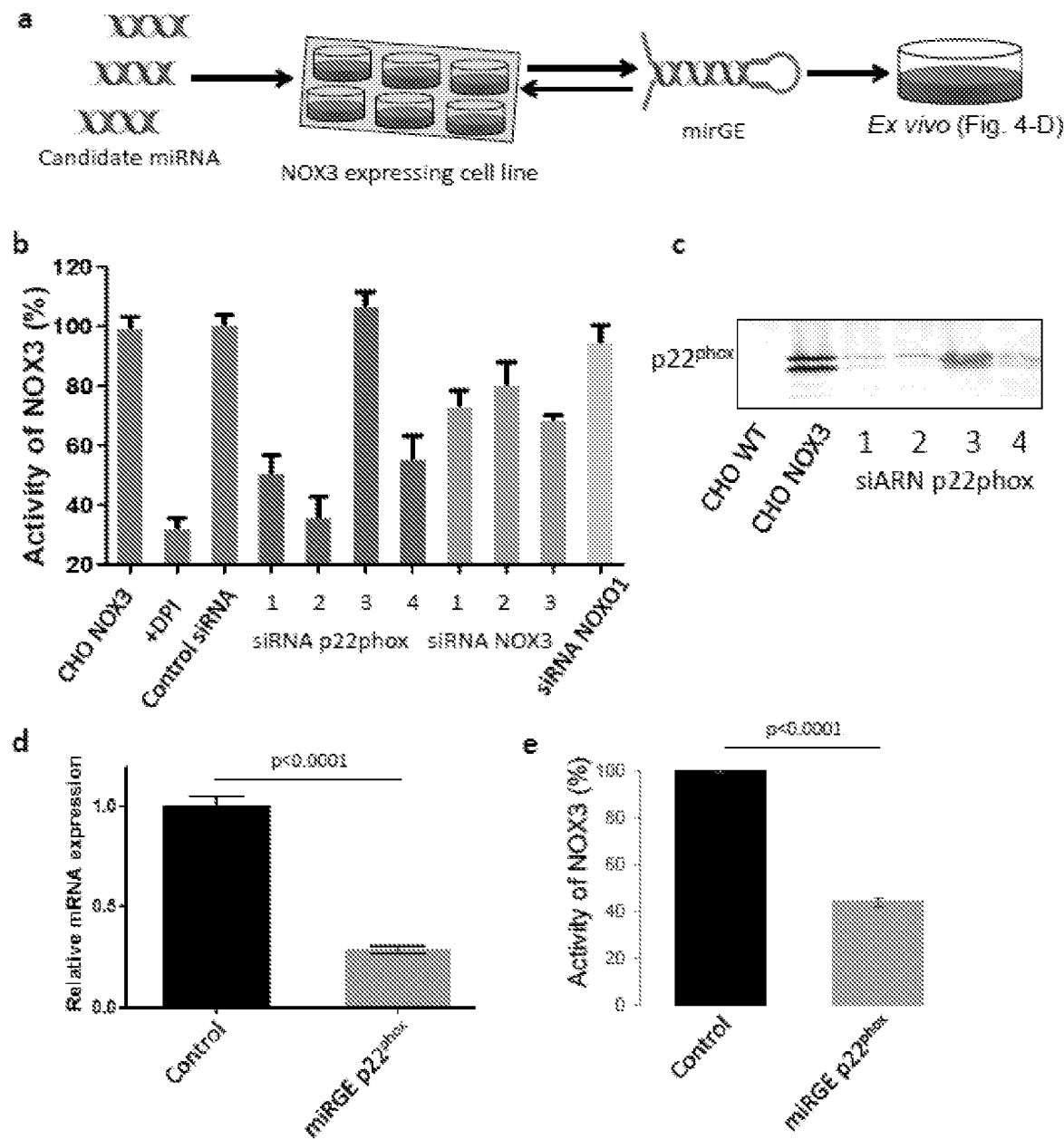
FIG. 8: Overall strategy for the design of efficient miRGE concatenate targeting NOX3 activity. (a) Candidate siRNA sequences are design of in silico and selected on their ability to knock-down the target mRNA (NOX3, p22$^{phox}$ or NOXO1). The most active siRNA sequence is then cloned in the miRGE backbone to construct the SMIG. Validation of the SMIG efficiency is verified on the same target expressing cell line. (b) Potency of 8 siRNA candidates, targeting mRNA encoding for the NOX3 complex (NOX3, p22$^{phox}$ and NoxO1) were assessed with respect to NOX3 activity by the amplex red method. (c) Effect of the most efficient sequence (targeting p22$^{phox}$) on NOX activity was verified by Western Blot. (d-e) Efficiency of the triple hairpin concatenate SMIG designed with the most active siRNA sequence was checked on the NOX3 expressing cell line either by QPCR (d) or by measurement of the production of ROS (e).
FIG. 9: Calculation of the efficiency of concatenation of the miRGE hairpins. (a) Table showing the formula allowing the calculation of the efficiency of concatenation (E) for GFP, MGST2 and H2B spacers. For the calculation of the concatenation efficiency, CCR5 knockdown with a single miRGE hairpin (knock-down potency (KP)) and with triple miRGE concatenate (concatenation potency (CP)) were considered. (b) Table summarizing the knock-down potency (KP), the concatenation efficiency (E) and their product, the general vector efficiency. (c) The former one is also displayed on the histogram.

The spacer sequence determines the additive effects of miRNA hairpin concatenation. To confirm the role of the spacer sequence in the concatenation potency of the vector, multi-hairpin constructs were designed with different spacers: GFP, GFP2, MGST2 or H2B (FIG. 3a). When the GFP or GFP2 sequence was used as a spacer, the concatenation of three hairpins dramatically enhanced CCR5 knockdown compared to a single hairpin construct (from 60% to 85% CCR5 knockdown) (FIGS. 3b and 3c). When MGST2 was used as a spacer, substantially different results were obtained. With a single hairpin, the MGST2 sequence had a good spacer activity, albeit not as potent as the GFP sequence (FIG. 2). No additive effect of a three-hairpin concatenation was observed, however, with MGST2 as the spacer (concatenation efficiency close to 1) (FIG. 3c). Thus, there is a dissociation between the spacer potency with a single hairpin, as compared to the concatenation activity. While the former is in a comparable range for GFP and MGST2, the latter is virtually absent with MGST2 as a spacer (FIG. 3c). The opposite was observed with H2B as a spacer: a rather poor knockdown was observed with a single hairpin (~10%), while there was an improved concatenation effect as judged by the CCR5 knockdown with the triple hairpin construct (40% knockdown) (FIGS. 3b and 3c). To investigate whether this observation also applies to hairpins targeting genes other than CCR5, a triple hairpin SMIG was constructed, targeting the NOX subunit p22$^{phox}$ (CYBA) with either MGST2 or GFP as spacer sequences (FIGS. 3d and 3e; see also FIG. 7). These constructs were used to transduce the promyelocytic leukemia cell line PLB-985, which upon differentiation towards a neutrophil-like phenotype, expresses all phagocyte NADPH oxidase subunits (including NOX2 and p22$^{phox}$/CYBA) and produces reactive oxygen species (ROS) through this NADPH oxidase. There was a 50% decrease in the CYBA mRNA level using the MGST2 spacer/triple hairpin constructs, while with a GFP spacer CYBA mRNA knockdown was >80% (FIG. 3d). Functional activity of the phagocyte NADPH oxidase was asssessed, namely ROS generation (FIG. 3e). The production of ROS was inhibited by 60% with the GFP-triple hairpin concatenate targeting p22$^{phox}$. In contrast, by replacing GFP with MGST2 as a spacer, ROS production was inhibited by no more than 20%. These data confirm that, although efficient knockdown is seen with a single hairpin, the MGST2 spacer has poor concatenation activity (FIG. 3c and FIG. 8). These experiments demonstrate that the spacer sequence is not only required for the knockdown efficiency with a single hairpin but is also required for the additive concatenation effect—the concatenation potency.

Figure 4:
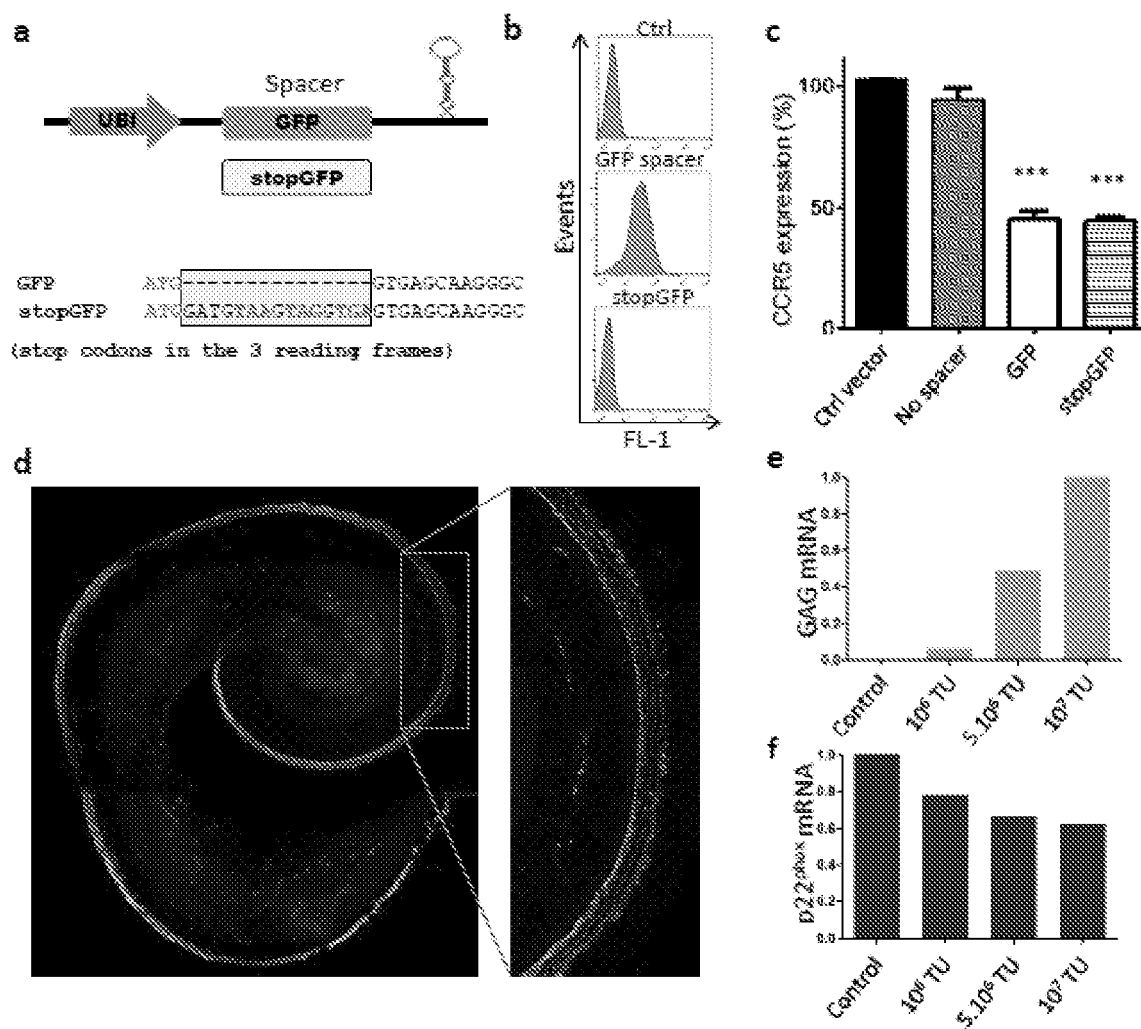
FIG. 4: Translation-independent activity of the GFP spacer in cell lines and tissue explants. (a) Design of the stopGFP spacer, harboring stop codons in all possible reading frames of the GFP cDNA in 3' of the initiation codon (ATG). (b) HeLa R5 Cells were transduced at >1 MOI with both coding and noncoding forms of GFP. FACS histograms show the fluorescence of GFP in transduced cells. The GFP fluorescence of cells transduced with the stopGFP construct was comparable to the control (non-transduced HeLa cells). (c) The spacer activity of stopGFP sequence was also assessed by FACS on CCR5 expression after 0.2 MOI transduction in HeLa R5 cells. The histogram shows the expression of CCR5 of the transduced population relatively to the untransduced population as assessed by FACS immunostaining. Data represent the mean+/− SEM of three independent experiments. (d) Organotypic culture of newborn rat cochlear explants transduced with increasing amounts stopGFP triple miRGE hairpin concatenate targeting p22$^{phox}$ ($10^6$ to $10^7$ vector particles). Hair cells are stained for myosin 7a (in green) and efficiently transduced cells express the marker gene mCherry (red). After five days in vitro, expression of the viral gene GAG (e) and p22$^{phox}$ (f) was assessed by qPCR. TU=transducing units.

Translation-independent activity of the GFP spacer in cell lines and tissue explants. Among the tested candidates, the GFP sequence was most efficient as a spacer, both with respect to knockdown potency with a single hairpin and concatenation potency. Other coding sequences also yielded some significant knockdown activity, though the CD4 intron was inactive. A construct harboring stop codons in each possible reading frame was generated in order to test whether protein translation of GFP was required for optimal functioning of the SMIG (FIG. 4a). No fluorescence was detected in the cells transduced with stopGFP (FIG. 4b). The CCR5 knockdown achieved with the stopGFP spacer was comparable to knockdown with the standard GFP spacer (~50% with a single hairpin construct). These results show that protein translation of the spacer is not important for the function of SMIG, and they provide highly efficient spacer which does not lead to translation of the xenogene GFP and is therefore compatible with a future clinical use.

To demonstrate the therapeutic potential of the optimized SMIG including the stopGFP spacer, knockdown of the inner ear NADPH oxidase NOX3 was investigated, a potential therapeutic application. This reactive oxygen species (ROS)-producing NADPH oxidase has been shown to be a relevant source of ROS leading to inner ear damage, and it is hence an attractive knockdown target for inner ear protection[26]. A triple miRGE concatenate was designed, targeting the NOX3 subunit $p22^{phox}$, under the control of the UBI promoter, and with stopGFP as a spacer. To identify transduced cells, the mCherry coding sequence under the control of the PGK promoter was also included in the construct. Newborn rat cochlear explants were transduced with this construct (FIG. 4d). A dose response for vector transduction using RT PCR to detect and quantify the lentiviral GAG gene (FIG. 4e). Transduced cells could also be identified by mCherry red fluorescence (FIG. 4d; green fluorescence is a marker for hair cells). A minority of hair cells were transduced with the vector under the experimental conditions, but results showed a dose-dependent decrease in $p22^{phox}$ mRNA, confirming the efficiency of the miRGE vector with a second clinically relevant target gene (FIG. 4f).

Figure 5:
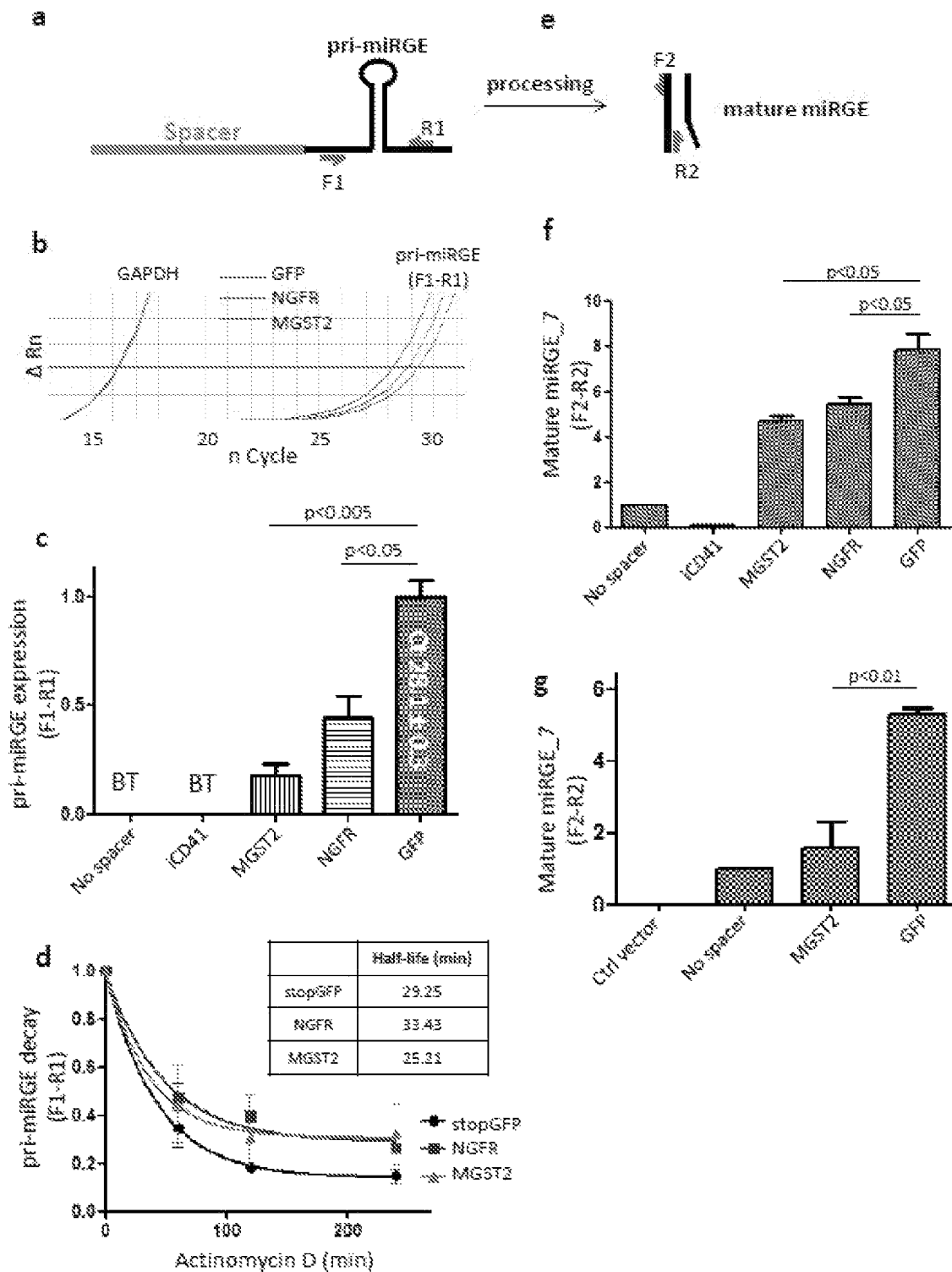
FIG. 5: The spacer sequence regulates the steady state levels, but not the half-life of miRGE. HeLa expressing CCR5 were transduced with single hairpin vector with GFP, LNGFR, MGST2 or iCD41 as spacers. (a) Unprocessed (pri-miRGE) or (e) mature miRGE level was assessed by qPCR using primers matching the flanking region of pri-miRGE (F1-R1) or the targeting strand of the mature miRGE (F2-R2). (b) Representative qPCR amplification plot of unprocessed miRGE level with GFP, NGFR and MGST2 as spacers. Note that without spacer or with iCD41 as spacer, miRGE level was below detection threshold. GAPDH was used as housekeeping gene. ΔRn of 0.2 was defined as the threshold (red line). (c) Bar graph shows the relative level of unprocessed miRGE as averaged from three independent experiments. The highest value of miRGE expression, normalized to 1.0 corresponds to a Ct value of 28.1±0.3. BT=below detection threshold. (d) Transcription was blocked with Actinomycin D at different time point (0-240 min) and effect of the spacer was assessed on unprocessed miRGE half-life. Graph shows the relative miRGE decay over time and half-life for each spacer is displayed in the table. (f and g) Comparison of the steady state level of the mature miRGE as assessed by qPCR from HeLa cells transduced with single hairpin (f) or triple hairpin concatenates (g) with different spacers. Data represent the mean+/− SEM of three independent experiments.
Figure 11:
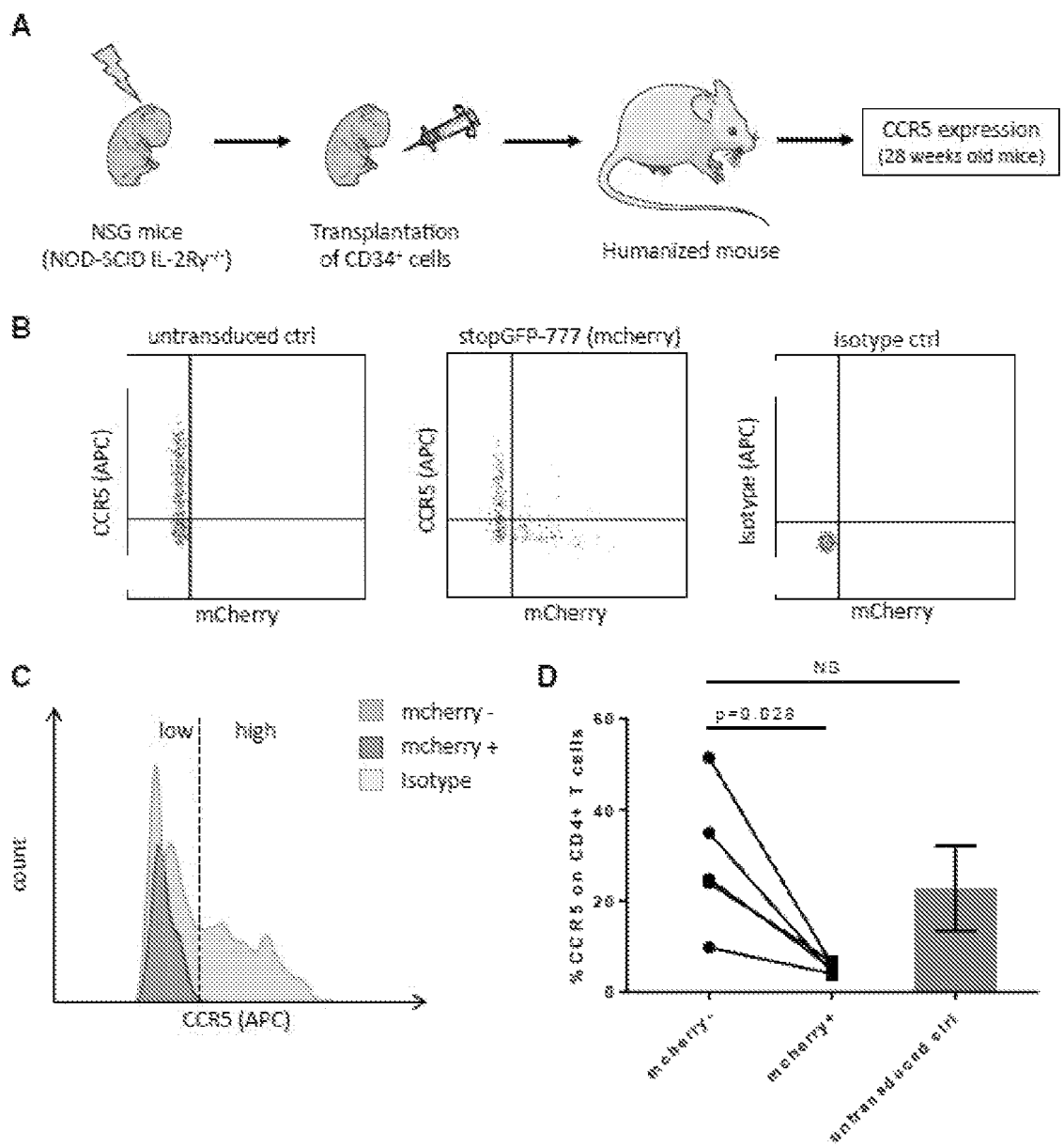
FIG. 11: Optimized minigene architecture allows sustained in vivo knockdown of CCR5 in circulating cells. (A) Six NGS newborn mice were engrafted with 260,000 human CD34+ hematopoietic stem cells (HSCs), following transduction with triple hairpin concatenate targeting CCR5. At the age of 28 weeks, blood was harvested for analysis of CCR5 expression. (B) FACS plots showing CD4+ T cells from mice transplanted with non-transduced HSC (left) or transplanted with stop GFP-777 transduced HSC (center). Right plot shows CD4+ T cells stained with irrelevant antibody (untransduced HSC). mCherry+ cells indicate effectively transduced cells. (C) Histogram showing expression level of CCR5 in transduced (mCherry+) and remaining untransduced (mCherry_) CD4 T cell population for a single transplanted mouse, relative to irrelevant antibody (isotype). Cells on the right of the dotted line represent high CCR5-expressing CD4 T cells. (D) Comparison of the CCR5 expression level in high CCR5 CD4+ T cells population in five engrafted mice. Untransduced ctrl stands for mice engrafted with non-transduced human CD34+ cells (n=3).
Figure 12:
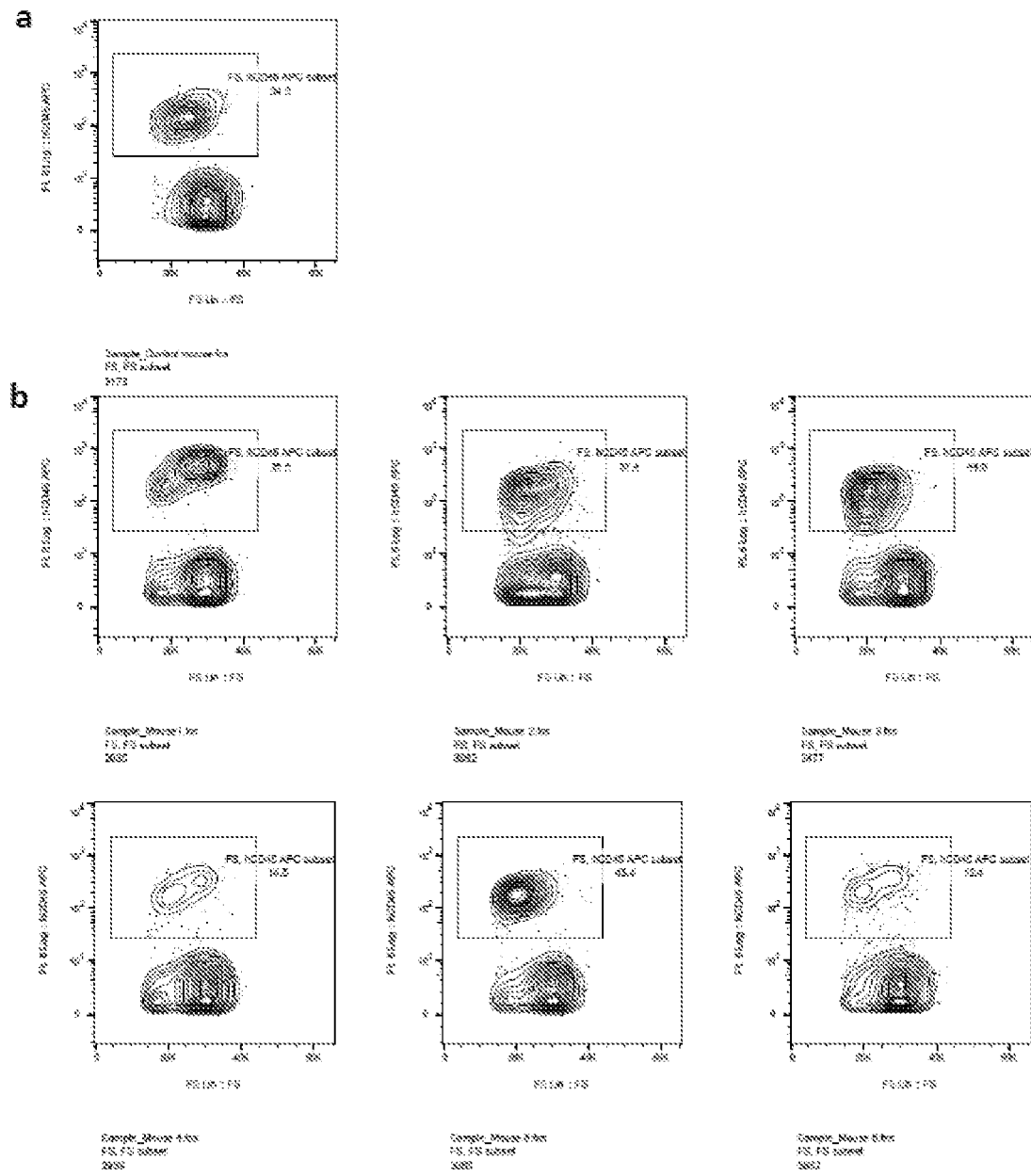
FIG. 12: Engraftment rate of human hematopoietic stem cells in NOD/SCID mice, 23 weeks following transplantation. FACS plot showing human circulating leukocytes expressing human CD45 marker in (a) a mouse transplanted with untransduced HSC or (b) the 6 mice transplanted with HSC transduced with the triple hairpin concatenate targeting CCR5. Engraftment rate is between 12.4% and 44%.
Figure 13:
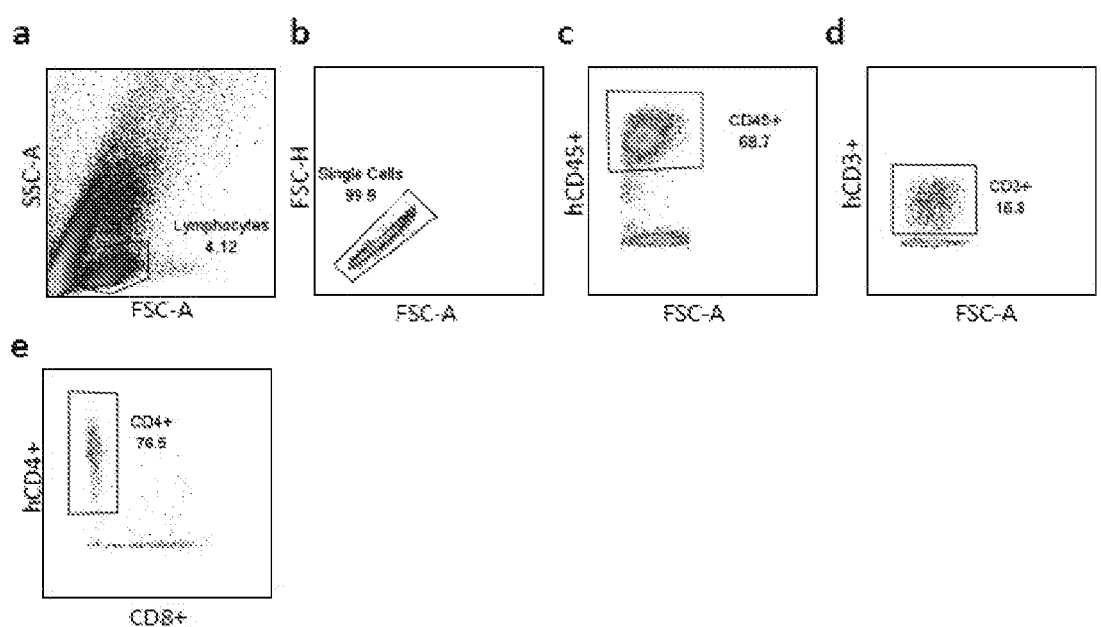
FIG. 13: Identification of human CD4+ T cells from the transplanted mice blood. Total lymphocytes were selected according to their FSC/SSC coordinates (a). Following doublet elimination (b), human leukocytes were selected with human CD45 staining (c), then human lymphocytes with human CD3 antibody (d). Finally, CD4+ T cells were discriminated from CD8+ T cells with human CD4 and human CD8 antibodies (e).

Sustained miRNA-mediated knockdown of CCR5 in circulating leukocytes derived from human hematopoietic stem cells: To further demonstrate the in vivo efficacy and the therapeutic potential of the optimized SMIG including the stopGFP spacer, another promising clinical application was investigated, namely knockdown of the HIV co-receptor CCR5 in vivo (FIG. 11). For this purpose, human CD34+ hematopoietic stem cells (HSCs) were transduced with a triple miRGE concatenate, targeting CCR5, under the control of an elongation factors promoter, and with stopGFP as a spacer. To identify transduced cells, the mCherry coding sequence under the control of the PGK promoter was also included in the construct. After transduction, HSCs were engrafted in NGS (NOD scid gamma) mice following irradiation (FIG. 11A), achieving an engraftment rate varying between 12.4% and 44%, after 23 weeks (FIG. 12). 28 weeks following the engraftment, CCR5 expression was investigated in the circulating blood (FIGS. 11; 13). The results revealed two kinds of CD4+ T cells with respect to CCR5 expression in untransduced control and mCherry-negative cells (FIGS. 11B and 11C). The proportion of high CCR5-expressing CD4 T cells varied from less than 10% to more than 50% with an average close to 25% in five of the six engrafted animals (FIG. 11D, see mCherry and untransduced ctrl). Note that in one of the six engrafted animals, the high CCR5 CD4 T cells population was virtually absent and therefore not taken into account in FIG. 11D. Importantly, a dramatic decrease of the CCR5 expression level was observed in the mCherry+ transduced population (FIG. 5D, mCherry+).

The spacer sequence regulates the steady state levels, but not the half-life of miRGE. PCR primers were designed to quantify unprocessed miRGE hairpins (pri-miRGE) (FIG. 5a) or the mature miRGE (FIG. 5e). As seen in FIGS. 5b and c, relative expression of the miRGE pri-miRNA was significantly stronger in cells transduced with the stopGFP spacer than in the cells transduced with the MGST-2 or NGFR-based vector. Note that miRGE expression was below the detection threshold with the CD4 first intron as spacer, as also seen in the absence of a spacer. To investigate whether this increase in the steady state levels of miRGE was due to a prolonged half-life of the transcript, HeLa R5 cells were treated with Actinomycin D for different time periods to block transcription (FIG. 5d). mRNA was harvested and miRGE expression levels assessed by qPCR of the pri-miRGE at the different time points. Results showed an estimated mirGE half-life of approximately 30 min with the stopGFP spacer (FIG. 5d), similar to that seen with the NGFR and MGST spacers. The steady state level of the mature miRGE demonstrated that stopGFP spacer allows the best expression of the mature miRGE (FIG. 5f). This observation was also valid when comparing stopGFP and MGST2 spacers with triple hairpin concatenates (FIG. 5g). Interestingly, both levels of precursor and mature miRGE were similarly impacted by the spacer sequence. These results strongly suggest that spacer activity is not linked to stability of miRNA transcript nor processing. Rather these results suggest a mechanism where the spacer is relevant for the transcription of the SMIG.

Figure 6:
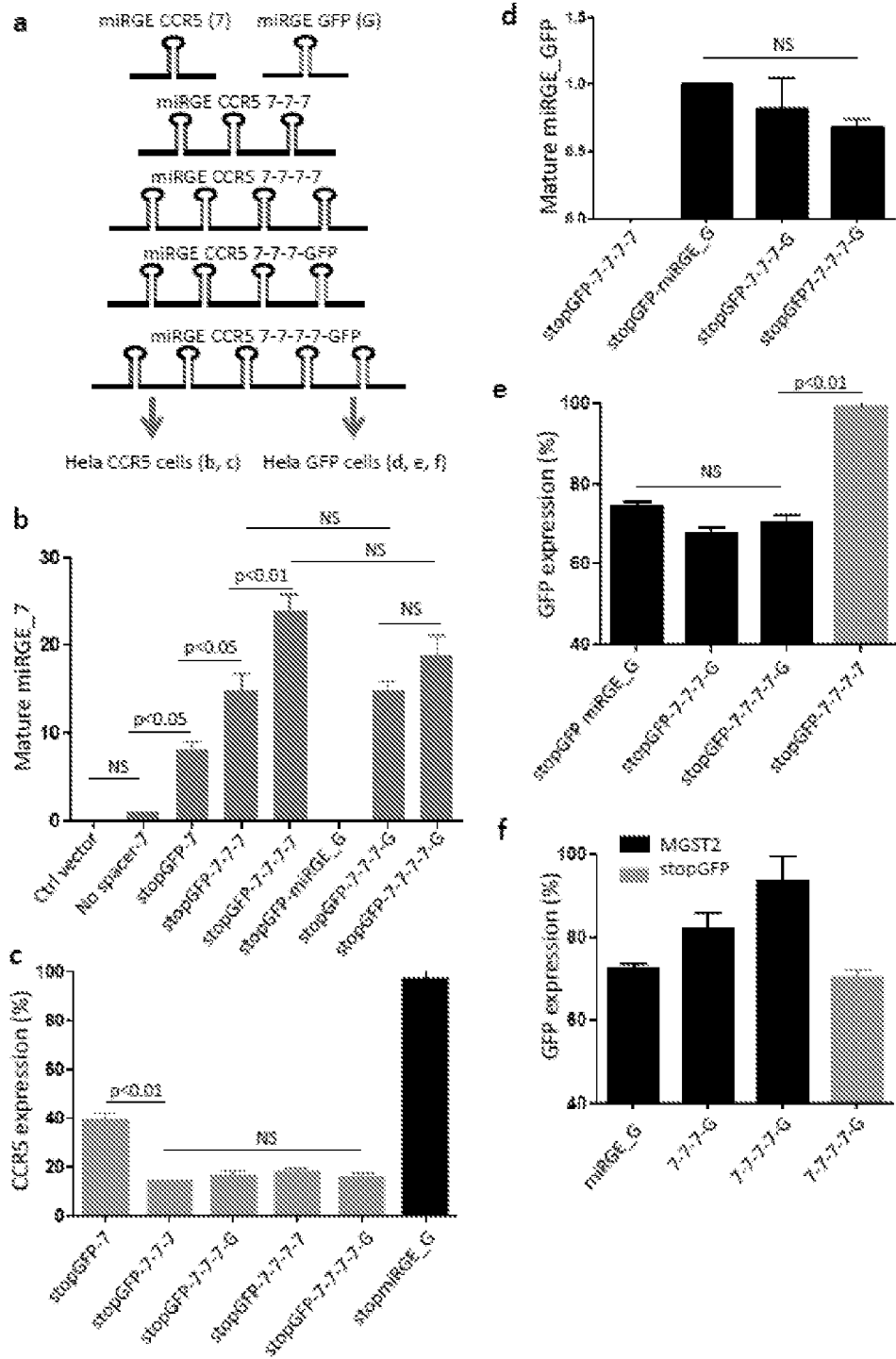
FIG. 6: Maximizing concatenation and achieving multi-target knock-down. (a) Efficiency of the stopGFP triple concatenate targeting CCR5 (mirGE 7-7-7) was compared to constructs harboring a fourth or a fifth hairpin either targeting CCR5 or a second target—GFP. Bar graphs show the steady state level of the mature miRGE targeting CCR5 (7) (b) or targeting GFP (G) (d), as assessed by qPCR and the ability of these constructs to knockdown CCR5 expression (c) or GFP expression (e) in HeLa cells. Vector expressing a single miRGE hairpin targeting CCR5 or GFP were used as controls. (f) When replacing the stopGFP with MGST2 as spacer, activity of the fourth and the fifth hairpin was decreased, as compared to the single miRGE hairpin control (miRGFP) or to the fifth hairpin of the stopGFP construct. Data represent the mean+/−SEM of three independent experiments.

Maximizing concatenation and achieving multi-target gene knockdown. To further investigate the possibility of a multi-target gene knockdown vector with a single promoter-driven miRNA cluster, a fourth and a fifth mirGE hairpin, either targeting CCR5 or a second target gene (GFP in this case), was added to the triple CCR5 construct (FIG. 6a). Concatenation of the hairpins led to a significant increase of the mature miRGE steady state level as a function of the number of hairpins present in the concatenate (FIG. 6b). Interestingly, the addition of a fourth hairpin targeting CCR5, while leading to the highest mature miRGE level, did not provide additional decrease in CCR5 expression compared to the triple hairpin construct arguing for a possible saturation of the CCR5 target sites with the miRGE (FIG. 6c). On the other hand, when the fourth hairpin was replaced with a hairpin targeting GFP, not only did CCR5 knockdown remain at its maximum level (~90%), but there was also a significant decrease in GFP fluorescence (FIG. 6c). Thus, while the hairpin in the fourth position did not further enhance CCR5 knockdown, it was clearly still efficiently processed, as witness by the GFP knockdown (FIG. 6d) and the mature miRGE-GFP steady state level (FIG. 6e). Interestingly, a fifth hairpin targeting GFP displayed similar knockdown efficiency and level of mature miRGE as the fourth, still without affecting knockdown of the CCR5. More importantly, miRGE_GFP steady state levels as well as GFP knockdown mediated by the fourth or the fifth miRGE hairpins was comparable to knockdown achieved with a single miRGE hairpin targeting GFP. Thus, with UBI as promoter and stopGFP as spacer, there was no loss of activity with up to five concatenated hairpins. However, the efficiency of the five-hairpin concatenation strongly depended on the spacer. Indeed, the use of MGST2 as spacer led to a dramatic decrease of the fourth and fifth hairpin GFP knockdown potency (FIG. 6f). These data demonstrate that optimized SMIG architecture allows for efficient multi-target gene knockdown upon a single promoter-driven, multi-hairpin construct.

Example 3—Prophetic Synthetic Minigenes for Immune Checkpoint Knockdown

Figure 10:
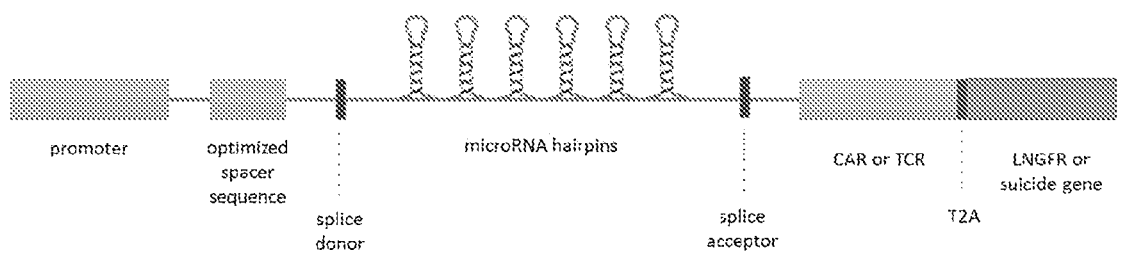
FIG. 10: Schematic of prophetic synthetic minigene to generate re-directed immunotherapeutic cells with intrinsic immune checkpoint knockdown. Promoter selected to allow tissue specific expression, while the spacer sequence and length is optimized to allow expression of all miRNA hairpins. The miRNA hairpins may target a specific gene or gene(s) of interest while the CAR or TCR sequences allow the targeting of immunotherapeutic cells to specific antigens. T2A is a cleavage peptide site, and LNGFR allows for selection of engineered cells, while suicide genes would enable rapid removal of cells in case of toxicity.

Re-direction of immunotherapeutic cells with intrinsic immune checkpoint knockdown. Depicted in FIG. 10 is a schematic of a prophetic synthetic minigene which may be used to knockdown immune check points. The synthetic minigene is comprised of a promoter sequence, spacer sequence, at least 2 miRNA hairpins, and a chimeric antigen receptor sequence or T cell receptor sequence. The synthetic minigene may optionally comprise a selection sequence, such as a low-affinity nerve growth factor receptor (LNGFR) or suicide gene sequence. Further, in order to express the miRNA hairpins, CAR or TCR sequence, and selection sequence equally, the CAR or TCR sequence may be separated from the selection sequence by a "cleavable peptide" such as a 2A sequence, or T2A sequence. These synthetic minigenes may comprise miRNA hairpin sequences directed to any immune checkpoint. Specifically, the miRNA hairpin sequences may target PD1, CTLA4, LAG3, TIM3, TIGIT, CD96, BTLA, KIRs, adenosine A2a receptor, Vista, IDO, FAS, SIRP alpha, CISH, SHP-1, FOXP3, LAIR1, PVRIG, PPP2CA, PPP2CB, PTPN6, PTPN22, CD160, CRTAM, SIGLEC7, SIGLEC9, CD244, TNFRSF10B, TNFRSF10A, CASP8, CASP10, CASP3, CASP6, CASP7, FADD, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, PRDM1, BATF, GUCY1A2, GUCY1A3, GUCY1B2, and GUCY1B3 mRNA. The promoter used may be any mammalian promoter, such as EFs or UBI, or any promoter listed in Table 1. The spacer sequence may be any length or sequence, particularly one of the spacers listed in Table 9. Any immune effector cell may be targeted with these miRNA expression constructs. Specifically, T cells, tumor infiltrating lymphocytes (TILs), TCR-engineered T cells, CAR T cells, NK cells, or T regulatory cells may be engineered with the synthetic miRNA constructs.

Tumor infiltrating lymphocytes with intrinsic immune checkpoint knockdown may be generated using the synthetic minigenes provided herein. To generate these TILs with immune checkpoint knockdown, TILs may be isolated from the patients' tumor tissue and purified. These purified TILs may be transduced with a lentiviral vector comprising a therapeutic minigene harboring miRNA hairpins directed to immune checkpoint mRNAs in order to knock down the gene expression of one or more immune checkpoints. Then, the modified TILs may be expanded ex vivo, and finally re-introduced to the patient.

CAR T cells or TCR engineered T cells with intrinsic immune checkpoint knockdown may be generated similarly to TILs. T cells can be collected from patients by leukapheresis. The collected cells may then be transduced with a single vector comprising the miRNA hairpins targeting the immune checkpoint mRNAs as well as the CAR or engineered TCR sequence. Having these in a single vector, as shown in FIG. 10, allows for a more efficient turn-around time from T cell collection to patient treatment. Alternatively, the collected T cells may be treated with two separate vectors. The first vector may comprise the CAR or engineered TCR sequence, and may be transduced or transfected into the cells. The second vector then comprises a lentivector harboring the miRNA expression construct with the miRNA hairpins targeted to the immune checkpoint mRNAs. Following transduction of the second vector, these modified T cells may be expanded ex vivo and later re-introduced to the patient.

Example 4—Synthetic Minigenes Target Gene Knockdown

Figure 14:
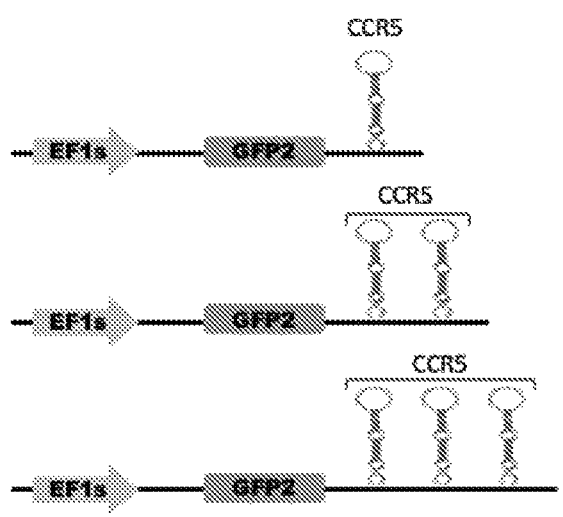
FIG. 14: Efficiency in CCR5 downregulation using 1-3 hairpin mirGE constructs against CCR5. (A) Architecture of therapeutic minigenes showing 1-3 hairpins, with each being identical and targeting CCR5; (B) Aligned flow cytometric histograms demonstrating the decrease in fluorescent intensity within transduced HeLaR5 cells (mCherry positive populations); (C) Relative CCR5 expression levels when compared to HeLaR5 cells transduced with mCherry only control vector (n=3).
Figure 14:
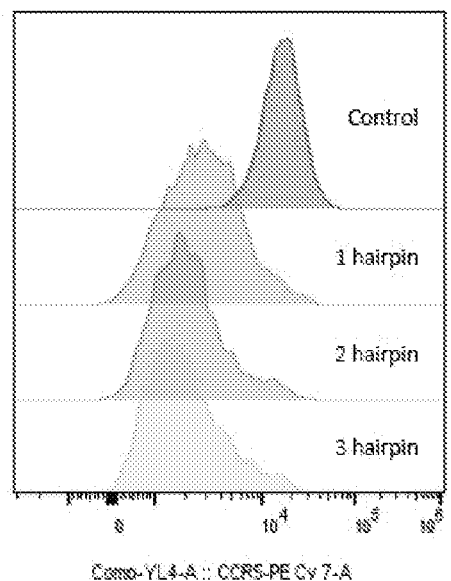
Figure 14:
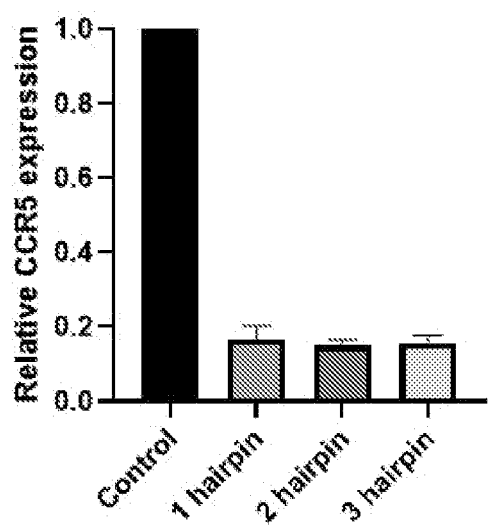

Single and Double Hairpin mirGE Constructs Knockdown CCR5 with High Efficiency in HeLaR5 Cells Using an optimized therapeutic minigene architecture (EF1s promoter, GFP2 spacer, single and double CCR5-targeting mirGE hairpins were constructed to evaluate how efficiently they could downregulate CCR5 relative to our established three-hairpin construct (FIG. 14). HeLaR5 cells were transduced with lentiviral vectors carrying the constructs at a MOI of 1.0, and CCR5 downregulation measured 5-7 days following transduction. All constructs also carried an mCherry reported gene to identify transduced cells. CCR5 knockdown was measured via flow cytometry by measuring the MFI of transduced cells (mCherry positive) vs untransduced cells within the same sample, and this ratio compared relative to HeLaR5 cells transduced with a control lentiviral vector to express mCherry only.

Results indicated high efficiency downregulation of CCR5 with all three constructs, as demonstrated by significant reductions in MFI and an overall shift in fluorescent intensity when compared to cells transduced with the control vector (FIG. 14B). Relative CCR5 expression levels were 16.5%, 15% and 15.7% (mean of n=6) for the single, double and triple hairpin constructs, respectively. Notably, maximal CCR5 knockdown in HeLaR5 cells can be achieved with a single mirGE hairpin when using the our optimized therapeutic minigene architecture (EF1s promoter, GFP2 spacer).

High Efficiency Knockdown of PD1 in Primary T Cells

Considering the central role that PD1 plays in T exhaustion, and more broadly in the field of engineered T cell therapies, a therapeutic minigene was developed that would maximally downregulate PD1. Three mirGE constructs to silence PD1 were designed according the approach described previously (Myburgh et al., 2014, incorporated herein by reference). Target sequences were identified using online software tools, including i-Score Designer, BLOCK-iT (ThermoFisher), GeneScript siRNA Target Finder, and siDESIGN Center (Dharmacon). Based on the scoring of these tools, a list of top 10 target sequences was generated. The target sequences were then each screened for homology across the human genome using BLAST, and those with >70% homology to any other gene were excluded. Finally, three target sequences were selected (Table 10) for cloning into the mirGE and our optimized therapeutic minigene architecture (EF1s promoter, GFP2 spacer). Once constructed, the three minigenes were packaged into lentiviral vectors and used to transduce primary T cells from two healthy donors at a MOI of 1.0 and 2.5. All constructs also carried a mCherry reported gene to identify transduced cells. PD1 expression levels were measured 5-7 days after transduction using flow cytometry. Since PD1 is not expressed uniformly, nor constitutively on primary T cells, we first determined the percentage of PD1-expressing T cells, and then compared the MFI of the PD1-expressing cells relative to control transduced (mCherry only) T cells.

TABLE 10

PD1 target sequences

| Identifier | Target sequence |
|---|---|
| PD1-1A (SEQ ID NO: 59) | CGGAGAGCTTCGTGCTAAA |
| PD1-2A (SEQ ID NO: 60) | CCAACACATCGGAGAGCTT |
| PD1-3A (SEQ ID NO: 61) | CCAGCAACCAGACGGACAA |

Figure 15:
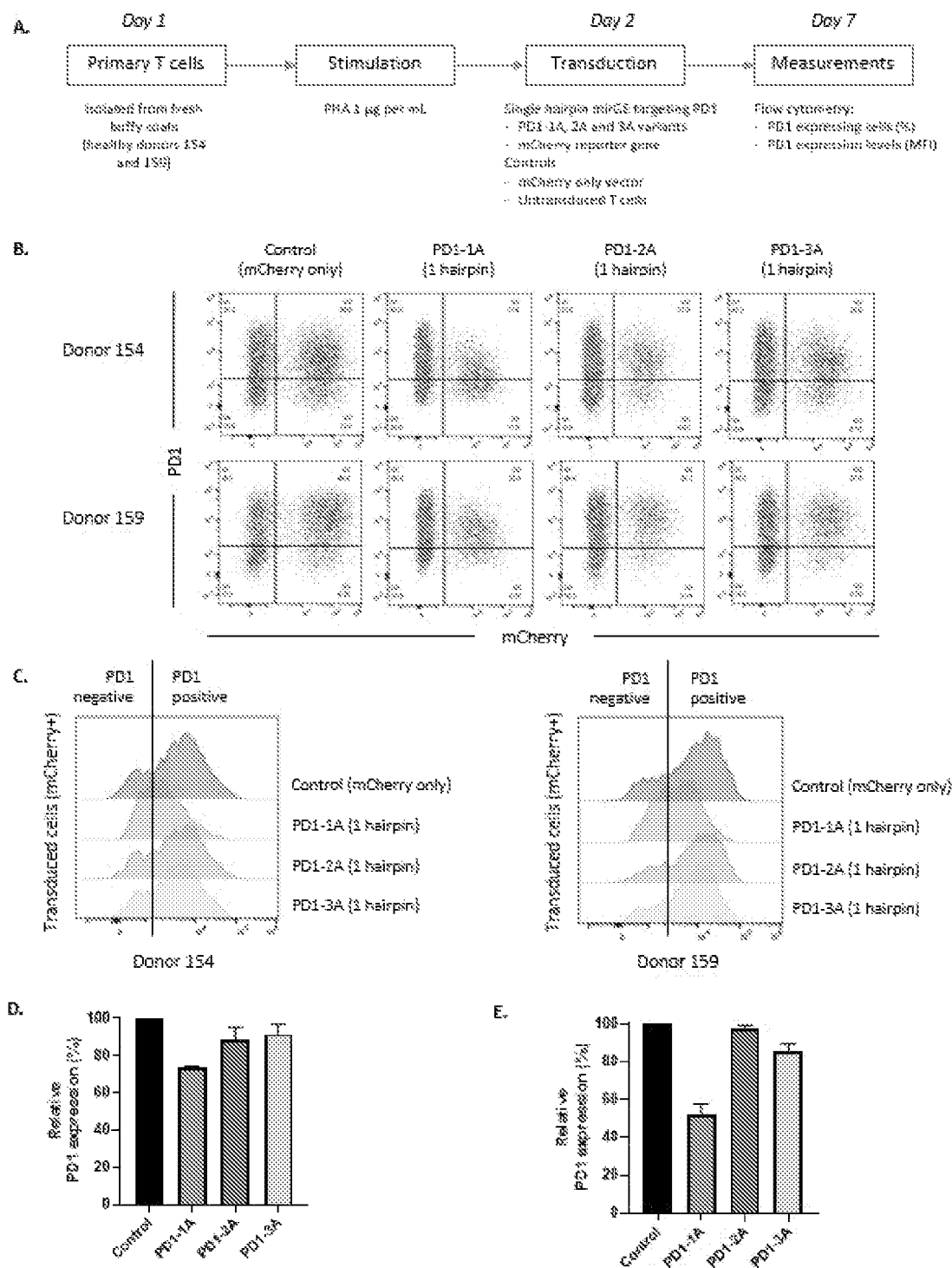
FIG. 15: Identification of the optimal target sequence for PD1 downregulation. Three PD1 target sequences, identified based on in silico design, were used for construction of single hairpin mirGE therapeutic minigenes and packaged into lentiviral vectors for transduction of primary T cells according to the experimental plan shown in (A); (B-C) Flow cytometry dot plots and histograms indicating the PD1-1A construct to be most effective at decreasing PD1 expression in transduced T cell populations (mCherry+); (D-E) Bar graphs illustrating a relative reduction in PD1 expressing cells and expression levels (n=4).

The initial screen for target sequences which could be accessible for mirGE knockdown resulted in one of the three candidates showing significant effect (PD1-1A). As can be seen in examples of the flow cytometry dot plots and histograms (FIG. 15B-C), there was an evident shift in fluorescent intensity of cells transduced with PD1-A mirGE, which was not the case in T cells transduced with PD1-2A and 3A. PD1-1A transduced T cells had a mean reduction in PD1-expressing cells of 27% (FIG. 15D), while those transduced with PD1-2A and PD1-3A constructs had a 12% and 9% reduction (p=0.047, Kruskal-Wallis ANOVA). Moreover, within the PD1-expressing T cell population, there was a 48% reduction in PD1 expression in cells transduced with the PD1-1A construct (FIG. 15E), while T cells transduced with PD1-2A and 3A constructs had a 3% and 14% reduction (p<0.001, Kruskal-Wallis ANOVA).

Figure 16:
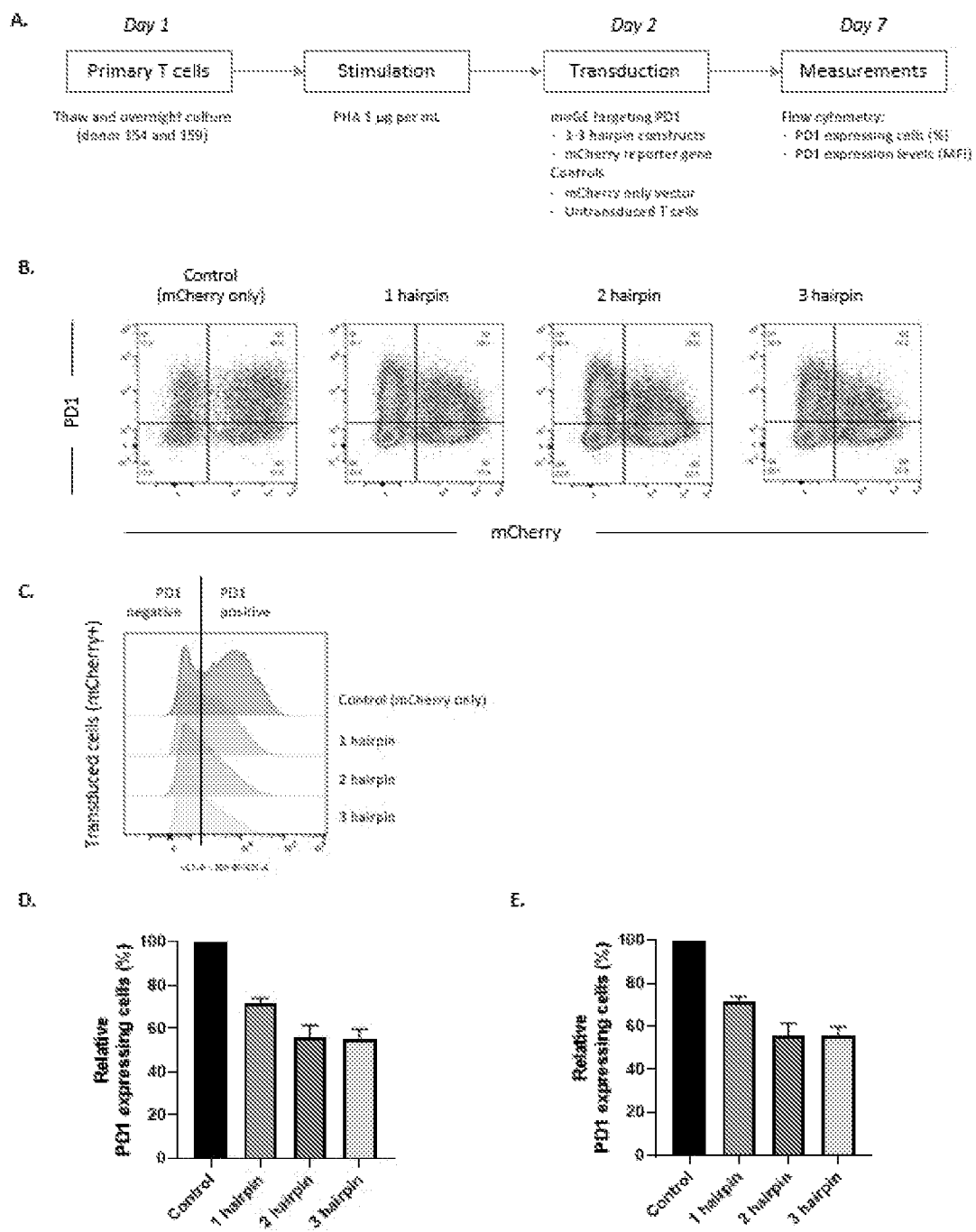
FIG. 16: PD1 downregulation with 1 to 3 hairpin mirGE therapeutic minigenes. After having identified a target sequence accessible for mirGE downregulation of PD1, two and three hairpin minigenes (same hairpin sequence) were constructed. The constructs were then packaged into lentiviral vectors for transduction of primary T cells from healthy donors (A); (B-C) Flow cytometry dot plots and histograms illustrating an increased knockdown of PD1 with 2 and 3 hairpin constructs when compared to the 1 hairpin construct; (D-E) Bar graphs illustrating the relative reduction in PD1 expressing cells and PD1 expression levels (n=3), indicating equivalent knockdown of PD1 using 2 and 3 hairpin constructs.

Thus, the PD1-1A mirGE was applied for further development of two and three hairpin constructs in an attempt to achieve maximal knockdown of PD1 (FIG. 16). Using T cells harvested from the same donor as used before, we transduced and evaluated PD1 knockdown according to the experimental plan shown in FIG. 16A. Flow cytometry data (FIG. 16 B-C) indicated that further PD1 downregulation can be achieved with two and three hairpin mirGE constructs, but that maximal knockdown was achieved with two hairpins (since there was a negligible difference when using the three hairpin construct). Both the two and three hairpin constructs reduced the proportion of PD1-expressing cells by 45% relative to the control vector, while also downregulating PD1 expression on the PD1-expressing cells by nearly 40% (FIG. 16D-E).

PD1 Knockdown in CAR T Cells Protects Against T Cell Exhaustion

To evaluate if PD1-targeting constructs would be protected against T cell exhaustion, anti-cKit CAR T cells transduced and co-cultured these cells with HL-60 tumor cells at effector:target (E:T) ratios of 1:15 and 1:30 over a four day period. A pure population of anti-cKit CAR T cells (previously selected) were thawed and transduced 24 hours later at a MOI of 1.0 with lentivectors carrying a three-hairpin mirGE therapeutic minigene against PD1. Co-culturing was initiated with 100,000 CAR T cells (anti-cKit with and without PD1 knockdown), and 1.5 million and 3.0 million HL-60 tumor cells added to achieve the 1:15 and 1:30 E:T ratios, respectively. A negative control group of CAR T cells only (not co-cultured with target cells) was also included. All conditions were cultured in medium not containing IL-2, made up with Advanced RPMI, 10% FBS, 1% pen-strep and 1× glutamax. After four days of co-culturing, cells were harvested for counting and flow cytometric analysis of PD1 expression on CD3 positive T cells.

Figure 18:
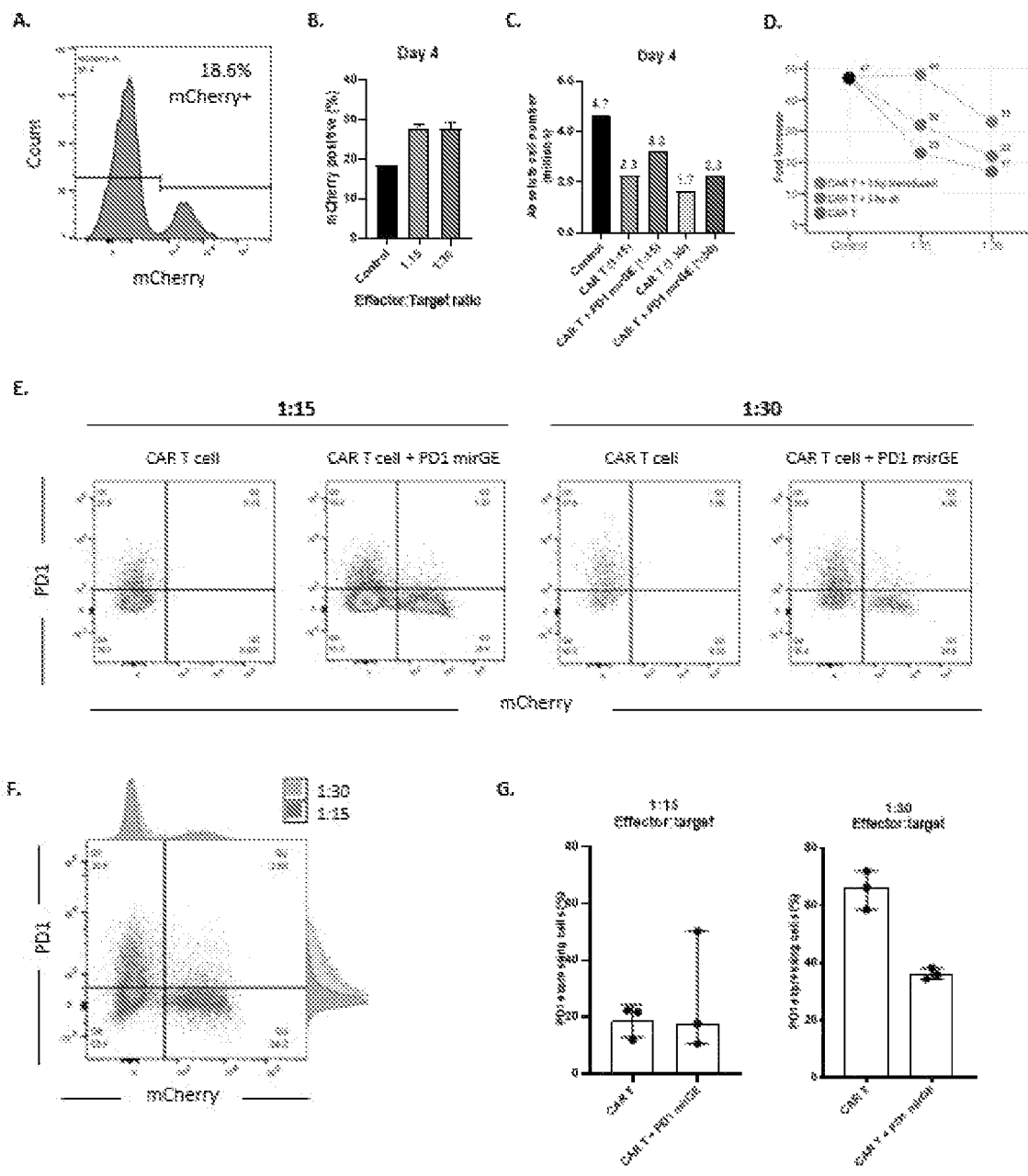
FIG. 18: Effect of PD1 knockdown in anti-cKit CAR T cells after a four day co-culture with HL-60 target cells. (A) Transduction rate of anti-cKit CAR T cells with a PD1 targeting mirGE (3 hairpin), based on mCherry positivity; (B) Increase in mirGE expressing CAR T cells on Day 4, based on mCherry expression; (C) Absolute cell numbers of anti-cKit CAR T cells after a four day co-culture with HL-60 target cells; (D) Fold increase of CAR T cells on over the four day co-culture period (starting with 100,000 CAR T cells on Day 1); (E-F) Flow cytometric dot plots, overlays and histograms of CAR T cells after the four day co-culture period; (G) Percentage of PD1-expressing CAR T cells.

A transduction rate of ~20% was achieved in the anti-cKit CAR T cells transduced with our PD1-targeting therapeutic minigene (based on mCherry positivity). On Day 4, the transduction rate was assessed again in the negative control group, which was reported to be 18.6% (FIG. 18A). When the proportion of mCherry positive cells was assessed in the 1:15 and 1:30 E:T ratio groups, there was a 1.5 fold increase (relative to the negative control, FIG. 18B), indicating that PD1 knockdown CAR T cells were proliferating at a higher rate than CAR T cells without PD1 knockdown. Negative control CAR T cells expanded from 100,000 to 4.7 million over the four day period (FIG. 18C). In the groups without PD1 knockdown, anti-cKit CAR T cells expanded to 2.3 million and 1.7 million at 1:15 and 1:30 E:T ratio conditions, respectively. In the groups that had ~20% PD1 knockdown CAR T cells at the outset, cell counts of 3.2 million and 2.3 million were recorded for the 1:15 and 1:30 E:T ratio conditions, respectively. Together with the fact that the proportion of mCherry positive cells increased 1.5 fold, it was therefore apparent that CAR T cells without PD1 knockdown were exhausted more rapidly, leading to a decrease in proliferation and/or cell death. These data were confirmed when we evaluated the fold increase for both E:T conditions and, specifically, for the mCherry positive CAR T cell population (based on the 1.5 fold proportion at Day 4). When compared to the anti-cKit CAR T cell group (without a ~20% PD1 knockdown sub-population), CAR T cells with PD1 knockdown had a proliferation rate of more than double at the 1:15 E:T ratio (23 vs 48-fold), and approximately twice at the 1:30 ratio (17 vs 33-fold).

PD1 knockdown in mCherry transduced CAR T cells was confirmed via flow cytometric analysis (FIG. 18E). As can be seen in the dot plots, the PD1-expressing population of CAR T cells is substantially decreased when compared to the untransduced CAR T cell population within the same sample (mCherry negative), as well as relative to the CAR T cell group that were not transduced with a mirGE therapeutic minigene. This effect was observed in both the 1:15 and 1:30 experimental groups, and which aligns with our PD1 knockdown data reported previously herein. When comparing the 1:15 and 1:30 E:T conditions with overlaid flow cytometric dot plots and aligned histograms (FIG. 18F), it became evident that CAR T cells in the 1:30 condition expressed an overall higher frequency of PD1 based on fluorescent intensity and PD1 expressing cells, providing indication that these CAR T cells were considerably more exhausted than those with PD1 knockdown. Finally, the percentage of PD1-expressing CAR T cells was evaluated from the two E:T conditions (FIG. 18G). At the 1:15 E:T ratio, both groups of CAR T cell had a median 20% PD1-expressing cells. Bearing in mind that PD1 knockdown CAR T cells made up ~28% of this population (having increased 1.5 fold over the four day period), it is apparent that these cells helped rescue the overall CAR T cell population within these samples. This rescue effect is more evident in the 1:30 condition, where nearly 70% of CAR T cells without PD1 knockdown were PD1 positive, but which decreased to below 40% in the group that started with ~20% CAR T cells with PD1 knockdown.

Multi-Target mirGE Hairpins Maintain Efficiency of CCR5 Knockdown

Figure 17:
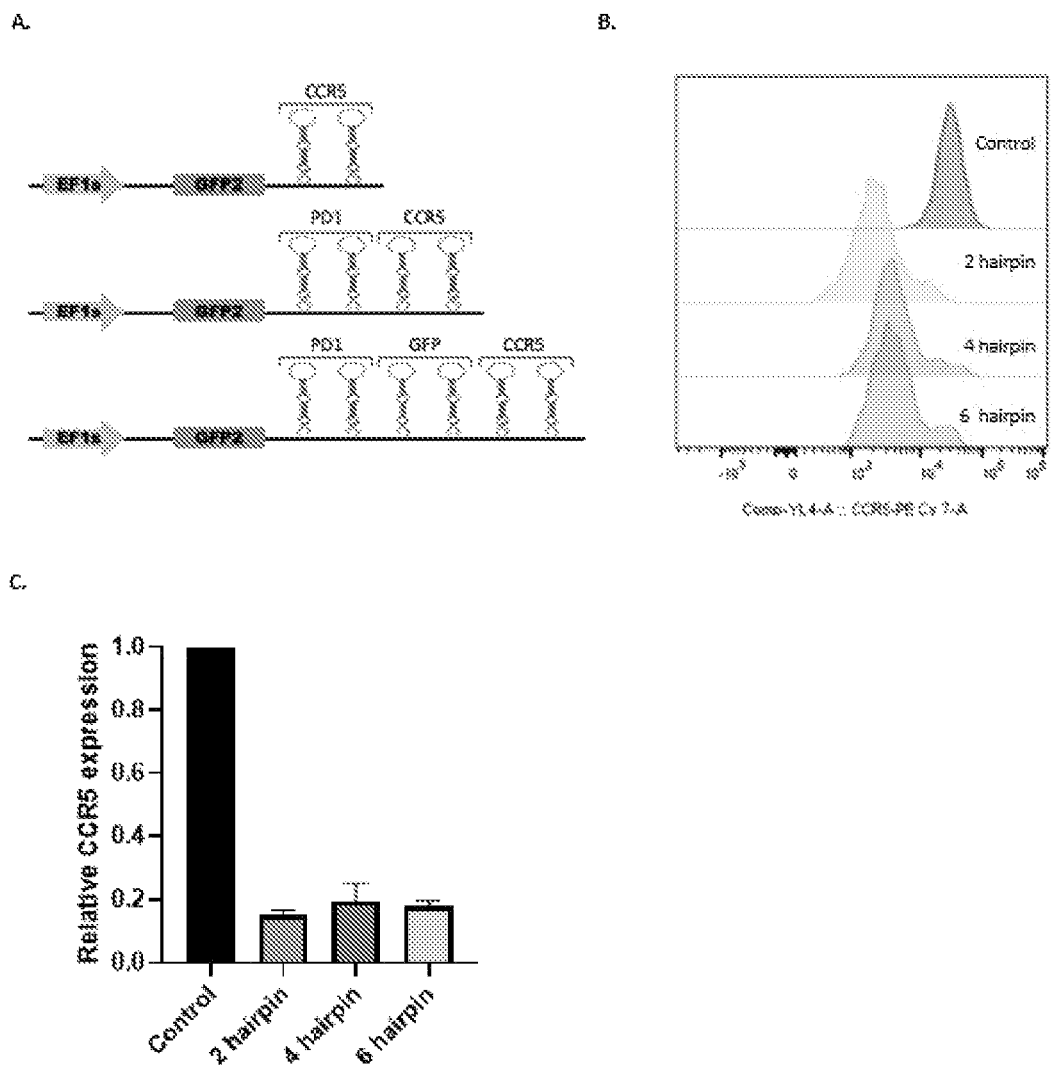
FIG. 17: Efficiency in CCR5 downregulation using mirGE constructs with two CCR5-targeting hairpins in terminal positions. (A) Architecture of therapeutic minigenes showing the position CCR5-targeting hairpins relative to PD1 and GFP-targeting hairpins; (B) Aligned flow cytometric histograms demonstrating a decrease in fluorescent intensity within transduced HeLaR5 cells (mCherry positive populations); (C) Relative CCR5 expression levels when compared to HeLaR5 cells transduced with mCherry only control vector (n=3 to 5).

To evaluate if up to six mirGE hairpins could be expressed with optimized therapeutic minigene architecture (EF1s promoter, GFP2 spacer), a multi-target hairpin construct against PD1, GFP and CCR5 was constructed (FIG. 17A). The potential impact of CCR5 knockdown if the mirGE targeting CCR5 were positioned terminally in the therapeutic minigenes was evaluated. Studies were undertaken to determine if there be a decrease in CCR5 knockdown if the CCR5-targeting hairpins were at positions 3 and 4 within a four-hairpin construct. Similarly, it was evaluated if placement of these hairpins in positions 5 and 6 impact CCR5 knockdown. In order to test this, HeLaR5 cells were transduced with these constructs and evaluated CCR5 downregulation relative to a two-hairpin CCR5 targeting vector as well as a control vector (mCherry only). CCR5 knockdown was evaluated using flow cytometry. Results indicated negligible differences in the downregulation of CCR5 (p=0.135, Kruskal-Wallis ANOVA), which was 85%, 81% and 82% for the two-hairpin, four-hairpin and six-hairpin constructs, respectively (FIG. 17B-C). These data, together with those showing the high efficiency of single-hairpin mirGE against CCR5 and PD1, substantiate the use of our therapeutic minigene technology for targeting at least two clinically relevant genes for downregulation.

Figure 19:
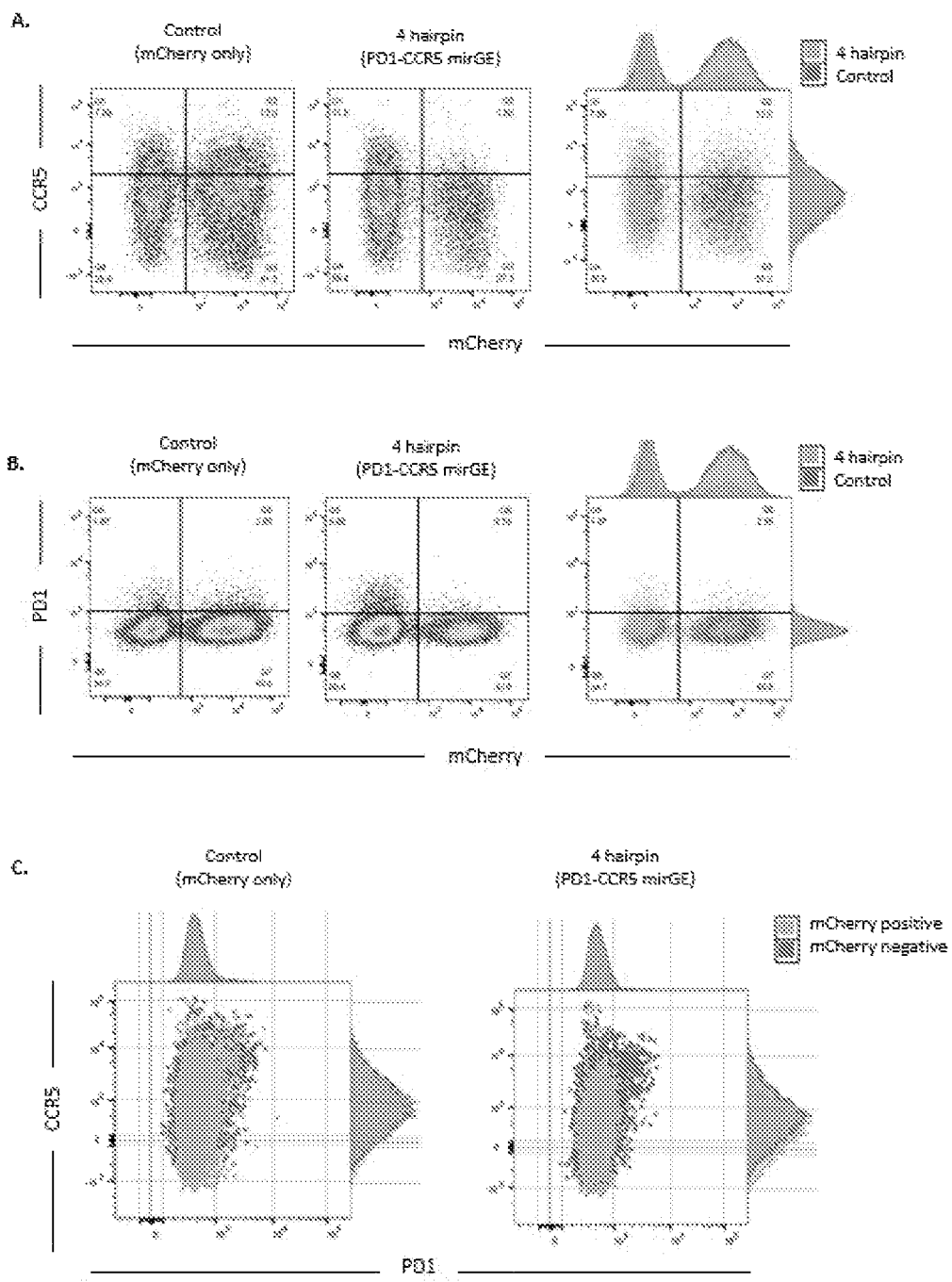
FIG. 19: Knockdown of CCR5 and PD1 in primary T cells. (A-B) Flow cytometric dot plots, overlays and histograms illustrating knockdown of both CCR5 and PD1 independently in primary T cells transduced with a 4 hairpin mirGE construct (two hairpins against PD1, followed by two hairpins against CCR5) and control vector (mCherry only); (C) Overlaid dot plots of CCR5 vs PD1 populations, gated on untransduced (mCherry negative) and 4 hairpin transduced (mCherry positive) T cell populations.

Four Hairpin Therapeutic Minigenes Effectively Downregulate PD1 and CCR5 in Primary T Cells Using a four-hairpin mirGE construct (two hairpins against PD1, two against CCR5), primary T cells were transduced as described before and evaluated for knockdown of these two clinically relevant target genes. Five days after transduction, PD1 and CCR5 expression was assessed via flow cytometry (FIG. 19). Indeed, a significant reduction in both PD1 and CCR5 expressing cells were observed. In the overlaid dot plots and histograms, a substantial decrease in CCR5 and PD1 was observed (FIGS. 19A and 19B). By plotting CCR5 vs PD1 and overlaying mCherry positive and mCherry negative populations (FIG. 19C), an evident decrease in the CCR5+PD1+ population was observed in T cells transduced with the 4 hairpin mirGE construct (notably exposing the CCR5+PD1+ population of untransduced T cells, i.e. dots in upper right decades of the dot plot). These data indicate that our mirGE therapeutic minigenes are able to efficiently knockdown the expression of two clinically relevant target genes.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Aiuti et al., *Science,* 341: 1233151, 2013.
Biffi et al., *Science,* 341: 1233158, 2013.
Boudreau et al., *RNA,* 14:1834-1844, 2008.
Boudreau et al., *Mol Ther,* 17:169-175, 2009
Bourhill et al., *J Virol Methods,* 235: 26-33, 2016.
Fowler et al., *Nucleic Acids Res,* 44: e48, 2016.
Giry-Laterriere et al., *Hum Gene Ther,* 22: 1255-1267, 2011.
Giry-Laterriere et al., *Methods in molecular biology,* 737: 183-209, 2011.
Grimm, Silence 2: 8, 2011.
Hu et al., *Mol Biotechnol,* 46: 34-40, 2010.
Jaquet et al., *Br J Pharmacol,* 164: 507-520, 2011
Lee et al., *Embo J* 23: 4051-4060, 2004.
Liu et al., *Nucleic Acids Res,* 36:2811-2824, 2008.
Liu and Berkhout, *Methods Mol Biol,* 942: 233-257, 2013.
Maczuga et al., *Mol. Ther.,* 21: 217-227, 2013.
Mottet-Osman et al., *J Virol,* 81:2861-2868, 2007.
Myburgh et al., *Molecular Therapy Nucleic Acids,* 3: e207, 2014.
Osorio et al., *J Biotechnol,* 169: 71-81, 2014.
Ruby et al., *Nature,* 448: 83-86, 2007.
Seyhan, *Mol Biosyst,* 12: 295-312, 2016.
Sibley et al., *Nucleic Acids Res,* 40: 9863-9875, 2012.
Stegmeier et al., *PNAS,* 102: 13212-13217, 2005.
Sullenger and Nair, *Science,* 352: 1417-1420, 2016.
Sun, D et al., *Biotechniques,* 41: 59-63, 2006.
Winter et al., *Nat. Cell. Biol.,* 11: 228-234, 2009.
Yang et al., *Mol Ther,* 21: 588-601, 2013.

What is claimed is:

1. A miRNA expression construct comprising, from 5' to 3', a promoter element, a spacer between 300 and 600 nucleotides in length, and at least one miRNA hairpin, wherein the spacer is at least 80% identical to SEQ ID NO: 48 or SEQ ID NO: 49.

2. The miRNA expression construct of claim 1, wherein the promoter is a eukaryotic Pol II or Pol III promoter.

3. The miRNA expression construct of claim 2, wherein the promoter has a sequence at least 80% identical to SEQ ID NO: 45.

4. The miRNA expression construct of claim 1, wherein the miRNA hairpin comprises from 5' to 3' and in the order from (a)-(g):
   (a) a mir-16 flanking sequence comprising the sequence of SEQ ID NO: 25;
   (b) a first lower stem sequence comprising the mir-16 sequence of SEQ ID NO: 26, SEQ ID NO: 27, SEQ ID NO: 28, SEQ ID NO: 29 or SEQ ID NO: 30;
   (c) an anti-sense target sequence 22 nucleotides in length;
   (d) a mir-30 loop sequence comprising the sequence of SEQ ID NO: 31;
   (e) a sense sequence wherein the sequence is complementary to the sequence of (c) except that the sequence comprises one or two mismatches relative to the sequence of (c), wherein the one or two mismatches comprise:
      i) a mismatch located at the position 8 to 14 of the sense sequence, optionally located at position 11 of the sense sequence; and/or
      ii) a mismatch at the final 3' position (position 22) of the sense sequence;
   (f) a second lower stem sequence wherein the sequence is complementary to the sequence of (b); and
   (g) a second flanking sequence, optionally wherein the flanking sequence is not complementary to the mir-16 flanking sequence of (a).

5. The miRNA expression construct of claim 1, wherein the nucleic acid molecule is DNA.

6. The miRNA expression construct of claim 1, comprising at least 2, 3, 4, 5, 6, 7, 8, 9, or 10 miRNA hairpins.

7. The miRNA expression construct of claim 6, wherein at least two of the miRNA hairpins target the same sequence.

8. The miRNA expression construct of claim 6, wherein at least two of the miRNA hairpins target different sequences.

9. The miRNA expression construct of claim 1, wherein the miRNA expression construct further comprises a coding sequence for a heterologous protein.

10. The miRNA expression construct of claim 9, wherein the heterologous protein is a chimeric antigen receptor or a T cell receptor.

11. The miRNA expression construct of claim 1, wherein the miRNA expression construct further comprises a selection gene and/or a suicide gene.

12. The miRNA expression construct of claim 1, wherein the miRNA expression construct further comprises a peptide cleavage site.

13. An expression vector comprising the miRNA expression construct of claim 1.

14. A mammalian cell comprising the miRNA expression construct of claim 1.

15. The mammalian cell of claim 14, wherein the mammalian cell is an immune effector cell.

16. A method for preparing engineered immune effector cells, the method comprising transfecting or transducing the immune effector cells with the miRNA expression construct of claim 1.

17. The method of claim 16, comprising transducing or transfecting the immune effector cells with a chimeric antigen receptor or T cell receptor.

* * * * *

UNITED STATES PATENT AND TRADEMARK OFFICE
CERTIFICATE OF CORRECTION

PATENT NO. : 11,649,455 B2
APPLICATION NO. : 15/733703
DATED : May 16, 2023
INVENTOR(S) : Karl-Heinz Krause et al.

It is certified that error appears in the above-identified patent and that said Letters Patent is hereby corrected as shown below:

On the Title Page

Under abstract "17 Claims, 17 Drawing Sheets" should read --19 Claims, 17 Drawing Sheets-- as attached In the Claims At Column 73, Line 12, please insert the following:
--18. The miRNA expression construct of claim 1, wherein the nucleic acid molecule is RNA.
19. A method of treating a patient in need thereof, comprising introducing the cells of claim 14 into the patient.--

Signed and Sealed this
Eighth Day of August, 2023

Katherine Kelly Vidal
*Director of the United States Patent and Trademark Office*

(12) United States Patent
Krause et al.

(10) Patent No.: US 11,649,455 B2
(45) Date of Patent: May 16, 2023

(54) MICRO RNA EXPRESSION CONSTRUCTS AND USES THEREOF

(71) Applicants: UNIVERSITY OF GENEVA, Geneva (CH); LES HÔPITAUX UNIVERSITAIRES DE GENÈVE, Geneva (CH); UNIVERSITY OF ZURICH, Zurich (CH)

(72) Inventors: Karl-Heinz Krause, Geneva (CH); Francis Rousset, Geneva (CH); Patrick Salmon, Geneva (CH); Marco Alessandrini, Geneva (CH); Roberto Speck, Zurich (CH); Simon Bredl, Zurich (CH); Tafadzwa Mlambo, Zurich (CH); Renier Myburgh, Zurich (CH)

(73) Assignees: UNIVERSITY OF GENEVA, Geneva (CH); LES HÔPITAUX UNIVERSITAIRES DE GENÈVE, Geneva (CH); UNIVERSITY OF ZURICH, Zurich (CH)

(*) Notice: Subject to any disclaimer, the term of this patent is extended or adjusted under 35 U.S.C. 154(b) by 0 days.

(21) Appl. No.: 15/733,703

(22) PCT Filed: Apr. 1, 2019

(86) PCT No.: PCT/IB2019/000328
§ 371 (c)(1),
(2) Date: Sep. 30, 2020

(87) PCT Pub. No.: WO2019/186274
PCT Pub. Date: Oct. 3, 2019

(65) Prior Publication Data
US 2021/0095278 A1    Apr. 1, 2021

Related U.S. Application Data

(60) Provisional application No. 62/650,387, filed on Mar. 30, 2018, provisional application No. 62/650,403, filed on Mar. 30, 2018.

(51) Int. Cl.
*C12N 15/113* (2010.01)
*C12N 15/86* (2006.01)
*C12Q 1/68* (2018.01)

(52) U.S. Cl.
CPC ............ *C12N 15/113* (2013.01); *C12N 15/86* (2013.01); *C12N 2310/11* (2013.01); *C12N 2310/141* (2013.01); *C12N 2310/531* (2013.01); *C12N 2320/32* (2013.01)

(58) Field of Classification Search
None
See application file for complete search history.

(56) References Cited

U.S. PATENT DOCUMENTS

| | | |
|---|---|---|
| 5,302,523 A | 4/1994 | Coffee et al. |
| 5,322,783 A | 6/1994 | Tomes et al. |
| 5,384,253 A | 1/1995 | Krzyzek et al. |
| 5,464,765 A | 11/1995 | Coffee et al. |
| 5,486,359 A | 1/1996 | Caplan et al. |
| 5,538,877 A | 7/1996 | Lundquist et al. |
| 5,538,880 A | 7/1996 | Lundquist et al. |
| 5,550,318 A | 8/1996 | Adams et al. |
| 5,563,055 A | 10/1996 | Townsend et al. |
| 5,580,859 A | 12/1996 | Felgner et al. |
| 5,589,466 A | 12/1996 | Felgner et al. |
| 5,591,616 A | 1/1997 | Hiei et al. |
| 5,610,042 A | 3/1997 | Chang et al. |
| 5,656,610 A | 8/1997 | Shuler et al. |
| 5,702,932 A | 12/1997 | Hoy et al. |
| 5,736,524 A | 4/1998 | Content et al. |
| 5,780,448 A | 7/1998 | Davis |
| 5,789,215 A | 8/1998 | Berns et al. |
| 5,908,782 A | 6/1999 | Marshak et al. |
| 5,945,100 A | 8/1999 | Fick |
| 5,981,274 A | 11/1999 | Tyrrell et al. |
| 5,994,136 A | 11/1999 | Naldini et al. |
| 5,994,624 A | 11/1999 | Trolinder et al. |
| 6,013,516 A | 1/2000 | Verma et al. |
| 6,506,559 B1 | 1/2003 | Fire et al. |
| 6,573,099 B2 | 6/2003 | Graham |
| 6,673,611 B2 | 1/2004 | Thompson et al. |
| 9,556,433 B2 | 1/2017 | Krause et al. |
| 2003/0051263 A1 | 3/2003 | Fire et al. |

(Continued)

FOREIGN PATENT DOCUMENTS

| | | |
|---|---|---|
| CN | 101993892 | 3/2011 |
| CN | 105861551 | 8/2016 |

(Continued)

OTHER PUBLICATIONS

Urusov et al. Cells vol. 7(10) 11 pages.*
Carneiro et al., "Abstract No. 897: Co-expression of chimeric antigen receptor (CAR) and miRNAs to T cell therapy," *European Journal of Cancer*, 50(Suppl. 5):s219, 2014.
Office Communication issued in European Patent Application No. 19732112.8, dated Jan. 27, 2022.
Park et al., "Gamma-retroviral vector design for the co-expression of artificial microRNAs and therapeutic proteins," *Nucleic Acid Therapeutics*, 24(5):356-363, 2014.
Supplemental information for Rousset et al., "Optimizing Synthetic miRNA Minigene Architecture for Efficient miRNA Hairpin Concatenation and Multi-target Gene Knockdown," *Molecular Therapy—Nucleic Acids*, 14:351-363 2018.

(Continued)

*Primary Examiner* — Sean McGarry
(74) *Attorney, Agent, or Firm* — ParkerHighlander, PLLC

(57) ABSTRACT

The present disclosure relates to miRNA expression constructs, such as for expression of multiple miRNAs and use thereof to knockdown target gene expression. In some aspects, the expression constructs include a promoter element, a spacer sequence and a miRNA coding sequence. In some aspects, constructs provide enhanced immune cell function.

19 Claims, 17 Drawing Sheets

Specification includes a Sequence Listing.

SEQUENCE LISTING

```
<160> NUMBER OF SEQ ID NOS: 58

<210> SEQ ID NO 1
<211> LENGTH: 56
<212> TYPE: DNA
<213> ORGANISM: Artificial Sequence
<220> FEATURE:
<223> OTHER INFORMATION: Primer

<400> SEQUENCE: 1
ggggacaagt ttgtacaaaa aagcaggctg aattctgagc aagggcgagg agctgt          56

<210> SEQ ID NO 2
<211> LENGTH: 57
<212> TYPE: DNA
<213> ORGANISM: Artificial Sequence
<220> FEATURE:
<223> OTHER INFORMATION: Primer

<400> SEQUENCE: 2
ggggaccact ttgtacaaga aagctgggtc tcgagcttgt acagctcgtc catgccg         57

<210> SEQ ID NO 3
<211> LENGTH: 60
<212> TYPE: DNA
<213> ORGANISM: Artificial Sequence
<220> FEATURE:
```

<223> OTHER INFORMATION: Primer

<400> SEQUENCE: 3 gggacaagt ttgtacaaaa aagcaggctt ctagaatgga tgtaagtagg tgagtgagca    60

<210> SEQ ID NO 4
<211> LENGTH: 60
<212> TYPE: DNA
<213> ORGANISM: Artificial Sequence
<220> FEATURE:
<223> OTHER INFORMATION: Primer

<400> SEQUENCE: 4 gggaccact ttgtacaaga aagctgggtc tcgagcttgt acagctcgtc catgccgaga    60

<210> SEQ ID NO 5
<211> LENGTH: 56
<212> TYPE: DNA
<213> ORGANISM: Artificial Sequence
<220> FEATURE:
<223> OTHER INFORMATION: Primer

<400> SEQUENCE: 5 gggacaagt ttgtacaaaa aagcaggctg aattctgagc aagggcgagg agctgt    56

<210> SEQ ID NO 6
<211> LENGTH: 32
<212> TYPE: DNA
<213> ORGANISM: Artificial Sequence
<220> FEATURE:
<223> OTHER INFORMATION: Primer

<400> SEQUENCE: 6
gggggctcga gtcgccctcg aacttcacct cg                                 32

<210> SEQ ID NO 7
<211> LENGTH: 32
<212> TYPE: DNA
<213> ORGANISM: Artificial Sequence
<220> FEATURE:
<223> OTHER INFORMATION: Primer

<400> SEQUENCE: 7 gggggggaatt ccaccctggt gaaccgcatc ga                                32

<210> SEQ ID NO 8
<211> LENGTH: 57
<212> TYPE: DNA
<213> ORGANISM: Artificial Sequence
<220> FEATURE:
<223> OTHER INFORMATION: Primer

<400> SEQUENCE: 8 gggaccact ttgtacaaga aagctgggtc tcgagcttgt acagctcgtc catgccg      57

<210> SEQ ID NO 9
<211> LENGTH: 59
<212> TYPE: DNA
<213> ORGANISM: Artificial Sequence
<220> FEATURE:
<223> OTHER INFORMATION: Primer

<400> SEQUENCE: 9 gggaccact ttgtacaaga aagctgggtc tcgagctaga ggatcccct gttccacct     59

```
<210> SEQ ID NO 10
<211> LENGTH: 60
<212> TYPE: DNA
<213> ORGANISM: Artificial Sequence
<220> FEATURE:
<223> OTHER INFORMATION: Primer

<400> SEQUENCE: 10
ggggacaagt tgtacaaaa aagcaggctg aattctcacc atggggcag gtgccaccgg       60

<210> SEQ ID NO 11
<211> LENGTH: 60
<212> TYPE: DNA
<213> ORGANISM: Artificial Sequence
<220> FEATURE:
<223> OTHER INFORMATION: Primer

<400> SEQUENCE: 11
ggggacaagt tgtacaaaa aagcaggctg aattctcacc atggagcgtc cgcaacccga      60

<210> SEQ ID NO 12
<211> LENGTH: 49
<212> TYPE: DNA
<213> ORGANISM: Artificial Sequence
<220> FEATURE:
<223> OTHER INFORMATION: Primer

<400> SEQUENCE: 12
ggggaccact ttgtacaaga aagctgggtc tacagcaact gtcgccacc                 49

<210> SEQ ID NO 13
<211> LENGTH: 84
<212> TYPE: DNA
<213> ORGANISM: Artificial Sequence
<220> FEATURE:
<223> OTHER INFORMATION: Primer

<400> SEQUENCE: 13
ggggacaagt tgtacaaaa aagcaggctg aattctaata gtgaccactc ctggctaatt      60
tttgtatttt cagtagagat aggg                                            84

<210> SEQ ID NO 14
<211> LENGTH: 79
<212> TYPE: DNA
<213> ORGANISM: Artificial Sequence
<220> FEATURE:
<223> OTHER INFORMATION: Primer

<400> SEQUENCE: 14
ggggaccact ttgtacaaga aagctgggtc tcgagggtga acccttctc tactaaaaat      60 acaaaattag ccgggcaca                                                  79

<210> SEQ ID NO 15
<211> LENGTH: 75
<212> TYPE: DNA
<213> ORGANISM: Artificial Sequence
<220> FEATURE:
<223> OTHER INFORMATION: Primer

<400> SEQUENCE: 15
ggggaccact ttgtacaaga aagctgggtc tcgagccgca ctccagcctc ggcgacagag     60
caagactcta tctca                                                      75

<210> SEQ ID NO 16
```

```
<211> LENGTH: 75
<212> TYPE: DNA
<213> ORGANISM: Artificial Sequence
<220> FEATURE:
<223> OTHER INFORMATION: Primer

<400> SEQUENCE: 16
ggggaccact tgtacaaga aagctgggtc tcgagtcggg agtacgagac cagcctggcc       60
aacatagtga aatcc                                                      75

<210> SEQ ID NO 17
<211> LENGTH: 56
<212> TYPE: DNA
<213> ORGANISM: Artificial Sequence
<220> FEATURE:
<223> OTHER INFORMATION: Primer

<400> SEQUENCE: 17
ggggacaagt ttgtacaaaa aagcaggctg aattcatgcc agagccagcg aagtcr         56

<210> SEQ ID NO 18
<211> LENGTH: 56
<212> TYPE: DNA
<213> ORGANISM: Artificial Sequence
<220> FEATURE:
<223> OTHER INFORMATION: Primer

<400> SEQUENCE: 18
ggggaccact tgtacaaga aagctgggtc tcgaggtgta cttggtgacg gcctta          56

<210> SEQ ID NO 19
<211> LENGTH: 50
<212> TYPE: DNA
<213> ORGANISM: Artificial Sequence
<220> FEATURE:
<223> OTHER INFORMATION: Primer

<400> SEQUENCE: 19
cagaagggga tccatcgata ctagtggtga tagcaatgtc agcagtgcct                50

<210> SEQ ID NO 20
<211> LENGTH: 36
<212> TYPE: DNA
<213> ORGANISM: Artificial Sequence
<220> FEATURE:
<223> OTHER INFORMATION: Primer

<400> SEQUENCE: 20
agtagcttct agagtagagt atggtcaacc ttactt                               36

<210> SEQ ID NO 21
<211> LENGTH: 38
<212> TYPE: DNA
<213> ORGANISM: Artificial Sequence
<220> FEATURE:
<223> OTHER INFORMATION: Primer

<400> SEQUENCE: 21
cagaagggga tccggtgata gcaatgtcag cagtgcct                             38

<210> SEQ ID NO 22
<211> LENGTH: 36
<212> TYPE: DNA
<213> ORGANISM: Artificial Sequence
<220> FEATURE:
<223> OTHER INFORMATION: Primer
```

<400> SEQUENCE: 22
agtagctact agtgtagagt atggtcaacc ttactt    36

<210> SEQ ID NO 23
<211> LENGTH: 38
<212> TYPE: DNA
<213> ORGANISM: Artificial Sequence
<220> FEATURE:
<223> OTHER INFORMATION: Primer

<400> SEQUENCE: 23
cagaaggctc gagggtgata gcaatgtcag cagtgcct    38

<210> SEQ ID NO 24
<211> LENGTH: 36
<212> TYPE: DNA
<213> ORGANISM: Artificial Sequence
<220> FEATURE:
<223> OTHER INFORMATION: Primer

<400> SEQUENCE: 24
agtagctgga tccgtagagt atggtcaacc ttactt    36

<210> SEQ ID NO 25
<211> LENGTH: 12
<212> TYPE: DNA
<213> ORGANISM: Artificial Sequence
<220> FEATURE:
<223> OTHER INFORMATION: mir-16

<400> SEQUENCE: 25
ggtgatagca at    12

<210> SEQ ID NO 26
<211> LENGTH: 11
<212> TYPE: DNA
<213> ORGANISM: Artificial Sequence
<220> FEATURE:
<223> OTHER INFORMATION: Lower stem

<400> SEQUENCE: 26
cagcagtgcc t    11

<210> SEQ ID NO 27
<211> LENGTH: 12
<212> TYPE: DNA
<213> ORGANISM: Artificial Sequence
<220> FEATURE:
<223> OTHER INFORMATION: Lower stem

<400> SEQUENCE: 27
tcagcagtgc ct    12

<210> SEQ ID NO 28
<211> LENGTH: 13
<212> TYPE: DNA
<213> ORGANISM: Artificial Sequence
<220> FEATURE:
<223> OTHER INFORMATION: Lower stem

<400> SEQUENCE: 28
gtcagcagtg cct    13

<210> SEQ ID NO 29

```
<211> LENGTH: 14
<212> TYPE: DNA
<213> ORGANISM: Artificial Sequence
<220> FEATURE:
<223> OTHER INFORMATION: Lower stem

<400> SEQUENCE: 29
cgtcagcagt gcct                                                         14

<210> SEQ ID NO 30
<211> LENGTH: 15
<212> TYPE: DNA
<213> ORGANISM: Artificial Sequence
<220> FEATURE:
<223> OTHER INFORMATION: Lower stem

<400> SEQUENCE: 30
acgtcagcag tgcct                                                        15

<210> SEQ ID NO 31
<211> LENGTH: 15
<212> TYPE: DNA
<213> ORGANISM: Artificial Sequence
<220> FEATURE:
<223> OTHER INFORMATION: Lower stem

<400> SEQUENCE: 31
gtgaagccac agatg                                                        15

<210> SEQ ID NO 32
<211> LENGTH: 107
<212> TYPE: DNA
<213> ORGANISM: Artificial Sequence
<220> FEATURE:
<223> OTHER INFORMATION: miRGE CCR5-7

<400> SEQUENCE: 32
ggtgatagca atgtcagcag tgccttcata gattggactt gacacttgtg aagccacaga       60
tgaagtgtca agcccaatct atgcaagtaa ggttgaccat actctac                    107

<210> SEQ ID NO 33
<211> LENGTH: 107
<212> TYPE: DNA
<213> ORGANISM: Artificial Sequence
<220> FEATURE:
<223> OTHER INFORMATION: miRGE GFP

<400> SEQUENCE: 33
ggtgatagca atgtcagcag tgcctagttc accttgatgc cgttcttgtg aagccacaga       60
tgaagaacgg caccaaggtg aaccaagtaa ggttgaccat actctac                    107

<210> SEQ ID NO 34
<211> LENGTH: 107
<212> TYPE: DNA
<213> ORGANISM: Artificial Sequence
<220> FEATURE:
<223> OTHER INFORMATION: miRGE p22phox

<400> SEQUENCE: 34
ggtgatagca atgtcagcag tgcctacatg gcccactcga tctgcccgtg aagccacaga       60
tggggcagat cgcgtgggcc atgcaagtaa ggttgaccat actctac                    107

<210> SEQ ID NO 35
<211> LENGTH: 20
```

<212> TYPE: DNA
<213> ORGANISM: Artificial Sequence
<220> FEATURE:
<223> OTHER INFORMATION: Primer

<400> SEQUENCE: 35
tggacgtttc acacagtggt                                           20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
tggacccctt tttcctcttt                                           20

<210> SEQ ID NO 37
<211> LENGTH: 25
<212> TYPE: DNA
<213> ORGANISM: Artificial Sequence
<220> FEATURE:
<223> OTHER INFORMATION: Primer

<400> SEQUENCE: 37
ggtgatagca atgtcagcag tgcct                                     25

<210> SEQ ID NO 38
<211> LENGTH: 23
<212> TYPE: DNA
<213> ORGANISM: Artificial Sequence
<220> FEATURE:
<223> OTHER INFORMATION: Primer

<400> SEQUENCE: 38
gtagagtatg gtcaacctta ctt                                       23

<210> SEQ ID NO 39
<211> LENGTH: 23
<212> TYPE: DNA
<213> ORGANISM: Artificial Sequence
<220> FEATURE:
<223> OTHER INFORMATION: Primer

<400> SEQUENCE: 39
ggagctagaa cgattcgcag tta                                       23

<210> SEQ ID NO 40
<211> LENGTH: 25
<212> TYPE: DNA
<213> ORGANISM: Artificial Sequence
<220> FEATURE:
<223> OTHER INFORMATION: Primer

<400> SEQUENCE: 40
ggttgtagct gtcccagtat ttgtc                                     25

<210> SEQ ID NO 41
<211> LENGTH: 19
<212> TYPE: DNA
<213> ORGANISM: Artificial Sequence
<220> FEATURE:
<223> OTHER INFORMATION: Primer

<400> SEQUENCE: 41
tccacttggt cgctttgct                                                     19

<210> SEQ ID NO 42
<211> LENGTH: 23
<212> TYPE: DNA
<213> ORGANISM: Artificial Sequence
<220> FEATURE:
<223> OTHER INFORMATION: Primer

<400> SEQUENCE: 42
cttcttgtcc acagctttga tga                                                23

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
tccatgacaa ctttggcatt g                                                  21

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
cagtcttctg ggtggcagtg a                                                  21

<210> SEQ ID NO 45
<211> LENGTH: 248
<212> TYPE: DNA
<213> ORGANISM: Artificial Sequence
<220> FEATURE:
<223> OTHER INFORMATION: EF1 promoter

<400> SEQUENCE: 45
cgatggctcc ggtgcccgtc agtgggcaga gcgcacatcg cccacagtcc ccgagaagtt        60 gggggggaggg gtcggcaatt gaaccggtgc ctagagaagg tggcgcgggg taaactggga     120
aagtgatgtc gtgtactggc tccgcctttt tcccgagggt gggggagaac cgtatataag     180
tgcagtagtc gccgtgaacg ttcttttttcg caacgggttt gccgccagaa cacaggtgtc     240
gtgacgcg                                                               248

<210> SEQ ID NO 46
<211> LENGTH: 758
<212> TYPE: DNA
<213> ORGANISM: Artificial Sequence
<220> FEATURE:
<223> OTHER INFORMATION: Spacer

<400> SEQUENCE: 46
atggatgtaa gtaggtgagt gagcaagggc gaggagctgt tcaccggggt ggtgcccatc        60
ctggtcgagc tggacggcga cgtaaacggc cacaagttca gcgtgtccgg cgagggcgag     120
ggcgatgcca cctacggcaa gctgaccctg aagttcatct gcaccaccgg caagctgccc     180
gtgccctggc ccaccctcgt gaccaccctg acctacggcg tgcagtgctt cagccgctac     240

```
cccgaccaca tgaagcagca cgacttcttc aagtccgcca tgcccgaagg ctacgtccag    300
gagcgcacca tcttcttcaa ggacgacggc aactacaaga cccgcgccga ggtgaagttc    360
gagggcgacc accctggtga accgcatcga gctgaagggc atcgacttca aggaggacgg    420
caacatcctg gggcacaagc tggagtacaa ctacaacagc cacaacgtct atatcatggc    480
cgacaagcag aagaacggca tcaaggtgaa cttcaagatc cgccacaaca tcgaggacgg    540
cagcgtgcag ctcgccgacc actaccagca gaacaccccc atcggcgacg gccccgtgct    600
gctgcccgac aaccactacc tgagcaccca gtccgccctg agcaaagacc ccaacgagaa    660
gcgcgatcac atggtcctgc tggagttcgt gaccgccgcc gggatcactc tcggcatgga    720
cgagctgtac aagtaaagcg gcctgaatcg ccagtgtc                            758

<210> SEQ ID NO 47
<211> LENGTH: 762
<212> TYPE: DNA
<213> ORGANISM: Artificial Sequence
<220> FEATURE:
<223> OTHER INFORMATION: Spacer

<400> SEQUENCE: 47
aattcatgga tgtaagtagg tgagtgagca agggcgagga gctgttcacc ggggtggtgc     60
ccatcctggt cgagctggac ggcgacgtaa acggccacaa gttcagcgtg tccggcgagg    120
gcgagggcga tgccacctac ggcaagctga ccctgaagtt catctgcacc accggcaagc    180
tgcccgtgcc ctggcccacc ctcgtgacca ccctgaccta cggcgtgcag tgcttcagcc    240
gctaccccga ccacatgaag cagcacgact tcttcaagtc cgccatgccc gaaggctacg    300
tccaggagcg caccatcttc ttcaaggacg acggcaacta caagacccgc gccgaggtga    360
agttcgaggg cgacaccctg gtgaaccgca tcgagctgaa gggcatcgac ttcaaggagg    420
acggcaacat cctggggcac aagctggagt acaactacaa cagccacaac gtctatatca    480
tggccgacaa gcagaagaac ggcatcaagg tgaacttcaa gatccgccac aacatcgagg    540
acggcagcgt gcagctcgcc gaccactacc agcagaacac ccccatcggc gacggccccg    600
tgctgctgcc cgacaaccac tacctgagca cccagtccgc cctgagcaaa gaccccaacg    660
agaagcgcga tcacatggtc ctgctggagt tcgtgaccgc cgccgggatc actctcggca    720
tggacgagct gtacaagtaa agcggcctga atcgccagtg tc                      762

<210> SEQ ID NO 48
<211> LENGTH: 375
<212> TYPE: DNA
<213> ORGANISM: Artificial Sequence
<220> FEATURE:
<223> OTHER INFORMATION: Spacer

<400> SEQUENCE: 48
aattcatgga tgtaagtagg tgagtgagca agggcgagga gctgttcacc ggggtggtgc     60
ccatcctggt cgagctggac ggcgacgtaa acggccacaa gttcagcgtg tccggcgagg    120
gcgagggcga tgccacctac ggcaagctga ccctgaagtt catctgcacc accggcaagc    180
tgcccgtgcc ctggcccacc ctcgtgacca ccctgaccta cggcgtgcag tgcttcagcc    240
gctaccccga ccacatgaag cagcacgact tcttcaagtc cgccatgccc gaaggctacg    300
tccaggagcg caccatcttc ttcaaggacg acggcaacta caagacccgc gccgaggtga    360
agttcgaggg cgacc                                                    375
```

```
<210> SEQ ID NO 49
<211> LENGTH: 394
<212> TYPE: DNA
<213> ORGANISM: Artificial Sequence
<220> FEATURE:
<223> OTHER INFORMATION: Spacer

<400> SEQUENCE: 49
aattccaccc tggtgaaccg catcgagctg aagggcatcg acttcaagga ggacggcaac        60
atcctggggc acaagctgga gtacaactac aacagccaca cgtctatat catgccgac         120 aagcagaaga acggcatcaa ggtgaacttc aagatccgcc acaacatcga ggacggcagc       180
gtgcagctcg ccgaccacta ccagcagaac acccccatcg gcgacggccc cgtgctgctg       240
cccgacaacc actacctgag cacccagtcc gccctgagca agacccccaa cgagaagcgc       300
gatcacatgg tcctgctgga gttcgtgacc gccgccggga tcactctcgg catggacgag       360
ctgtacaagt aaagcggcct gaatcgccag tgtc                                   394

<210> SEQ ID NO 50
<211> LENGTH: 378
<212> TYPE: DNA
<213> ORGANISM: Artificial Sequence
<220> FEATURE:
<223> OTHER INFORMATION: Spacer

<400> SEQUENCE: 50
atgccagagc cagcgaagtc tgctcccgcc ccgaaaaagg gctccaagaa ggcggtgact        60
aaggcgcaga agaaaggcgg caagaagcgc aagcgcagcc gcaaggagag ctattccatc       120
tatgtgtaca aggttctgaa gcaggtccac cctgacaccg gcatttcgtc caaggccatg       180
ggcatcatga attcgtttgt gaacgacatt ttcgagcgca tcgcaggtga ggcttcccgc       240
ctggcgcatt acaacaagcg ctcgaccatc acctccaggg agatccagac ggccgtgcgc       300
ctgctgctgc ctggggagtt ggccaagcac gccgtgtccg agggtactaa ggccgtcacc       360
aagtacacca gcgctaag                                                     378

<210> SEQ ID NO 51
<211> LENGTH: 854
<212> TYPE: DNA
<213> ORGANISM: Artificial Sequence
<220> FEATURE:
<223> OTHER INFORMATION: Spacer

<400> SEQUENCE: 51
aattctcacc atgggggcag gtgccaccgg ccgcgccatg gacgggccgc gcctgctgct        60
gttgctgctt ctgggggtgt cccttggagg tgccaaggag gcatgcccca caggcctgta      120
cacacacagc ggtgagtgct gcaaagcctg caacctgggc gagggtgtgg cccagccttg      180
tggagccaac cagaccgtgt gtgagccctg cctggacagc gtgacgttct ccgacgtggt      240
gagcgcgacc gagccgtgca agccgtgcac cgagtgcgtg ggctccaga gcatgtcggc       300 gccgtgcgtg gaggccgacg acgccgtgtg ccgctgcgcc tacggctact accaggatga      360
gacgactggg cgctgcgagg cgtgccgcgt gtgcgaggcg ggctcgggcc tcgtgttctc      420
ctgccaggac aagcagaaca ccgtgtgcga ggagtgcccc gacggcacgt attccgacga      480
ggccaaccac gtggacccgt gcctgccctg caccgtgtgc gaggacaccg agcgccagct      540
ccgcgagtgc acacgctggg ccgacgccga gtgcgaggag atccctggcc gttggattac      600
acggtccaca cccccagagg gctcggacag cacagccccc agcacccagg agcctgaggc      660
```

| | |
|---|---|
| acctccagaa caagacctca tagccagcac ggtggcaggt gtggtgacca cagtgatggg | 720 |
| cagctcccag cccgtggtga cccgaggcac caccgacaac ctcatccctg tctattgctc | 780 |
| catcctggct gctgtggttg tgggccttgt ggcctacata gccttcaaga ggtggaacag | 840 |
| ggggatcctc tagc | 854 |

```
<210> SEQ ID NO 52
<211> LENGTH: 730
<212> TYPE: DNA
<213> ORGANISM: Artificial Sequence
<220> FEATURE:
<223> OTHER INFORMATION: Spacer

<400> SEQUENCE: 52
```

| | |
|---|---|
| aattcggcac gagggacttc tgttccagag caaaggtcat tcagccgctt gaatcagcct | 60 |
| tttcccccca cccggtcccc aactttgttt acccgataag gaaggtcagc attcaaagtc | 120 |
| aagaagcgcc atttatcttc ccgtgcgctc tacaaatagt tccgtgagaa agatggccgg | 180 |
| gaactcgatc ctgctggctg ctgtctctat tctctcggcc tgtcagcaaa gttattttgc | 240 |
| tttgcaagtt ggaaaggcaa gattaaaata caaagttacg cccccagcag tcactgggtc | 300 |
| accagagttt gagagagtat ttcgggcaca acaaaactgt gtggagtttt atcctatatt | 360 |
| cataattaca ttgtggatgg ctgggtggta tttcaaccaa gttttttgcta cttgtctggg | 420 |
| tctggtgtac atatatggcc gtcacctata cttctgggga tattcagaag ctgctaaaaa | 480 |
| acggatcacc ggtttccgac tgagtctggg gattttggcc ttgttgaccc tcctaggtgc | 540 |
| cctgggaatt gcaaacagct ttctggatga atatctggac ctcaatattg ccaagaaact | 600 |
| gaggcggcaa ttctaacttt ttctcttccc tttaatgctt gcagaagctg ttcccaccat | 660 |
| gaaggtaata tggtatcatt tgttaaataa aaataaagtc tttattctgt taaaaaaaaa | 720 |
| aaaaaaaaac | 730 |

```
<210> SEQ ID NO 53
<211> LENGTH: 873
<212> TYPE: DNA
<213> ORGANISM: Artificial Sequence
<220> FEATURE:
<223> OTHER INFORMATION: Spacer

<400> SEQUENCE: 53
```

| | |
|---|---|
| aattcatgga gcgtccgcaa cccgacagca tgccccagga tttgtcagag gccctgaagg | 60 |
| aggccaccaa ggaggtgcac acccaggcag agaatgctga gttcatgagg aactttcaga | 120 |
| agggccaggt gacccgagac ggcttcaagc tggtgatggc ctccctgtac cacatctatg | 180 |
| tggccctgga ggaggagatt gagcgcaaca aggagagccc agtcttcgcc ctgtctact | 240 |
| tcccagaaga gctgcaccgc aaggctgccc tggagcagga cctggccttc tggtacgggc | 300 |
| cccgctggca ggaggtcatc ccctacacac cagccatgca cgctatgtg aagcggctcc | 360 |
| acgaggtggg gcgcacagag cccgagctgc tggtggccca cgcctacacc cgctacctgg | 420 |
| gtgacctgtc tgggggccag gtgctcaaaa agattgccca gaaagccctg gacctgccca | 480 |
| gctctggcga gggcctggcc ttcttcacct tccccaacat tgccagtgcc accaagttca | 540 |
| agcagctcta ccgctcccgc atgaactccc tggagatgac tccgcagtc aggcagaggg | 600 |
| tgatagaaga ggccaagact gcgttcctgc tcaacatcca gctctttgag gagttgcagg | 660 |
| agctgctgac ccatgacacc aaggaccaga gcccctcacg ggcaccaggg cttcgccagc | 720 |
| gggccagcaa caaagtgcaa gattctgccc ccgtggagac tcccagaggg aagcccccac | 780 |

```
tcaacacccg ctcccaggct ccgcttctcc gatgggtcct tacactcagc tttctggtgg    840
cgacagttgc tgtagggctt tatgccatgt gac                                 873
```

<210> SEQ ID NO 54
<211> LENGTH: 781
<212> TYPE: DNA
<213> ORGANISM: Artificial Sequence
<220> FEATURE:
<223> OTHER INFORMATION: Spacer

<400> SEQUENCE: 54

```
aattctaata gtgaccactc ctggctaatt tttgtatttt cagtagagat agggtttcac     60
tatgttggcc aggctggtct ccaactcctg acctaaagtg atccacccac cttggtttcc    120
caaagtgctg ggattacagg cgtgagccac cgtgcctgga catatatcta tctttttttt    180
ttttgagatg gagtctcgct ctgttgccca ggctggagtg cagtggcgtg atttcggctc    240
actgcaacct ccgcctcccg ggttcaagtg attctcctgc ctcagcctcc caagtagctg    300
agattacaga cgtgcgtcac catgcccagc taattttttgt attttttagta gagatgggat    360 ttcactatgt tggccaggct ggtctcgtac tcccgacctc aggtgatcca cttgccttgg    420
cctcccaaag tgctggaatt acaggtgtga gccactgcat ccggccttat atatctatct    480
tgtctgtctg actgtctaat ctaattcatc tattttatct gtttatctta tctatcatct    540
atttatctaa tctatctgtc tgtatgtctg tttttttttt gtttttttt ttttttttgag    600 atagagtctt gctctgtcgc cgaggctgga gtgcggtggc gcgatctcag ctcactgctg    660
aacctccgcc tcctgggttc taagcgattc tcctgcctca atctttggag tagctgggat    720
tacaggcccg taccactgtg cccggctaat tttgtatttt tagtagagaa gggtttcacc    780
c                                                                    781
```

<210> SEQ ID NO 55
<211> LENGTH: 637
<212> TYPE: DNA
<213> ORGANISM: Artificial Sequence
<220> FEATURE:
<223> OTHER INFORMATION: Spacer

<400> SEQUENCE: 55

```
aattctaata gtgaccactc ctggctaatt tttgtatttt cagtagagat agggtttcac     60
tatgttggcc aggctggtct ccaactcctg acctaaagtg atccacccac cttggtttcc    120
caaagtgctg ggattacagg cgtgagccac cgtgcctgga catatatcta tctttttttt    180
ttttgagatg gagtctcgct ctgttgccca ggctggagtg cagtggcgtg atttcggctc    240
actgcaacct ccgcctcccg ggttcaagtg attctcctgc ctcagcctcc caagtagctg    300
agattacaga cgtgcgtcac catgcccagc taattttttgt attttttagta gagatgggat    360 ttcactatgt tggccaggct ggtctcgtac tcccgacctc aggtgatcca cttgccttgg    420
cctcccaaag tgctggaatt acaggtgtga gccactgcat ccggccttat atatctatct    480
tgtctgtctg actgtctaat ctaattcatc tattttatct gtttatctta tctatcatct    540
atttatctaa tctatctgtc tgtatgtctg tttttttttt gtttttttt ttttttttgag    600 atagagtctt gctctgtcgc cgaggctgga gtgcggc                             637
```

<210> SEQ ID NO 56
<211> LENGTH: 254
<212> TYPE: DNA

```
<213> ORGANISM: Artificial Sequence
<220> FEATURE:
<223> OTHER INFORMATION: Spacer

<400> SEQUENCE: 56
aattctaata gtgaccactc ctggctaatt tttgtattt cagtagagat agggtttcac    60
tatgttggcc aggctggtct ccaactcctg acctaaagtg atccaccac cttggtttcc   120 caaagtgctg ggattacagg cgtgagccac cgtgcctgga catatatcta tctttttttt   180
ttttgagatg gagtctcgct ctgttgccca ggctggagtg cagtggcgtg atttcggctc   240
actgcaacct ccgc                                                    254

<210> SEQ ID NO 57
<211> LENGTH: 22
<212> TYPE: DNA
<213> ORGANISM: Artificial Sequence
<220> FEATURE:
<223> OTHER INFORMATION: Primer

<400> SEQUENCE: 57
aagaacggca tcaaggtgaa ct                                            22

<210> SEQ ID NO 58
<211> LENGTH: 22
<212> TYPE: DNA
<213> ORGANISM: Artificial Sequence
<220> FEATURE:
<223> OTHER INFORMATION: Primer

<400> SEQUENCE: 58
aagtgtcaag tccaatctat ga                                            22
```